(12) United States Patent
Ulm, III

(10) Patent No.: US 11,160,572 B2
(45) Date of Patent: Nov. 2, 2021

(54) CLOT RETRIEVAL SYSTEM

(71) Applicant: Legacy Ventures LLC, Nashville, TN (US)

(72) Inventor: Arthur John Ulm, III, Nashville, TN (US)

(73) Assignee: Legacy Ventures LLC, Nashville, TN (US)

( * ) Notice: Subject to any disclaimer, the term of this patent is extended or adjusted under 35 U.S.C. 154(b) by 0 days.

(21) Appl. No.: 17/075,304

(22) Filed: Oct. 20, 2020

(65) Prior Publication Data

US 2021/0045760 A1    Feb. 18, 2021

Related U.S. Application Data

(63) Continuation-in-part of application No. 16/579,427, filed on Sep. 23, 2019, which is a continuation of application No. 16/385,862, filed on Apr. 16, 2019, now Pat. No. 10,420,572, which is a continuation-in-part of application No. 15/947,955, filed on Apr. 9, 2018, now Pat. No. 10,258,356, which is a continuation-in-part of application No. 14/794,783, filed on Jul. 8, 2015, now Pat. No.
(Continued)

(51) Int. Cl.
| | |
|---|---|
| *A61B 17/221* | (2006.01) |
| *A61B 6/12* | (2006.01) |
| *A61M 25/01* | (2006.01) |
| *A61B 17/00* | (2006.01) |
| *A61B 90/00* | (2016.01) |
| *A61B 17/22* | (2006.01) |

(52) U.S. Cl.
CPC .............. *A61B 17/221* (2013.01); *A61B 6/12* (2013.01); *A61B 17/00234* (2013.01); *A61M 25/0108* (2013.01); *A61B 17/22032* (2013.01); *A61B 2017/00323* (2013.01); *A61B 2017/00526* (2013.01); *A61B 2017/00778* (2013.01); *A61B 2017/00867* (2013.01); *A61B 2017/2212* (2013.01); *A61B 2090/3966* (2016.02)

(58) Field of Classification Search
CPC ........ A61B 17/00234; A61B 17/22032; A61B 17/221; A61B 2017/00323; A61B 2017/00526; A61B 2017/00778; A61B 2017/00867; A61B 2017/2212; A61B 2090/3966; A61B 6/12; A61M 25/0108
See application file for complete search history.

(56) References Cited

U.S. PATENT DOCUMENTS

| | | |
|---|---|---|
| 8,430,837 B2 | 4/2013 | Jenson et al. |
| 9,259,237 B2 | 2/2016 | Quick et al. |

(Continued)

FOREIGN PATENT DOCUMENTS

| | | |
|---|---|---|
| EP | 3335647 A2 | 6/2018 |
| EP | 3639768 A1 | 4/2020 |
| WO | 2018033401 A1 | 2/2018 |

*Primary Examiner* — Mohamed G Gabr
(74) *Attorney, Agent, or Firm* — Shane Cortesi

(57) ABSTRACT

A platform of devices for removing obstructions and other objects within a blood vessel or other interior lumen of an animal is provided. The system may be deployed in the lumen from a catheter(s) and the system may include a cage comprising a suction catheter comprising one or more suction openings located in the cage interior in order to draw the clot or other object into the cage interior.

29 Claims, 55 Drawing Sheets

Related U.S. Application Data

9,962,177, which is a continuation-in-part of application No. PCT/US2015/031447, filed on May 18, 2015, and a continuation-in-part of application No. PCT/US2015/010178, filed on Jan. 5, 2015, which is a continuation-in-part of application No. 14/558,712, filed on Dec. 2, 2014, now Pat. No. 9,155,552, said application No. 14/794,783 is a continuation-in-part of application No. 14/558,712, filed on Dec. 2, 2014, now Pat. No. 9,155,552, which is a continuation of application No. 14/558,705, filed on Dec. 2, 2014, now Pat. No. 9,173,668, and application No. 14/558,705, which is a continuation-in-part of application No. 14/147,491, filed on Jan. 3, 2014, now Pat. No. 8,900,265.

(60) Provisional application No. 61/994,934, filed on May 18, 2014, provisional application No. 61/994,919, filed on May 18, 2014.

(56) References Cited

U.S. PATENT DOCUMENTS

| | | |
|---|---|---|
| 9,855,067 B2 | 1/2018 | Krolik et al. |
| 9,999,493 B2 | 6/2018 | Nguyen et al. |
| 2012/0116440 A1* | 5/2012 | Leynov .................. A61B 17/22 606/200 |
| 2015/0005792 A1* | 1/2015 | Ahn ...................... A61B 17/221 606/159 |
| 2016/0270813 A1 | 9/2016 | Chida |
| 2017/0259042 A1* | 9/2017 | Nguyen ............ A61M 25/1006 |
| 2019/0000500 A1 | 1/2019 | Masubuchi et al. |

* cited by examiner

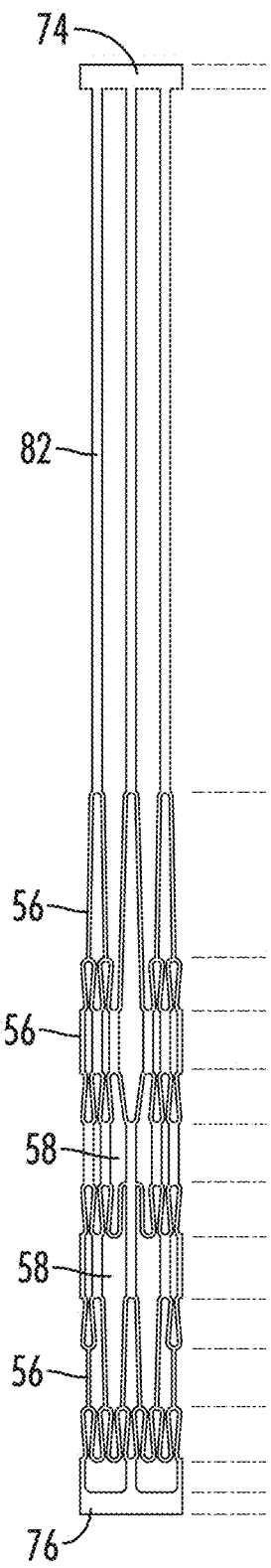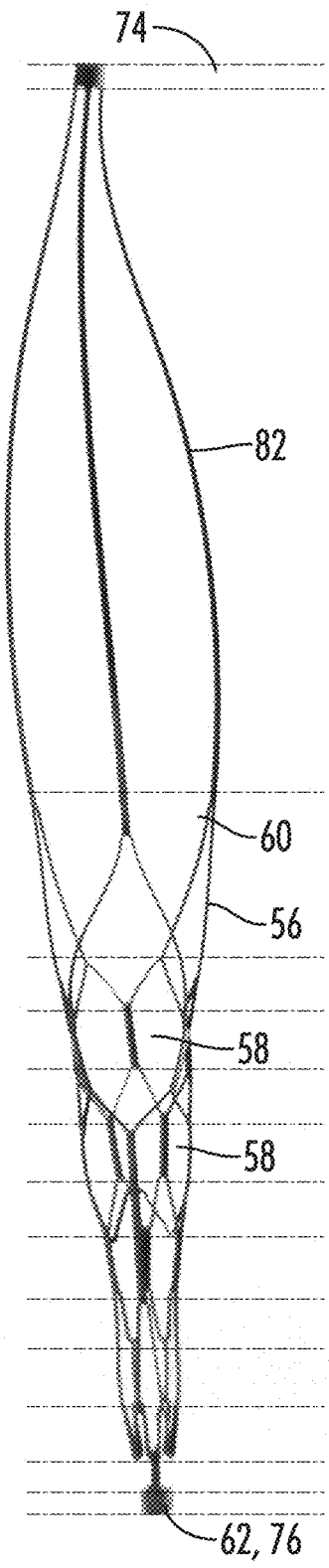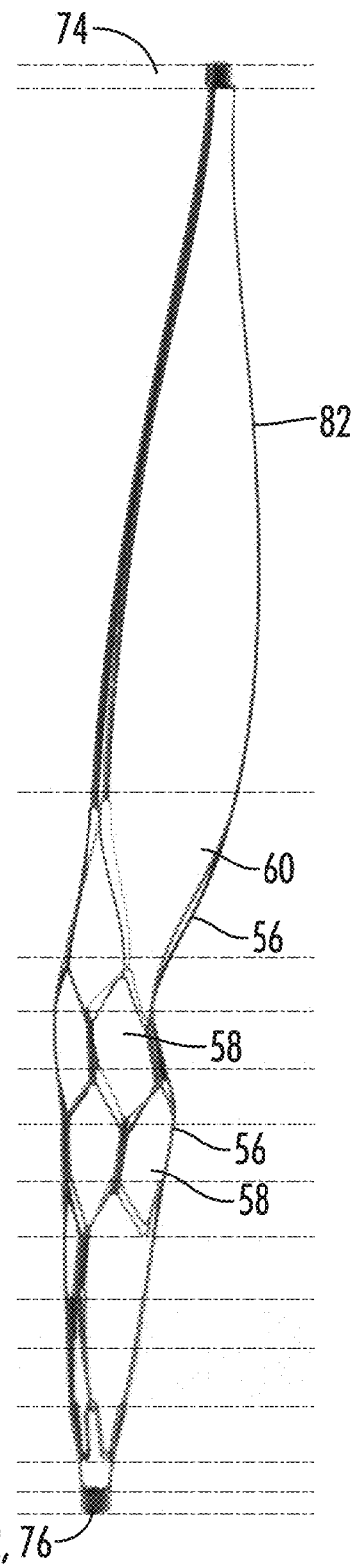
*FIG. 2A*   *FIG. 2B*   *FIG. 2C*

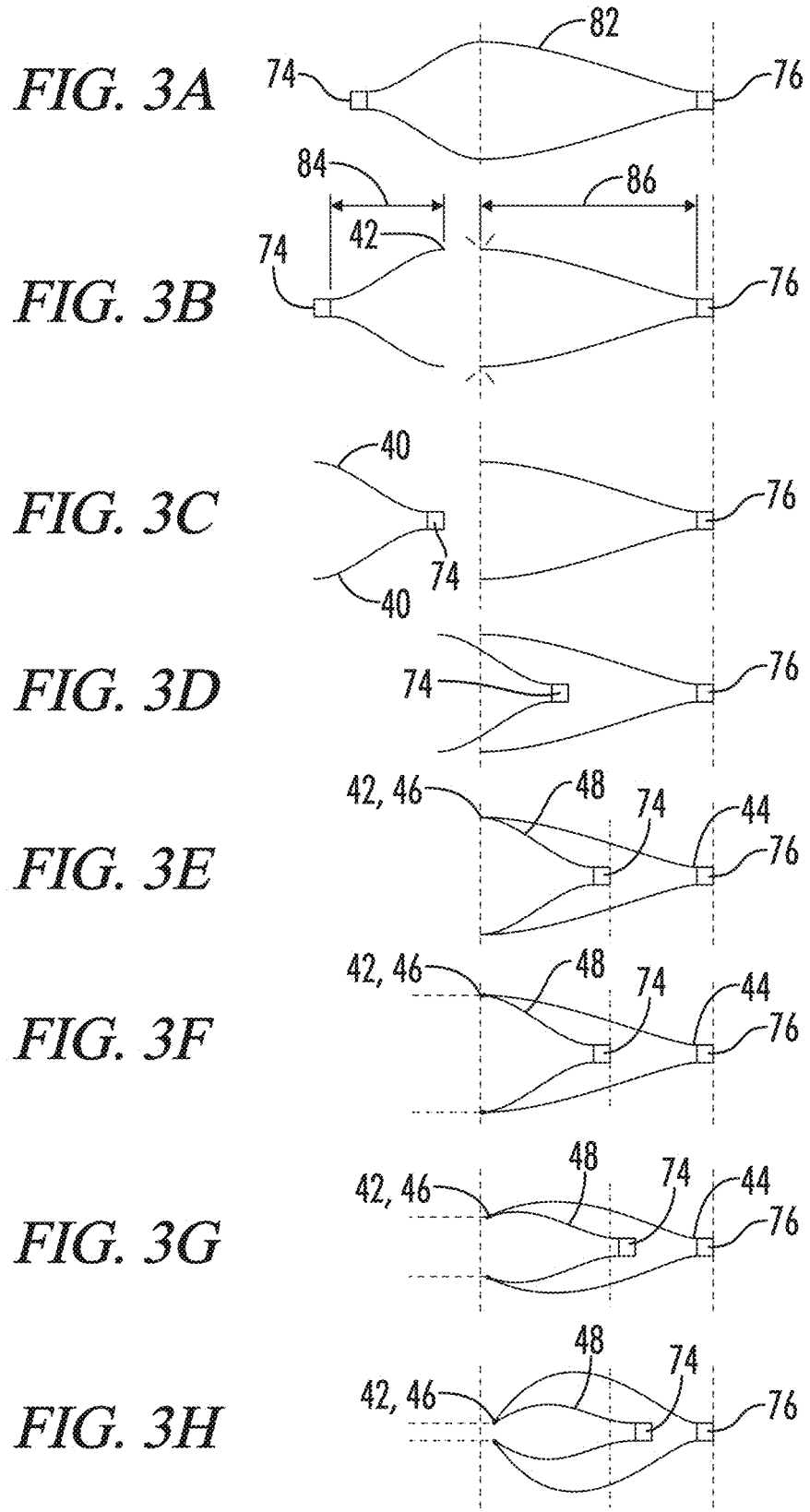

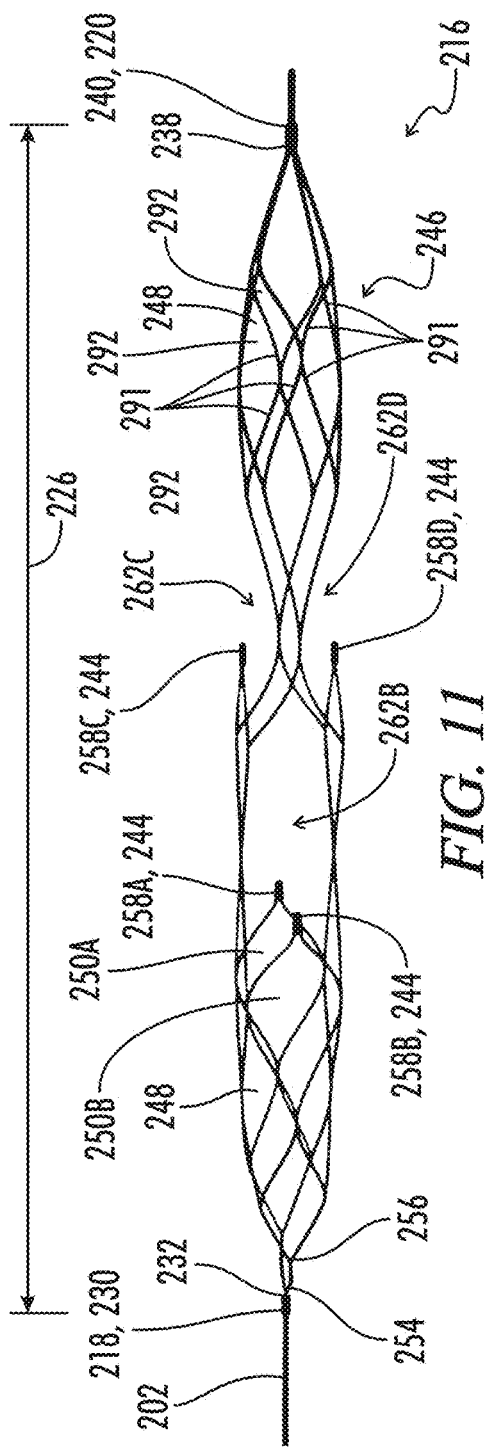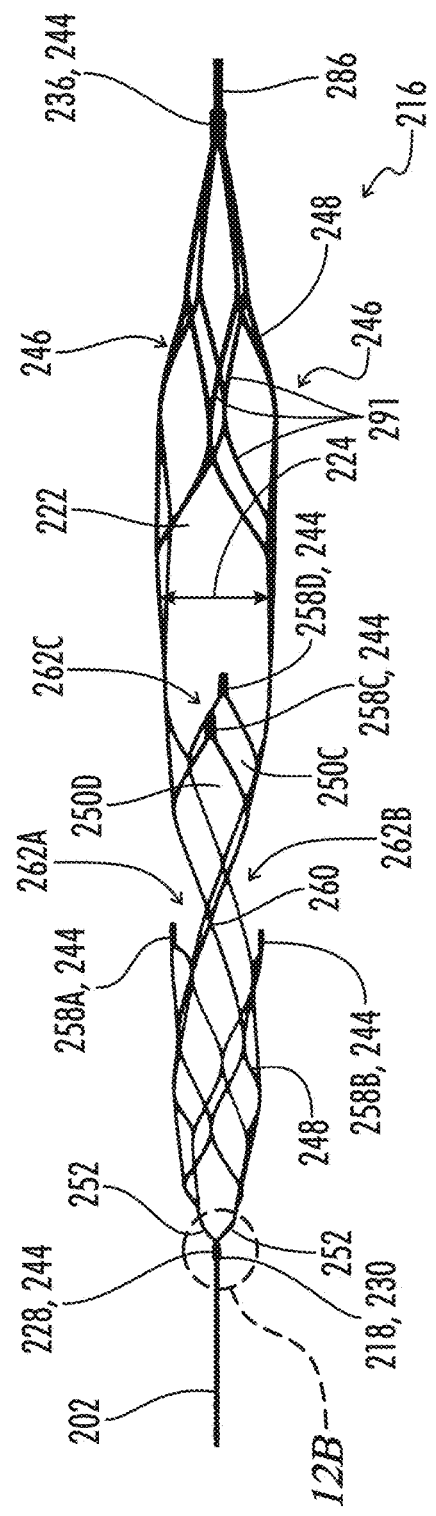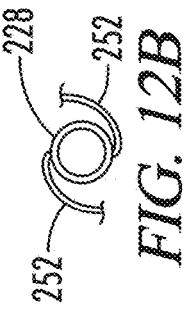

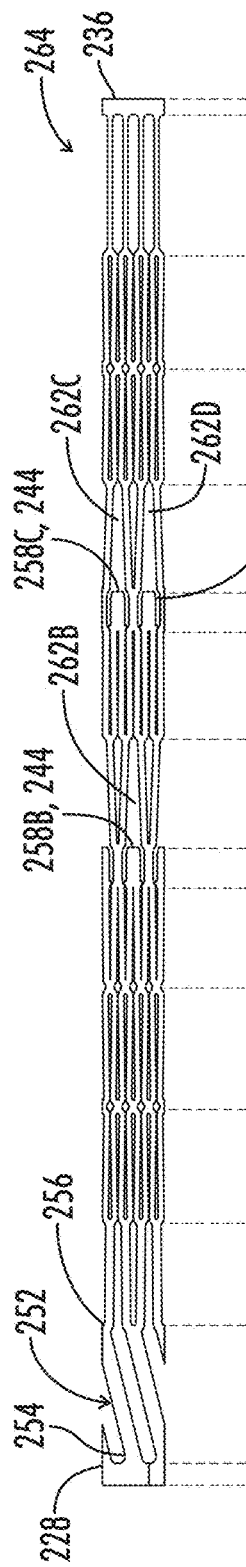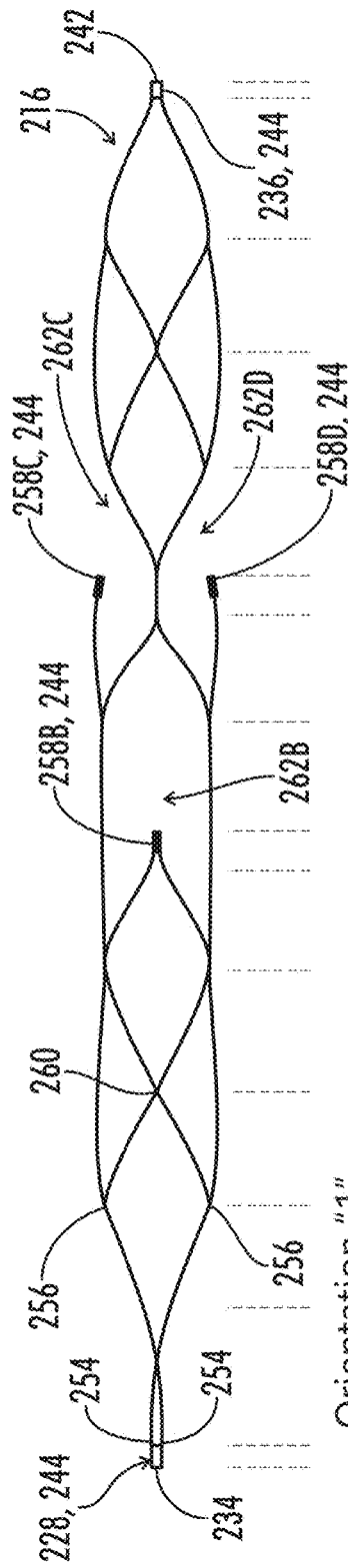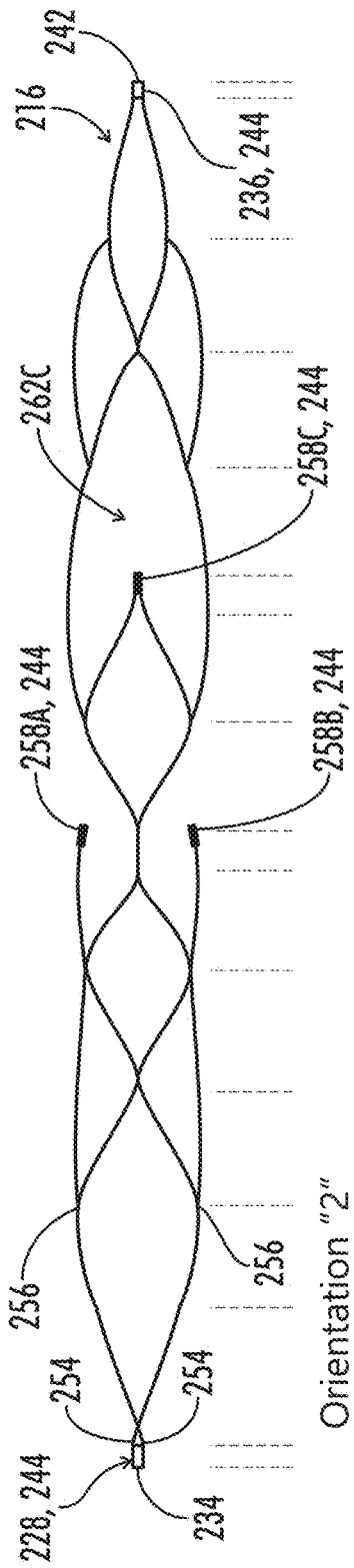

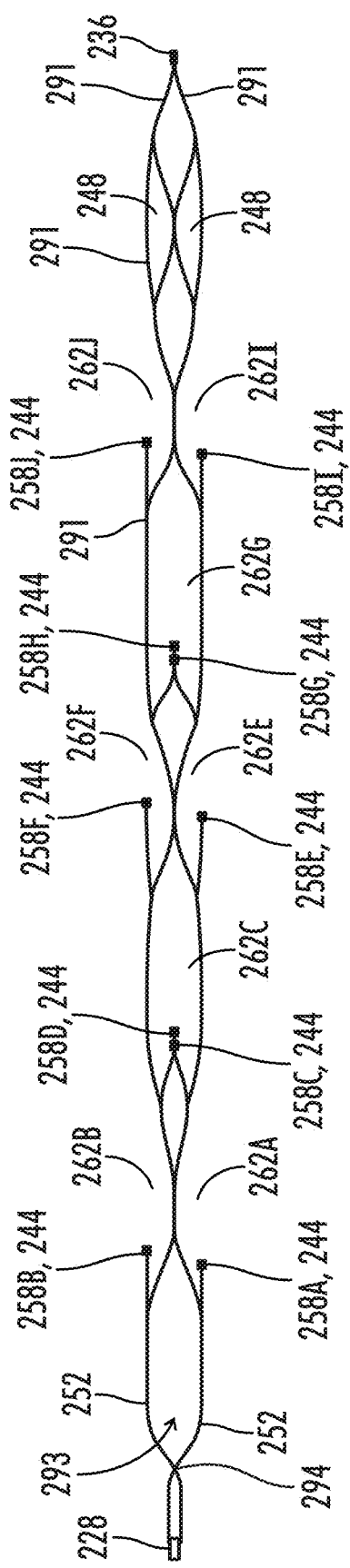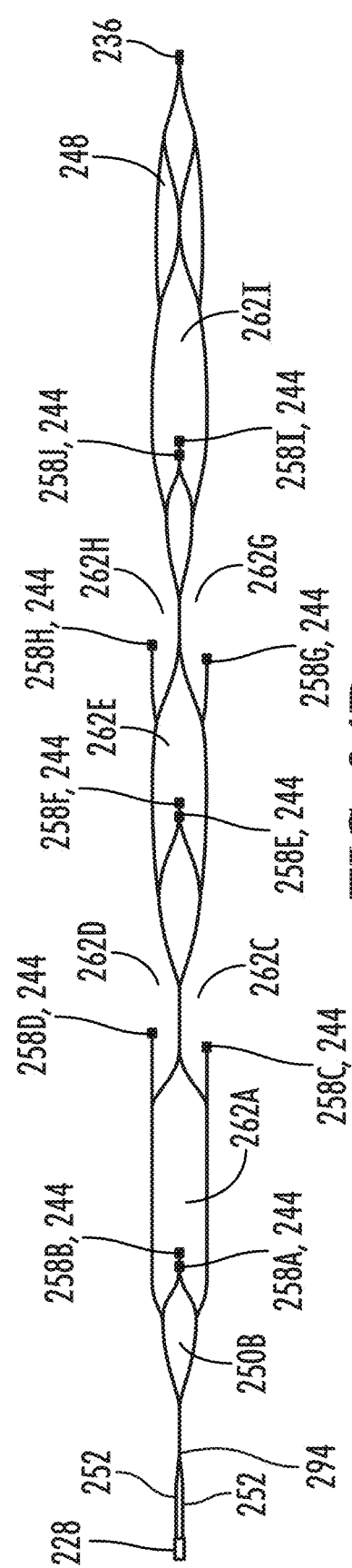

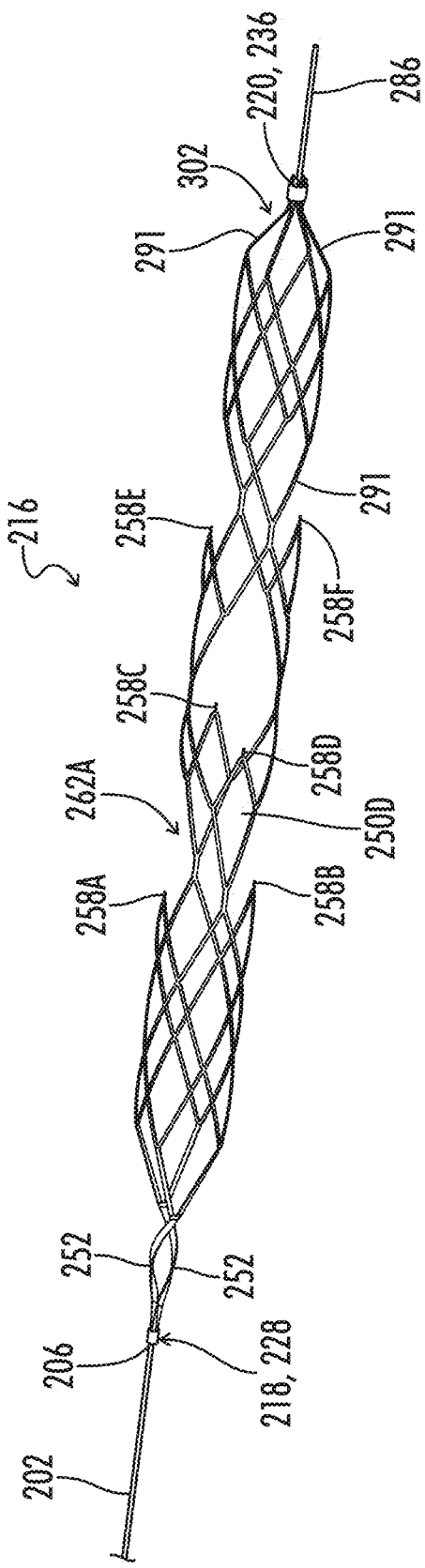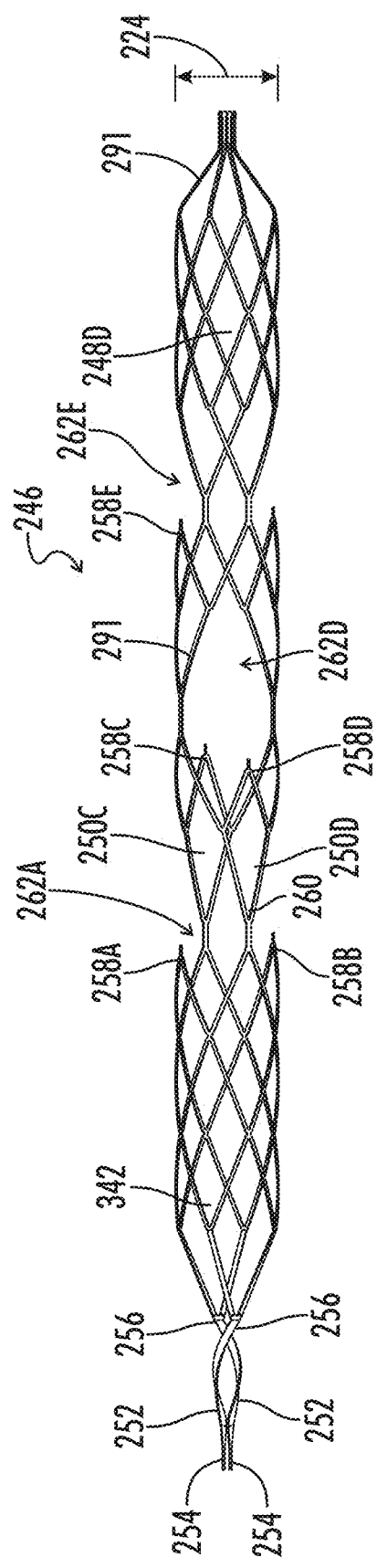
FIG. 36A
FIG. 36B

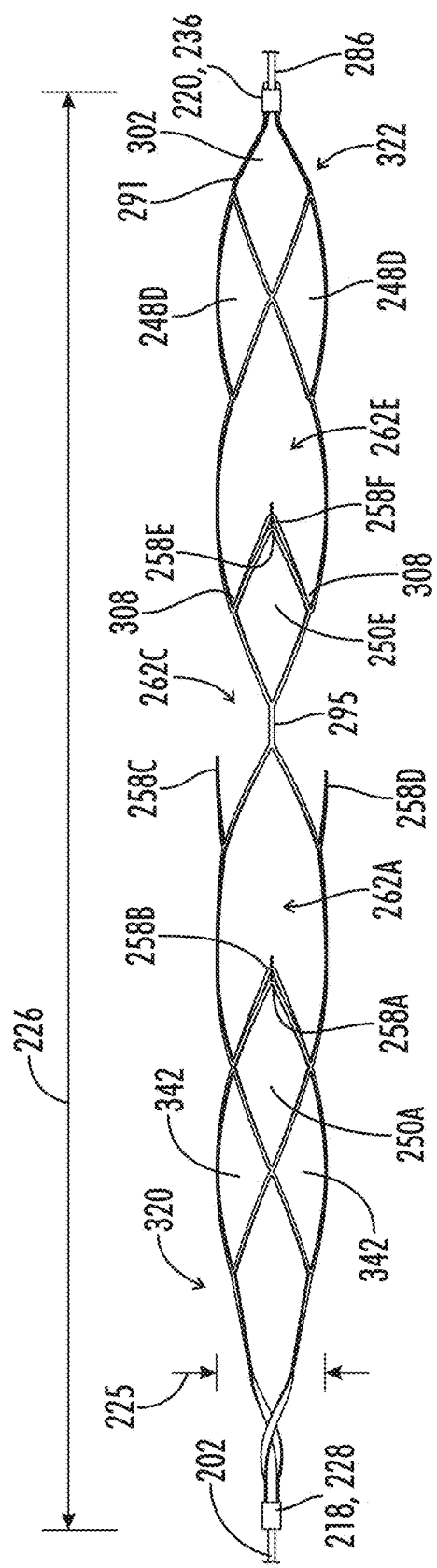
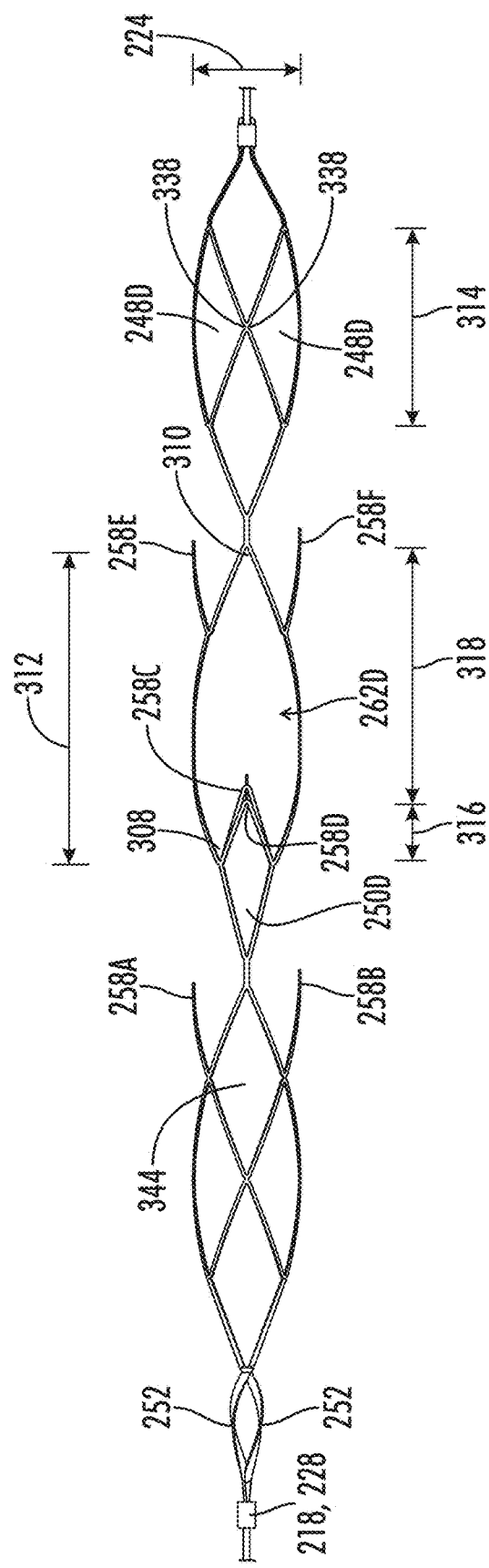
FIG. 36I
FIG. 36J

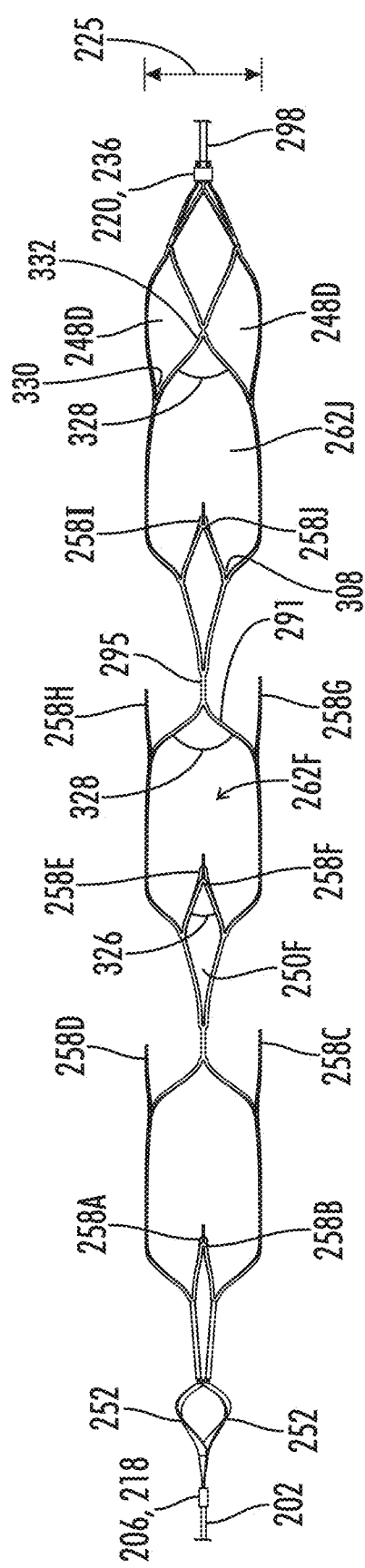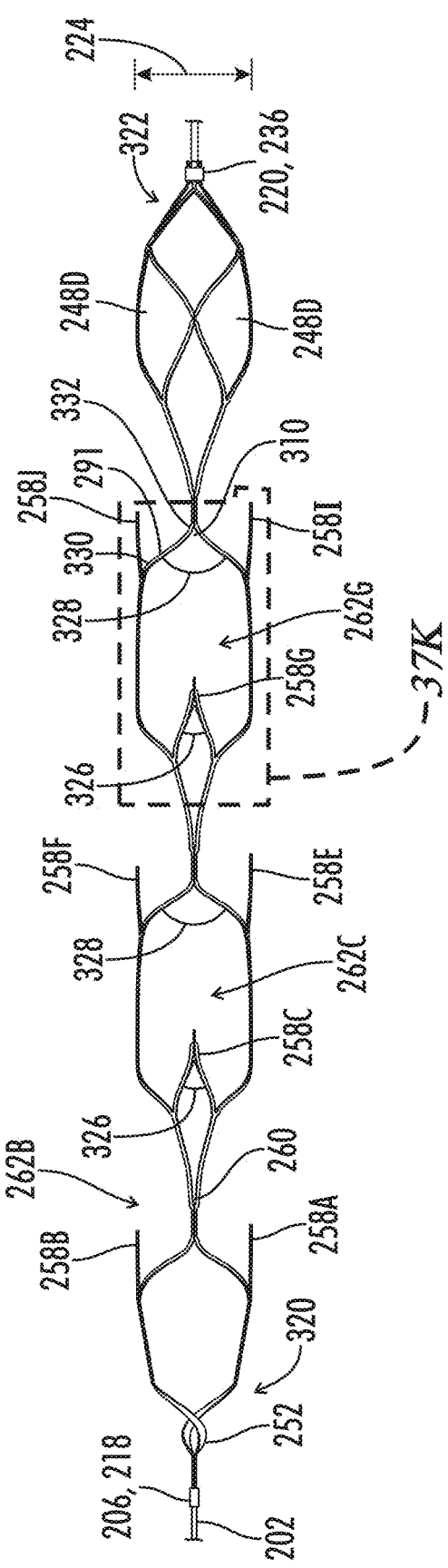
FIG. 37E
FIG. 37F

CLOT RETRIEVAL SYSTEM

RELATED APPLICATIONS

This application is a continuation-in-part of U.S. patent application Ser. No. 16/579,427, filed Sep. 23, 2019 and entitled "CLOT RETRIEVAL SYSTEM", which is a continuation of U.S. patent application Ser. No. 16/385,862, filed Apr. 16, 2019 and entitled "CLOT RETRIEVAL SYSTEM", which is a continuation-in-part of U.S. patent application Ser. No. 15/947,955, filed Apr. 9, 2018 and entitled "CLOT RETRIEVAL SYSTEM", which is a continuation-in-part of U.S. patent application Ser. No. 14/794,783, filed Jul. 8, 2015 and entitled "Clot Retrieval System", which is a continuation-in-part of U.S. patent application Ser. No. 14/558,712, filed Dec. 2, 2014 and entitled "CLOT RETRIEVAL SYSTEM, which is a continuation of U.S. patent application Ser. No. 14/558,705, filed Dec. 2, 2014 and entitled "CLOT RETRIEVAL SYSTEM", which is a continuation-in-part of U.S. patent application Ser. No. 14/147,491 (now U.S. Pat. No. 8,900,265), entitled "CLOT RETRIEVAL SYSTEM" and filed Jan. 3, 2014. U.S. patent application Ser. No. 14/558,705 further claims priority under 35 U.S.C. § 119 to U.S. Provisional Patent Application Ser. No. 61/994,934, filed May 18, 2014 and entitled "ARTICULATING CLOT RETRIEVAL SYSTEM". The entire contents of all of the above patent applications are hereby incorporated by reference.

U.S. patent application Ser. No. 14/794,783 is also a continuation-in-part of International Patent Application No. PCT/US15/10178, entitled "CLOT RETRIEVAL SYSTEM" and filed Jan. 5, 2015, which is a continuation-in-part of U.S. patent application Ser. No. 14/558,712, filed Dec. 2, 2014 and entitled "CLOT RETRIEVAL SYSTEM", which is a continuation of U.S. patent application Ser. No. 14/558,705, filed Dec. 2, 2014 and entitled "CLOT RETRIEVAL SYSTEM." U.S. patent application Ser. No. 14/558,705 is a continuation-in-part of U.S. patent application Ser. No. 14/147,491 (now U.S. Pat. No. 8,900,265), entitled "CLOT RETRIEVAL SYSTEM" and filed Jan. 3, 2014, and further claims priority under 35 U.S.C. § 119 to U.S. Provisional Patent Application Ser. No. 61/994,934, filed May 18, 2014 and entitled "ARTICULATING CLOT RETRIEVAL SYSTEM". International Patent Application No. PCT/US15/10178 further claims priority under 35 U.S.C. § 119 to U.S. Patent Application No. 61/994,919, filed May 18, 2014 and entitled "CLOT RETRIEVAL SYSTEM." The entire contents of all of the above patent applications are hereby incorporated by reference.

U.S. patent application Ser. No. 14/794,783 is also a continuation-in-part of International Patent Application No. PCT/US15/31447, entitled "CLOT RETRIEVAL SYSTEM" and filed May 18, 2015. The entire contents of all of the above patent applications are hereby incorporated by reference.

BACKGROUND

Technical Field

The present invention relates to a deployable system for removing a blood clot or other object from a lumen of an animal.

Background of the Invention

Acute ischemic strokes develop when a blood clot (thrombus) blocks an artery supplying blood to the brain. Needless to say, when a blood clot creates such a blockage, time in removing the clot is critical.

The removal of intracranial obstructions is limited by several factors, such as the distance of the intracranial obstruction from the femoral access site, the tortuosity (twists and turns in the artery as it enters the base of the skull) of the cervical and proximal intracranial vasculature, the small size of the vessels and the extremely thin walls of intracranial vessels, which lack a significant muscular layer. These limitations require a device to be small and flexible enough to navigate through tortuous vessels within a guide catheter and microcatheter, expand after delivery at the site of occlusion and be retrievable into the microcatheter and yet be strong enough to dislodge strongly adherent thrombus from the vessel wall. In addition, the device should distally entrap or encase the thrombus to prevent embolization to other vessels and to completely remove the occlusion. The device should be retrievable without the need for proximal occlusion of the vessel, which carries risk of further ischemia and risk of vessel injury. The device should be simple to use and be capable of multi-use within the same patient treatment. The device should not be abrasive and should not have sharp corners exposed to the endothelial layer of the vessel wall.

Currently available intravascular thrombus and foreign body removal devices lack several of these features. Currently available devices include the MERCI™ RETRIEVER clot retriever device marketed by Concentric Medical, Inc. (Mountainview, Calif.), the PENUMBRA™ system marketed by Penumbra Inc. (Alameda, Calif.) to retrieve clots, and the newer stent retrieval devices TREVO™ (Stryker, Kalamazoo, Mich.) and SOLITAIRE™ (eV3 Endovascular Inc., Plymouth, Mass., which is a subsidiary of Covidien). All the devices are ineffectual at removing organized hard thrombus that embolize to the brain from the heart and from atherosclerotic proximal vessels. These "hard" thrombi constitute the majority of strokes which are refractory to medical treatment and are therefore referred for removal by mechanical means through an endovascular approach. The MERCI retrieval system is comprised of coiled spring-like metal and associated suture material. The method of use is deployment distal to the thrombus and by withdrawing the device through the thrombus, the thrombus becomes entangled in the coil and mesh and then is retrieved. The MERCI system requires occlusion of the proximal vessel with a balloon catheter and simultaneous aspiration of blood while the thrombus is being removed. Most of the time, the device fails to dislodge the thrombus from the wall of the vessel and often, even when successfully dislodging the thrombus, the thrombus embolizes into another or the same vessel due to the open ended nature of the device.

The next attempt at a thrombus removal system was the PENUMBRA. The PENUMBRA is a suction catheter with a separator that macerates the thrombus which is then removed by suction. The device is ineffective at removing hard, organized thrombus which has embolized from the heart, cholesterol plaque from proximal feeding arteries and other foreign bodies.

The SOLITAIRE and TREVO systems are self-expanding non-detachable stents. The devices are delivered across the thrombus which is then supposed to become entwined in the mesh of the stent and which is then removed in a manner similar to the MERCI system. Again, these devices are ineffectual at treating hard thrombus. In fact, the thrombus is often compressed against the vessel wall by the stent which temporarily opens the vessel by outwardly pressing the clot against the vessel wall. Upon retrieval of the devices, the clot remains or is broken up into several pieces which embolize to vessels further along the vessel.

Thus, there is a need for new, easy-to-use, easy-to-manufacture, safe surgical devices for removing obstructions, such as blood clots, from internal lumens of humans and other animals in a timely manner.

BRIEF SUMMARY

The present disclosure provides several systems for removing obstructions and other objects within a blood vessel or other lumen of an animal. The system may be deployed in the lumen from a distal end of a catheter and, in some embodiments, includes a pull wire having a proximal end and a distal end; a distal body attached to the pull wire, the distal body comprising an interior, an exterior, a proximal end, a distal end, a plurality of proximal memory metal strips located at the proximal end, a proximal hub/junction located in the distal body interior, and a distal hub/junction located distal relative to the proximal hub/junction. The distal body has a relaxed state wherein the distal body has a first height and width and a collapsed state wherein the distal body has a second height and width, the second height less than said first height, the second width less than the first width. The system further includes a catheter having an interior, a proximal end leading to the interior and a distal end leading to the interior, the catheter comprised of a biocompatible material and configured to envelope the distal body when the distal body is in the collapsed state. Each of the proximal memory metal strips has a proximal end and a distal end and preferably, in the relaxed state, each of the proximal ends of the proximal memory metal strips is located proximal relative to the proximal hub/junction. Preferably, in the relaxed state, the proximal ends of the proximal memory metal strips are configured to move towards each other and towards the pull wire when an operator moves the proximal hub/junction distally and closer to the stationary distal hub/junction (i.e., when the operator decreases the distance between the hubs/junctions). Preferably, in the relaxed state, the proximal ends of the proximal memory metal strips are configured to move away from each other and away from the pull wire by moving the proximal hub/junction proximally away from the stationary distal hub/junction (i.e., when the operator increases the distance between the hubs/junctions).

Optionally, the system further includes a plurality of memory metal connector strips, the plurality of memory metal connector strips each having a proximal end attached to a proximal memory metal strip and a distal end attached to the proximal hub/junction. Optionally, the connector strips are integral with the proximal hub/junction (i.e., optionally, the connector strips and the proximal hub/junction are formed from the same piece of memory metal). Optionally, the proximal hub/junction is a tube having an aperture and the pull wire passes through the aperture. Optionally, in the relaxed state, the proximal hub/junction is slidable along the pull wire (i.e., at least a segment of the pull wire). Optionally, in the relaxed state, the proximal memory metal strips are distributed substantially evenly about a perimeter of the distal body. Optionally, the distal hub/junction is a tube having an aperture. Optionally, the distal hub/junction is attached to the pull wire such that the distal hub/junction is not slidable along the pull wire. Optionally, the distal body further comprises a lead wire extending distally from the distal hub/junction. Optionally, the distal body comprises a basket comprised of a plurality of memory metal strips distal relative to the proximal memory metal strips. Optionally, the distal hub/junction, the proximal hub/junction, and the distal basket are comprised of a nitinol having the same material composition. Optionally, the distal body further comprises an x-ray marker. Optionally, the proximal memory metal strips form a claw, the claw having a closable proximal end formed by the proximal ends of the proximal memory metal strips. Optionally, between 2 and 4 proximal memory metal strips form the claw. Optionally, the distal body, in the relaxed state, has a tapered shape in which the distal body height and width decrease from the proximal end to the distal end. Optionally, the distal body, in the relaxed state, has a bullet shape. Optionally, the proximal hub/junction and the distal hub/junction are generally cylindrical in shape and each has an outer diameter and an inner diameter that forms the apertures of the proximal and distal hub/junctions, the outer diameters of the proximal and distal hub/junctions are substantially the same size, and the inner diameters of the proximal and distal hubs/junctions are substantially the same size. Optionally, the outer diameters of the proximal and distal hubs/junctions are from about 0.011 inches to about 0.054 inches, and the inner diameters of the proximal and distal hubs/junctions are from about 0.008 inches to about 0.051 inches. Optionally, the pull wire is generally cylindrical and the diameter of the pull wire is between about 0.008 inches and about 0.051 inches. Optionally, the proximal memory metal strips have a length of between about 10 and about 60 millimeters. Optionally, the first height and first width of the distal body are between about 2 millimeters (mm) and about 6 millimeters. Optionally, the proximal memory metal strips are configured to a separate a clot from a blood vessel wall.

The present invention also provides a method of removing an object from an interior lumen of an animal, the lumen having an interior wall forming the lumen. In some embodiments, the method includes:

a) providing a system comprising: i) a pull wire having a proximal end and a distal end; ii) a distal body attached to the pull wire, the distal body comprising a proximal end, a distal end, and a claw, the claw comprised of a plurality of memory metal strips, the distal body having a relaxed state wherein the distal body has a first height and width and a collapsed state wherein the distal body has a second height and width, the second height less than said first height, the second width less than said first width; and iii) a catheter having an interior, a proximal end leading to the interior and a distal end leading to the interior, the catheter comprised of a biocompatible material and configured to envelope the distal body when said distal body is in said collapsed state;

b) positioning the system in the lumen;

c) deploying the distal body from the distal end of the catheter;

d) allowing the height and width of said distal body to increase; and e) moving the memory metal strips towards each other and the pull wire so as to capture the obstruction. Optionally, the claw and the memory metal strips are located at the proximal end of said distal body and the distal body is deployed distal to said object. Optionally, the proximal memory metal strips have a proximal end forming the proximal end of the claw and a distal end, and the method includes moving the proximal ends of the memory metal strips towards each other and the pull wire so as to capture the obstruction. Optionally, the distal body further comprises a proximal hub/junction located in the distal body interior, and a distal hub/junction located distal relative to the proximal hub/junction, each of the memory metal strips has a proximal end and a distal end, each of the proximal ends of the memory metal strips is located proximal relative to the proximal hub/junction, and the proximal ends of the memory metal strips are configured to move towards each other and towards the pull wire by moving the proximal hub/junction distally and closer to the distal hub/junction, and the proximal ends of the memory metal strips are configured to move away from each other and away from the pull wire by moving the proximal hub/junction proximally and away from the distal hub/junction, and the method further comprises moving the proximal hub/junction distally and closer to the distal hub/junction so as to capture the obstruction in the claw. Optionally, the interior lumen is an intracranial artery and the obstruction is a blood clot. Optionally, the method further comprises using the clot to move the proximal hub/junction toward the distal hub/junction and exert tension on the proximal memory metal strips. Optionally, the method further comprises using a tube to move the proximal hub/junction toward the distal hub/junction and exert tension on the proximal memory metal strips.

The present invention also provides a method of manufacturing a system for removing objects within an interior lumen of an animal. In some embodiments, the method includes:

a) providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;

b) cutting the wall of the middle portion with a laser;

c) removing the pieces of the middle portion cut by the laser to form a proximal tube, a middle portion comprising a plurality of memory metal strips attached to the proximal tube and a distal tube;

d) altering the shape of the middle portion;

e) allowing the middle portion to expand relative to the distal tube and the proximal tube;

f) cutting the memory metal strips to form a first segment comprising the proximal tube and a proximal segment of the memory metal strips, and a second segment comprising the distal tube and a distal segment of the memory metal strips; and g) joining the proximal segments to the distal segments such that the distal segments form the proximal end of a distal body, such that the proximal tube is located inside an interior of said distal body, and such that the proximal tube is located distal relative to the proximal end.

Optionally, the method further includes placing a pull wire through the proximal tube such that the proximal tube is slidable along at least a segment of the pull wire. Optionally, the method further includes attaching the pull wire to the distal tube. Optionally, the step of joining the proximal segments to the distal segments comprises welding or soldering the proximal segments to the distal segments. Optionally, after the step of joining the proximal segments to the distal segments, the proximal end forms a claw comprised of between 2 and 4 memory metal strips, the claw memory metal strips configured to move towards each by moving said proximal tube distally and closer to the distal tube, and the claw memory metal strips configured to move away from each other by moving the proximal tube proximally and away from said distal tube. Optionally, the method further includes not altering the shape of the proximal and distal portions while altering the shape of the middle portion. Optionally, the method further includes cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches.

In an alternate embodiment, the present disclosure provides a system for removing objects from an interior lumen of an animal that includes:

a pull wire having a proximal end and a distal end;

a distal body attached to the pull wire, the distal body comprising an interior, a proximal end, a distal end, a distal body length extending from the proximal end to the distal end, a proximal hub/junction (preferably in the form of a tube) forming the proximal end of the distal body, a basket comprised of a plurality of cells formed by a plurality of basket strips, a plurality of proximal strips, and, optionally a distal hub/junction (preferably in the form of a tube) forming a distal end of the basket, the basket comprising a basket interior, each proximal strip having a proximal end attached to the proximal hub/junction, and a distal end attached to a cell, the distal body having a relaxed state wherein the distal body has a first height and a first width, and a collapsed state wherein the distal body has a second height and a second width, the second height less than the first height, the second width less than the first width; and a catheter having an interior, a proximal end leading to the interior and a distal end leading to the interior, the catheter comprised of a biocompatible material and configured to envelope the distal body when the distal body is in the collapsed state, wherein, in the relaxed state, the basket comprises a first pair of distal crowns not attached to another cell of the basket and pointing generally in the distal direction, the first pair of distal crowns located approximately the same distance from the proximal hub/junction and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub/junction and further wherein each of the distal crowns in the first and second pair of distal crowns comprises an x-ray marker, the x-ray maker more visible under x-ray as compared to the basket strips when the distal body is located in a cranial blood vessel inside the body of a human and the x-ray is taken from outside the human's body. Optionally, instead of a distal hub/junction, the basket includes an open distal end.

Optionally, the x-ray markers are comprised of a material different than the material forming the basket strips. Optionally, in the relaxed state, the basket interior is substantially hollow. Optionally, in the relaxed state, the distal body does not have another x-ray marker that is located approximately the same distance from the proximal hub/junction as the first pair of x-ray markers and the distal body does not have another x-ray marker that is located approximately the same distance from the proximal hub/junction as the second pair of x-ray markers. In other words, the first and second pair of x-ray markers are the only markers their respective distances from the proximal hub/junction. Optionally, each distal crown in the first and second pair of distal crowns forms part of an enlarged cell and further wherein the surface area of each enlarged cell in the relaxed state is greater than the surface area of each of the other individual cells of the basket and further wherein the enlarged cells are configured to allow a thrombus to pass therethrough and into the basket interior. Optionally, in the relaxed state, the distal body does not have another free distal-pointing crown that is located approximately the same distance from the proximal hub/junction as the first pair of distal crowns and the distal body does not have another free distal-pointing crown that is located approximately the same distance from the proximal hub/junction as the second pair of distal crowns. Optionally, the basket strips are comprised of a memory metal. Optionally, each of the distal crowns in the first pair and second pair of distal crowns curve radially inward toward the basket interior in the relaxed state, wherein the distal crowns of the first pair of distal crowns are configured to contact each other when an exterior, external compressive force (such as a thrombus) is exerted on a distal crown of the first pair of distal crowns when the distal body is in the relaxed state, and further wherein the distal crowns of the second pair of distal crowns are configured to contact each other when an exterior, external compressive force (such as a thrombus) is exerted on a distal crown of the second pair of distal crowns when the distal body is in the relaxed state. Optionally, the proximal hub/junction is located approximately in the center of the first height and first width in the relaxed state. For example, preferably the proximal hub/junction is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub/junction (e.g., within about 0 and about 4 mm of the proximal hub/junction). Optionally, each distal crown forms part of a cell that further comprises a proximal crown pointing generally in the proximal direction and connected to a memory metal strip (e.g., a proximal strip comprised of a memory metal or a basket strip comprised of a memory metal). In other words, the proximal crowns are not free. Optionally, the basket, the proximal hub/junction and the proximal strips are comprised of a memory metal, wherein the proximal hub/junction comprises a proximal end and a distal end, and further wherein the proximal strips are integral with the distal end of the proximal hub/junction. Optionally, the length of the distal body from the proximal hub/junction to the distal hub/junction (not including any lead wire) is from about 20 mm to about 65 mm. Optionally, the system is used in a method of removing a blood clot from a blood vessel of an animal the method comprising the steps of:

a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles. Optionally, at least one x-ray marker attached to the distal crowns is distal to the clot when the distal body is deployed from the distal end of the catheter. Optionally, the method further comprises applying contrast dye proximally and distally to the clot. Optionally, the method further comprises providing a suction catheter having a proximal end and a distal end, and attaching the distal end of the suction catheter to the clot by applying suction to the suction catheter. Optionally, the method further comprises aspirating by hand a pre-determined volume of fluid from the suction catheter using a syringe and then locking the syringe at the pre-determined volume. Optionally, the method further comprises delivering the suction catheter adjacent to the clot by advancing the catheter over the pull wire.

In yet another embodiment, the system includes:

a pull wire having a proximal end and a distal end;
a distal body attached to the pull wire, the distal body comprising an interior, a proximal end, a distal end, a distal body length extending from the proximal end to the distal end, a proximal hub/junction (preferably in the form of a tube) forming the proximal end of the distal body, a basket comprised of a plurality of cells formed by a plurality of basket strips, a plurality of proximal strips, and optionally a distal hub/junction (preferably in the form of a tube) forming a distal end of the basket, the basket comprising a basket interior, each proximal strip having a proximal end attached to the proximal hub/junction, and a distal end attached to a cell, the distal body having a relaxed state wherein the distal body has a first height and a first width, and a collapsed state wherein the distal body has a second height and a second width, the second height less than the first height, the second width less than the first width; and
a catheter having an interior, a proximal end leading to the interior and a distal end leading to the interior, the catheter comprised of a biocompatible material and configured to envelope the distal body when the distal body is in the collapsed state,
wherein, in the relaxed state, the basket comprises a first pair of distal crowns not attached to another cell of the basket and pointing generally in the distal direction, the first pair of distal crowns located approximately the same distance from the proximal hub/junction and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub/junction, wherein each distal crown of the first and second pair of distal crowns form a cell, each cell further comprising a proximal crown pointing generally in the proximal direction and connected to a memory metal strip, wherein each of the distal crowns in the first pair and second pair of distal crowns curve radially inward toward the basket interior in the relaxed state, wherein the distal crowns of the first pair of distal crowns are configured to contact each other when an exterior, external compressive force (e.g., a thrombus) is exerted on a distal crown of the first pair of distal crowns when the distal body is in the relaxed state, and further wherein the distal crowns of the second pair of distal crowns are configured to contact each other when an exterior, external compressive force (e.g., a thrombus) is exerted on a distal crown of the second pair of distal crowns when the distal body is in the relaxed state. When it is said that a proximal crown pointing generally in the proximal direction and is connected to a memory metal strip, it is meant that the proximal crown is either connected to a basket strip or a proximal strip comprised of a memory metal (e.g., nitinol). Optionally, instead of a distal hub/junction, the basket includes an open distal end.

Optionally, the proximal hub/junction is located approximately in the center of the first height and first width in the relaxed state. For example, preferably the proximal hub/junction is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, in the relaxed state, the basket interior is substantially hollow. Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub/junction (e.g., within about 0 mm and about 4 mm of the proximal hub/junction). Optionally, each distal crown in the first and second pair of distal crowns forms part of an enlarged cell and further wherein the surface area of each enlarged cell in the relaxed state is at least twice as large as the surface area of each other individual cell of the basket and further wherein the enlarged cells are configured to allow a thrombus to pass therethrough and into the basket interior. Optionally, the pull wire is attached to the proximal hub/junction. Optionally, the basket, the proximal hub/junction and the proximal strips are comprised of a memory metal, wherein the proximal hub/junction comprises a proximal end and a distal end, and further wherein the proximal strips are integral with the distal end of the proximal hub/junction. Optionally, the distal body further comprises a lead wire extending distally from the distal hub/junction, the lead wire having a length of from about 3 mm to about 10 mm. Optionally, the distal hub/junction, the proximal hub/junction, and the basket are comprised of a nitinol having the same material composition and further wherein the proximal and the distal hubs/junctions are tubular and generally cylindrical in shape and each has an outer diameter and an inner diameter, the inner diameter forming apertures of the proximal and distal hubs/junctions and further wherein the outer diameters of the proximal and distal hubs/junctions are substantially the same size and further wherein the inner diameters of the proximal and distal hubs/junctions are substantially the same size. Optionally, the length of the distal body from the proximal hub/junction to the distal hub/junction (not including any lead wire) is from about 20 mm to about 65 mm.

Optionally, the system is used in a method of removing a blood clot from a blood vessel of an animal the method comprising the steps of:
a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles.

In still further embodiments, the present disclosure provides yet another embodiment of a system for removing objects from an interior lumen of an animal. The system may include a pull wire having a proximal end and a distal end. The system may also include a distal body attached to the pull wire (e.g., the distal end of the pull wire). The distal body may include an interior, a perimeter, a proximal end, a distal end, a distal body length extending from the proximal end to the distal end, a proximal junction forming the proximal end of the distal body, a plurality of proximal strips, a basket comprised of a plurality of cells formed by a plurality of basket strips, and a distal junction forming a distal end of the basket. The basket may include a basket interior. Each proximal strip may have a distal end attached to a cell and a proximal end, and the proximal ends of the proximal strips may converge at the proximal junction. The distal body may have a relaxed state wherein the distal body has a first height and a first width, and a collapsed state wherein the distal body has a second height and a second width, the second height less than the first height, the second width less than the first width. Optionally, in the relaxed state, the basket comprises a series of at least three pair of cells located on the distal body perimeter having a proximal crown pointing generally in the proximal direction and attached to a memory metal strip and a free distal crown pointing generally in the distal direction. Optionally, in the series, the proximal-most free distal crowns are located at the 12 and 6 o'clock positions and located about the same distance (i.e., the same distance+/−5 millimeters (mm)) from the proximal junction, the next proximal-most free distal crowns are located at the 3 and 9 o'clock positions and located about the same distance (i.e., the same distance+/−5 mm) from the proximal junction, and the succeeding proximal-most free distal crowns are located at the 12 and 6 o'clock positions and located about the same distance (i.e., the same distance+/−5 mm) from the proximal junction. Each free distal crown may form part of a different enlarged cell that is configured to allow a thrombus to enter the basket interior. Optionally, in the relaxed state, the basket comprises a plurality of distal cells distal to the distal-most free distal crowns of the series. The plurality of distal cells may have a proximal crown attached to another cell of the basket and pointing generally in the proximal direction and a distal crown pointing generally in the distal direction and attached to the distal junction. Optionally, each enlarged cell has a proximal end, a distal end comprising a distal crown pointing generally in the distal direction, and a length extending from the proximal end to the distal end of the respective enlarged cell. Optionally, in the relaxed state, each distal cell has a length extending from the proximal crown to the distal crown of the respective distal cell. Optionally, in the relaxed state, each of the enlarged cells is longer than each of the distal cells. Optionally, for some, most or each of the enlarged cells, the distance from the proximal end of the enlarged cell to the free distal crown of the enlarged cell is less than the distance from the free distal crown of the enlarged cell to the distal end of the enlarged cell. Optionally, in the relaxed state, the basket does not have any free crowns that point generally in the proximal direction. Optionally, the distal body, in the relaxed state, comprises a distal tapered region in which the distal body height and width decrease as the basket approaches the distal junction. Optionally, each of the enlarged cells is longer than each of the pair of cells in the series. Optionally, in the relaxed state, each of the enlarged cells extends from the 6 o'clock position to the 12 o'clock position or the 3 o'clock position to the 9 o'clock position. Optionally, in the relaxed state, the basket further comprises a plurality of proximal cells proximal to the proximal-most free distal crowns of the series. Optionally, the plurality of proximal cells have a proximal crown attached to the proximal junction and pointing generally in the proximal direction and a distal crown pointing generally in the distal direction and attached to another cell of the basket. Optionally, the proximal crowns of the cells comprising the proximal-most free distal crowns are attached to the distal ends of the proximal strips. Optionally, in the relaxed state, for each of the enlarged cells, two basket strips meet to form the distal crown located at the distal end of the enlarged cell. Optionally, each basket strip has a basket strip proximal end, a basket strip distal end, and a basket strip length extending from the proximal end to the distal end. Optionally, for at least some, most, or each of the enlarged cells, the maximum angle between the two basket strips at the same location along the distal body length is at least 90 degrees. Optionally, in the relaxed state, for said at least some, most or each of the enlarged cells, two basket strips meet to form the free distal crowns of the enlarged cell, wherein each basket strip has a basket strip proximal end, a basket strip distal end, and a basket strip length extending from the proximal end to the distal end, and further wherein the maximum angle between the two basket strips at the same location along the distal body length is no more than 40 degrees. Optionally, for at least some, most or each of the enlarged cells, the average angle between the two basket strips is at least 90 degrees. Optionally, for at least some, most or each of the enlarged cells, each of the basket strip lengths are approximately equal to ½ of the distal body height and width. Optionally, from at least the proximal crowns of the cells comprising the next proximal-most free distal crowns to the proximal ends of the enlarged cells formed by the succeeding free distal crowns, the basket has no cells other than the enlarged cells and the cells comprising the free distal crowns. Optionally, from at least the proximal-most free distal crowns to the proximal ends of the enlarged cells formed by the succeeding free distal crowns, the basket has no cells other than the enlarged cells and the cells comprising the free distal crowns. Optionally, the distal crowns of the enlarged cells are attached to another cell of the basket. Optionally, in the relaxed state, the basket further comprises an additional pair of cells located about the same distance (i.e., the same distance+/−5 mm) from the proximal junction as the cells comprising the proximal-most pair of free distal crowns and located at the 9 and 3 o'clock positions. Optionally, each cell of the additional pair of cells having a proximal crown attached to a memory metal strip and a distal crown attached to another cell of the basket. Optionally, the additional pair of cells adjoin the enlarged cells formed by the proximal-most free distal crowns. Optionally, from at least the distal crowns of the additional pair of cells to the proximal ends of the enlarged cells formed by the succeeding free distal crowns, the basket has no cells other than the enlarged cells, the cells comprising the free distal crowns and the additional pair of cells. Optionally, in the relaxed state, the basket comprises a series of bridge memory metal strips having a proximal end attached to a distal crown of a cell and a distal end attached to a proximal crown of a distally-located cell. Optionally, a proximal pair of bridge memory metal strips are located at the 3 and 9 o'clock positions. Optionally, a more distally-located pair of bridge memory metal strips are located at the 12 and 6 o'clock positions. Optionally, each of the pair of bridge memory metal strips forms part of at least one enlarged cell. Optionally, the bridge memory metal strips are the sole distally-extending basket strips attached to the respective proximal crowns and the sole proximally-extending basket strips attached to the respective distal crowns. Optionally, in the relaxed state, each of the pair of bridge memory metal strips forms part of two enlarged cells. Optionally, the bridge memory metal strips are substantially parallel to the distal body length. Optionally, the plurality of distal cells is comprised of four cells located about the same distance (i.e., the same distance+/−5 mm) from the proximal junction. Optionally, each cell has a center, and the centers of the cells are spaced at approximately 90 degree intervals about the distal body perimeter. Optionally, each of said four cells adjoins two of the other of said four cells. Optionally, each of said four cells comprises two lateral crowns pointing generally in a direction perpendicular to the distal body length and further wherein each lateral crown of one of said four cells adjoins a lateral crown of an adjacent one of said four cells. Optionally, the distal body has no more than four cells at any location along the distal body length. Optionally, each of the enlarged cells are approximately the same size. Optionally, in the relaxed state, the basket interior is substantially hollow. Optionally, the basket comprises a series of at least five pairs of cells located on the distal body perimeter having a proximal crown pointing generally in the proximal direction and attached to a memory metal strip and a free distal crown pointing generally in the distal direction, wherein in the series, the next proximal-most free distal crowns after the succeeding free distal crowns are located at the 3 and 9 o'clock positions and located about the same distance (the same distance+/−5 mm) from the proximal junction, and the distal-most free distal crowns are located at the 12 and 6 o'clock positions and located about the same distance (the same distance+/−5 mm) from the proximal junction. Optionally, the enlarged cells formed by the proximal-most free distal crowns are adjoining, the enlarged cells formed by the next proximal-most free distal crowns are adjoining and the enlarged cells formed by the succeeding free distal crowns are adjoining. Optionally, each of the enlarged cells formed by the next proximal-most free distal crowns adjoins an enlarged cell formed by a proximal-most free distal crown and an enlarged cell formed by a succeeding free distal crown. Optionally, the distal body further comprises a lead wire extending distally from the distal junction. Optionally, the system further comprises a catheter having an interior, a proximal end leading to the interior and a distal end leading to the interior, the catheter comprised of a biocompatible material and configured to envelop the distal body when the distal body is in the collapsed state. Optionally, for each enlarged cell, the free distal crown is aligned with the distal crown located at the distal end of the enlarged cell. Optionally, the distal body, in the relaxed state comprises a proximal tapered region in which the distal body height and width decrease as the proximal strips approach the proximal junction. Optionally, the system is used in a method of removing a blood clot from a blood vessel of an animal that includes: a) providing the system; b) positioning the system in the blood vessel; c) allowing the height and width of the distal body to increase; d) moving the blood clot into the basket interior; and e) moving the distal body proximally out of the blood vessel.

Optionally, instead of three pair of cells in the series, the series may include only two pair of cells located on the distal body perimeter having a proximal crown pointing generally in the proximal direction and attached to a memory metal strip and a free distal crown pointing generally in the distal direction, and, in the series, the proximal-most free distal crowns may be located at the 12 and 6 o'clock positions and located about the same distance (the same distance+/−5 mm) from the proximal junction, and the next proximal-most free distal crowns may be located at the 3 and 9 o'clock positions and located about the same distance (the same distance+/−5 mm) from the proximal junction. In such embodiment, the distal body and system may have any feature mentioned above in connection with the distal body having at least three pairs of cells with free distal crowns.

BRIEF DESCRIPTION OF THE DRAWINGS

FIG. 2A illustrates a side, elevation view of the memory metal tube of FIG. 1B after being cut by a laser; in FIG. 2A, the tube is shown as though it were flat for purposes of illustrating the cut pattern only.

FIG. 2B illustrates a side, perspective view of the memory metal tube of FIG. 1B after being cut by a laser.

FIG. 2C illustrates another side, perspective view of the memory metal tube of FIG. 1B after being cut by a laser; in FIG. 2C, the tube is rotated as compared to FIG. 2B.

FIGS. 3A-3H illustrate a method of manufacturing a distal body of one embodiment of the present invention using the laser cut memory metal tube of FIGS. 1 and 2; in FIGS. 3A-3H, the basket portion of the distal body is not shown for simplicity of illustration.

in FIGS. 4A-4D, the basket portion of the distal body is not shown for simplicity of illustration.

in FIG. 8, the basket portion of the distal body is not shown for simplicity of illustration.

in FIG. 9, the basket portion of the distal body is not shown for simplicity of illustration.

in FIG. 10, the basket portion of the distal body is not shown for simplicity of illustration.

FIG. 11 illustrates a first, perspective view of a distal body of an alternate embodiment of the present invention; the distal body is in what is referred to herein as "Orientation 1".

FIG. 12A illustrates a second, perspective view of the distal body of FIG. 11; the distal body is in what is referred to herein as "Orientation 2".

FIG. 12B illustrates a proximal, elevation view of the proximal strips of the distal body of FIG. 11.

FIG. 14A illustrates a native memory metal tube used to manufacture the distal body of FIG. 11; the native tube has been rolled out flat and the lines in the tube indicate where the tube has been cut by a laser.

FIG. 14B illustrates a first, perspective view of the distal body manufactured from the native tube of FIG. 14A; the distal body is in Orientation 1.

FIG. 14C illustrates a second, perspective view of the distal body manufactured from the native tube of FIG. 14A; the distal body is in Orientation 2.

in FIG. 26, the user has locked the syringe lever at the desired volume.

in FIG. 27, the suction catheter has partially sucked the distal body and clot into the suction catheter.

in FIG. 28, the suction catheter has completely sucked the distal body and clot into the suction catheter.

in FIG. 33B, the distal body is in Orientation 1.

in FIG. 33C, the distal body is in Orientation 2.

FIG. 34A illustrates a first, perspective view of a distal body of another embodiment of the present invention; in FIG. 34A, the distal body is in Orientation 1.

FIG. 34B illustrates a second, perspective view of the distal body of FIG. 34A; in FIG. 34B, the distal body is in Orientation 2.

in FIG. 35A, the distal body is in Orientation 1.

in FIG. 35B, the distal body is in Orientation 2.

FIG. 36A illustrates a front perspective view of a distal body of another embodiment of the present invention; in FIG. 36A, the distal body is in the relaxed state.

FIG. 36B illustrates another front perspective view of the distal body of FIG. 36A without the proximal and distal hubs/junctions and pull wire.

FIG. 36I illustrates a top plan view of the distal body of FIG. 36A.

FIG. 36J illustrates a front elevation view of the distal body of FIG. 36A.

in FIG. 36M, the miniature clock faces illustrate the 12, 3, 6 and 9 o'clock positions.

in FIG. 36N, the miniature clock faces illustrate the 12, 3, 6 and 9 o'clock positions.

in FIG. 37A, the distal body is in the relaxed state.

FIG. 37E illustrates a bottom plan view of the distal body of FIG. 37A.

FIG. 37F illustrates a rear elevation view of the distal body of FIG. 37A.

in FIG. 37H, the miniature clock faces illustrate the 12, 3, 6 and 9 o'clock positions.

in FIG. 37I, the miniature clock faces illustrate the 12, 3, 6 and 9 o'clock positions.

DETAILED DESCRIPTION

Figure 1A:
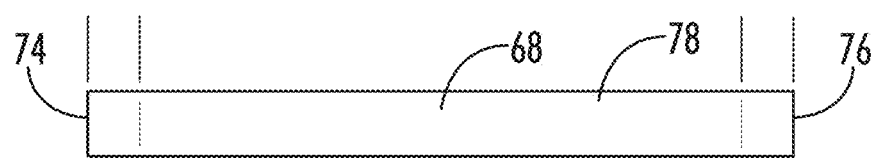
FIG. 1A illustrates a side, elevation view of a memory metal tube prior to being cut by a laser.

With reference to FIGS. 1-10, the present disclosure provides a deployable system, generally designated by the numeral 10, for removing an obstruction such as a blood clot 12 or other object from a blood vessel 14 or other interior lumen of an animal. In addition to a blood clot 12, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

Referring further to FIGS. 1-10, the deployable system 10 includes a pull wire 16 that has a proximal end (not shown) and a distal end 20. Optionally, the diameter of the pull wire is between about 0.008 inches and about 0.051 inches. Preferably, the pull wire 16 is comprised of a biocompatible metallic material.

The system 10 further includes a distal body 22, which is attached to the pull wire 16. The distal body 22 has a proximal end 24, a distal end 26, an interior 28, and an exterior 30. The distal body 22 has a collapsed state, wherein the distal body 22 has a first height and width and is configured to fit into a catheter 50 (see FIG. 10A), and a relaxed state wherein the distal body 22 has a different height 32 and width and is configured to expand to about the height and width of a human blood vessel 14 when the distal body 22 is deployed from the catheter 50 (see FIGS. 10B-G). The distal body 22 further includes a proximal hub/junction 74 and a distal hub/junction 76 that is located distal relative to the proximal hub/junction 74. In some embodiments, the distal body 22 includes a plurality of strips 40 comprised of a memory metal (e.g., a memory metal alloy such as nitinol) that form the proximal end 24 of the distal body 22. Optionally, the proximal memory metal strips 40 each have a distal end 44 and a proximal end 42 that forms an openable and closable claw 46. Optionally, the proximal memory metal strips 40 are attached to the proximal hub/junction 74 through connector memory metal strips 48. In such embodiments, the proximal hub/junction 74 may be slidable along at least a segment of the pull wire 16, in contrast to the distal hub/junction 76, which is optionally fixed to the pull wire 16 and not slidable along the pull wire 16. Moving the proximal hub/junction 74 distally and closer to the distal hub/junction 76 (i.e., shortening the distance 88 between the proximal hub/junction 74 and distal hub/junction 76 by moving the proximal hub/junction 74 distally while keeping the distal hub/junction 76 stationary) exerts tension on the connector memory metal strips 48 and, in turn, the proximal memory metal strips 40. This tension, in turn, causes the proximal ends 42 of the proximal memory metal strips 40 to move radially toward each other and the pull wire 16. As the proximal ends 42 of the proximal memory metal strips 40 move radially toward each other and the pull wire 16, the claw 46 (formed by the proximal memory metal strips 40) is brought from the open position to at least a partially closed position, which in turn, separates the obstruction 12 from the wall of the human lumen 14 and captures the obstruction 12. See FIG. 3H, FIG. 8, FIG. 9F, and FIGS. 10F and 10G. Conversely, preferably, movement of the proximal hub/junction 74 proximally and away from the distal hub/junction 76 (i.e., increasing the distance 88 between the hubs/junctions 74 and 76) releases the tension in the proximal memory metal strips 40, which in turn, causes the proximal ends 42 of the proximal memory metal strips 40 to move away from each other and the pull wire 16, opening the claw 46. The claw 46 and proximal hub/junction 74 form several functions. First, as described, closing of the claw 46 captures the obstruction 12. Second, closing the claw 46 retracts the claw 46 from the wall of the lumen 14 so that the claw 46 does not scrape against (and damage) the lumen wall while capturing the obstruction 12. Third, closing the claw 46 reduces the height and width of the distal body 22, which allows the distal body 22 to be re-sheathed in the catheter 50, which may be desired, for example, if the operator seeks to re-deploy the distal body 22 in another location in the body (which may be the case if the operator originally deploys the distal body 22 in the wrong location in the lumen 14). For purposes of the present invention, "closing the claw" embraces both partially closing the claw 46 (where the proximal ends 42 of the proximal memory metal strips 40 do not contact the pull wire 16) and fully closing the claw 46 (where the proximal ends 42 contact the pull wire 16).

The claw 46 may be comprised of any number of proximal memory metal strips 40. Preferably, however, between 2 and 4 proximal memory metal strips 40 comprise the claw 46 (it being understood that the connector strips 48, if present, merely serve to tether the claw 46 to the proximal hub/junction 74). Preferably, the proximal memory metal strips 40 have a length of between about 10 and about 60 millimeters. The proximal memory metal strips 40 can be thought of as arms of the claw 46.

In some embodiments, the connector strips 48 are integral with the proximal hub/junction 74 (i.e., formed from the same piece of memory metal). In other embodiments, the proximal hub/junction 74 may be welded or soldered to the connector strips 48. Optionally, in the relaxed state, the proximal memory metal strips 42 are distributed substantially evenly about a perimeter of the distal body 22.

Optionally, the distal body 22 includes a lead wire 52 extending distally from the distal body 22. Optionally, the lead wire 52 extends distally from the distal hub/junction 76. If present, the lead wire 52 may be used to facilitate movement of the system 10 in the lumen 14.

Optionally, the distal body 22 includes a basket 54 distal to the proximal memory metal strips 40, the basket 54 comprised of a plurality of memory metal strips 56 distal relative to the proximal memory metal strips 40. The distal memory metal strips 56 may, for example, form a basket 54 with a plurality of mesh openings 58. Optionally, the size of the mesh openings 58 in the basket 54 when the distal body 22 is in its relaxed state is less (preferably significantly less)

than the diameter of an average-sized ischemic blood clot 12 so that the blood clot 12 does not escape from the distal basket 54 after being captured by the distal body 22. Optionally, the basket 54 has an open proximal end 60 and a substantially closed distal end 62, which is formed by a distal tube 76. Optionally, the distal and proximal hubs/junctions 74 and 76 and the distal basket 54 are comprised of a nitinol having the same material composition. Optionally, the size of the mesh openings 58 decreases from the proximal end 60 of the basket 54 to the distal end 62. The distal basket 54 is best seen in FIG. 2 and can be comprised of a different number of cell patterns. The distal basket 54 is not shown in FIGS. 3-10 for ease of illustrating the other components in the system 10.

Optionally, the proximal hub/junction 74 and the distal hub/junction 76 are cylindrical tubes comprising substantially circular apertures that span the length of the hubs/junctions 74 and 76 and the hubs/junctions 74 and 76 have approximately the same inner diameter 72 and the same outer diameter 70. Preferably, the inner diameter 72 is at least slightly larger than the diameter of the pull wire 16 so that the pull wire 16 can slide through the proximal hub/junction 74. In some embodiments, the outer diameters 70 of the proximal and distal hubs/junctions 74 and 76 may be from about 0.011 inches to about 0.054 inches and the inner diameters 72 of the proximal and distal hubs/junctions 74 and 76 may be from about 0.008 inches to about 0.051 inches.

Optionally, the distal body 22 further comprises an x-ray marker 64 that is more visible under x-ray as compared to the proximal memory metal strips 40 when the distal body 22 is located in a cranial blood vessel inside the body of a human and the x-ray is taken from outside the human's body. If the connector strips 48 are welded or soldered to the proximal memory metal strips 40, the x-ray markers 64 may be, for example, located at the welding or soldering site. In some cases, the increased thickness at the welding or soldering site may in of itself comprise the x-ray marker 64. Preferably, the x-ray marker 64 is comprised of a radiopaque material. Some examples of radiopaque materials can include, but are not limited to, gold, platinum, palladium, tantalum, tungsten alloy, polymer material loaded with radiopaque filler, and the like. Preferably, the proximal memory metal strips 40 are comprised of nitinol and the x-ray marker 64 is comprised of a material having a density greater than the nitinol.

A catheter 50 with an open proximal end (not shown) and an open distal end 66 initially envelopes the system 10. As used herein, the term "catheter" generally refers to any suitable tube through which the system 10 can be deployed. Preferably, the catheter 50 is sterile and comprised of a biocompatible material (i.e., a material that does not irritate the human body during the course of a 45 minute operation that involves using the system 10 to remove a clot 12 from an intracranial blood vessel 14). The catheter 50 can be any suitable shape, including but not limited to generally cylindrical. Preferably, the catheter 50 is a microcatheter. For purposes of the present invention, when it is said that the catheter 50 envelopes the system 10, it will be understood that the catheter 50 envelopes at least one component of the system 10 (preferably, the distal body 22, the lead wire 52, and the pull wire 16). In some embodiments, the catheter 50 is about 2.5 French in diameter. Optionally, the catheter 50 is delivered to the region of the lumen 14 that has the obstruction 12 as follows: a guide wire is delivered to the obstruction region past the obstruction 12; the catheter 50 is delivered over the guide wire; the guide wire is removed; and the system 10 is delivered with its pull wire 16 and lead wire 52 through the catheter 50. Optionally, the pull wire 16 is used to push the system 10 through the catheter 50 as well as to retrieve the distal body 22 after capturing the obstruction 14 as described below. The system 10 may utilize a plurality of catheters 50, such as, for example, a wider catheter that travels to the brain and a very flexible, smaller diameter microcatheter that is delivered from the first catheter and travels through the small arteries of the brain. Preferably, the catheter 50 is comprised of a biocompatible, polymeric material (i.e., one or more polymeric materials such as silicone, PVC, latex rubber or braided nylon).

Optionally, in the relaxed, opened-claw state, the distal body 22 or optionally just the distal basket 54 has a tapered shape (e.g., substantially conical or bullet in shape) so that the distal body 22 or just the distal basket 54 tapers from the distal body 22 or the distal basket's 54 proximal end to the distal end.

The proximal end of the system 10 is shown at the left end of FIGS. 1 and 3-10 and the distal end of the system 10 is shown at the right end of FIGS. 1 and 3-10 because a principal use of the system 10 is to remove a blood clot 12 from a human intracranial artery 14, in which case the system 10 generally will enter the artery 14 at its proximal end by the surgeon entering the patient's body near the groin and pushing the catheter 50 towards the brain. The diameter of human arteries 14 generally decrease from their proximal end to their distal end. However, when used in other types of lumens, the distal body 22 may be located proximally relative to the catheter 50 as the term proximally and distally are used in that lumen.

The surgeon may deploy the distal body 22 by, for example, moving the catheter 50 proximally so as to unsheathe the distal body 22 or by pushing the distal body 22 out of the catheter 50.

Use of the system 10 will now be described to remove a blood clot 12 from an intracranial artery 14 of a human ischemic stroke patient, however, it will be appreciated that the system 10 may be used to remove other objects from other interior lumens.

A catheter 50, which contains the collapsed distal body 22 is positioned in the lumen 14 distal to the clot 12. See FIG. 10A.

The distal body 22 is deployed from the catheter 50 and the height and width of the distal body 22 expand to about the height and width of the blood vessel 14. See FIG. 10B.

The catheter 50 is pulled proximally and a claw-actuator tube 90 is deployed into the blood vessel 14. See FIG. 10C.

The distal body 22 is moved proximally so that the clot 12 is located in the interior 28 of the distal body 22. See FIGS. 10D and 10E.

The claw-actuator tube 90 is moved distally, which pushes the proximal hub/junction 74 distally so that the distance 88 between the proximal hub/junction 74 and the distal hub/junction 76 (which is fixed to the pull wire 16 and kept stationary) decreases. Distal movement of the proximal hub/junction 74 exerts tension on the connector and proximal memory metal strips 40 and 48, which in turn, closes the claw 46. See FIG. 10F. (The claw actuator tube 90 should float on the pull wire 16—i.e., have an aperture extending the tube's length that has a diameter larger than the diameter of the pull wire 16—and the aperture of the claw actuator tube 90 should be smaller than the diameter of the proximal hub/junction 74 so that the claw actuator tube 90 pushes the proximal hub/junction 74).

The system 10 is withdrawn proximally and removed from the body. See FIG. 10G.

To test the efficacy of the system 10, a distal body 22 with a distal basket 54, proximal and distal hubs/junctions 74 and 76, and a claw 46 comprised of three proximal memory metal strips 42 was tested in a flow model that included a tube and a moist cotton ball located in the tube. The cotton ball was used to simulate a blood clot. The system 10 was deployed distal to the cotton ball. The claw 46 was closed by moving the proximal hub/junction 74 distally to capture the cotton ball. The system 10 and cotton ball were withdrawn proximally in the tube.

Figure 1B:
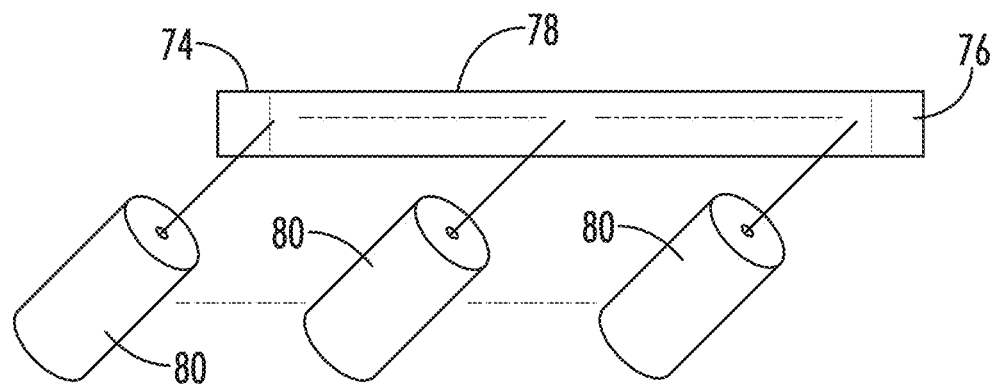
FIG. 1B illustrates a side, elevation view of the memory metal tube of FIG. 1A being cut by a laser.
Figure 4A:
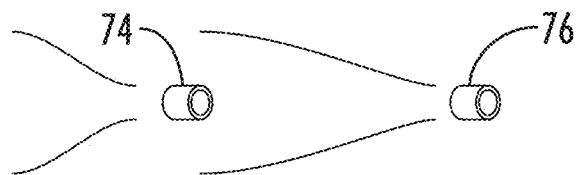
FIGS. 4A-4D illustrate the welding steps of the method of manufacturing shown in FIG. 3.
Figure 4B:
Figure 4C:
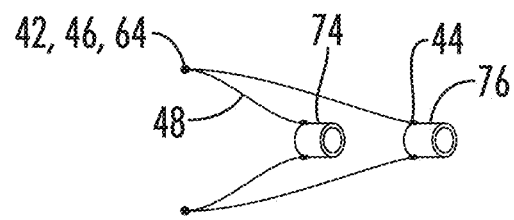
Figure 4D:
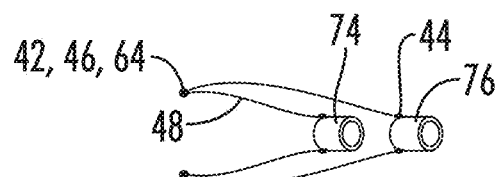
Figure 5:
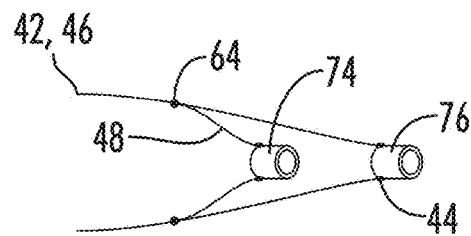
FIGS. 5 and 6 illustrate different locations that connector strips may be welded to the proximal memory metal strips.
Figure 6:
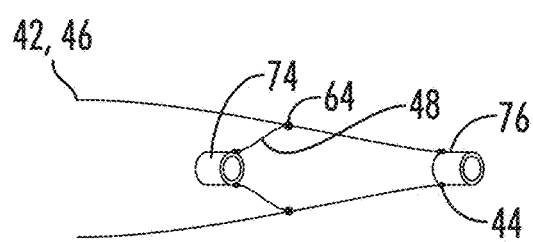
Figure 7:
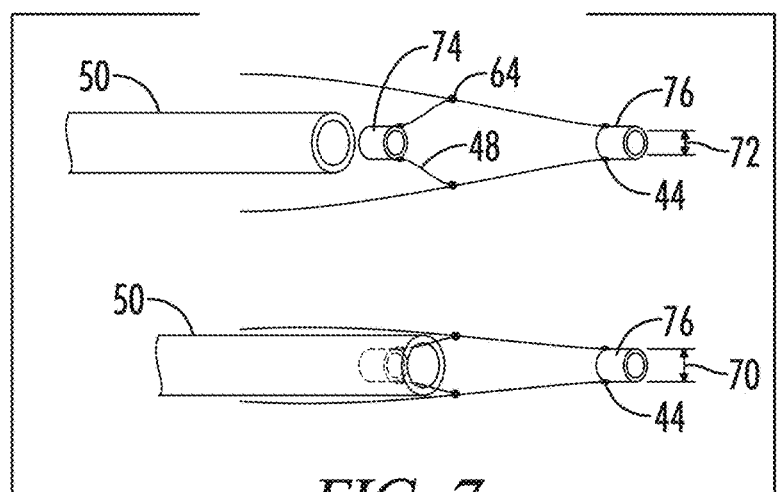
FIG. 7 illustrates a side, elevation view of a catheter and the distal body of FIG. 6.
Figure 8:
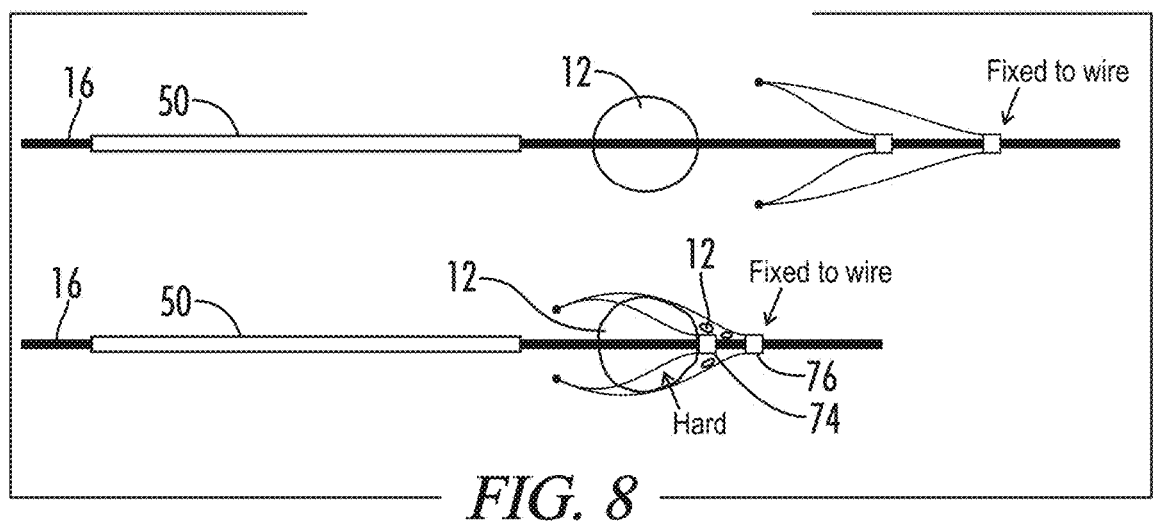
FIG. 8 illustrates a side, elevation view of a deployable system of one embodiment of the present invention being used to capture a blood clot.
Figure 9:
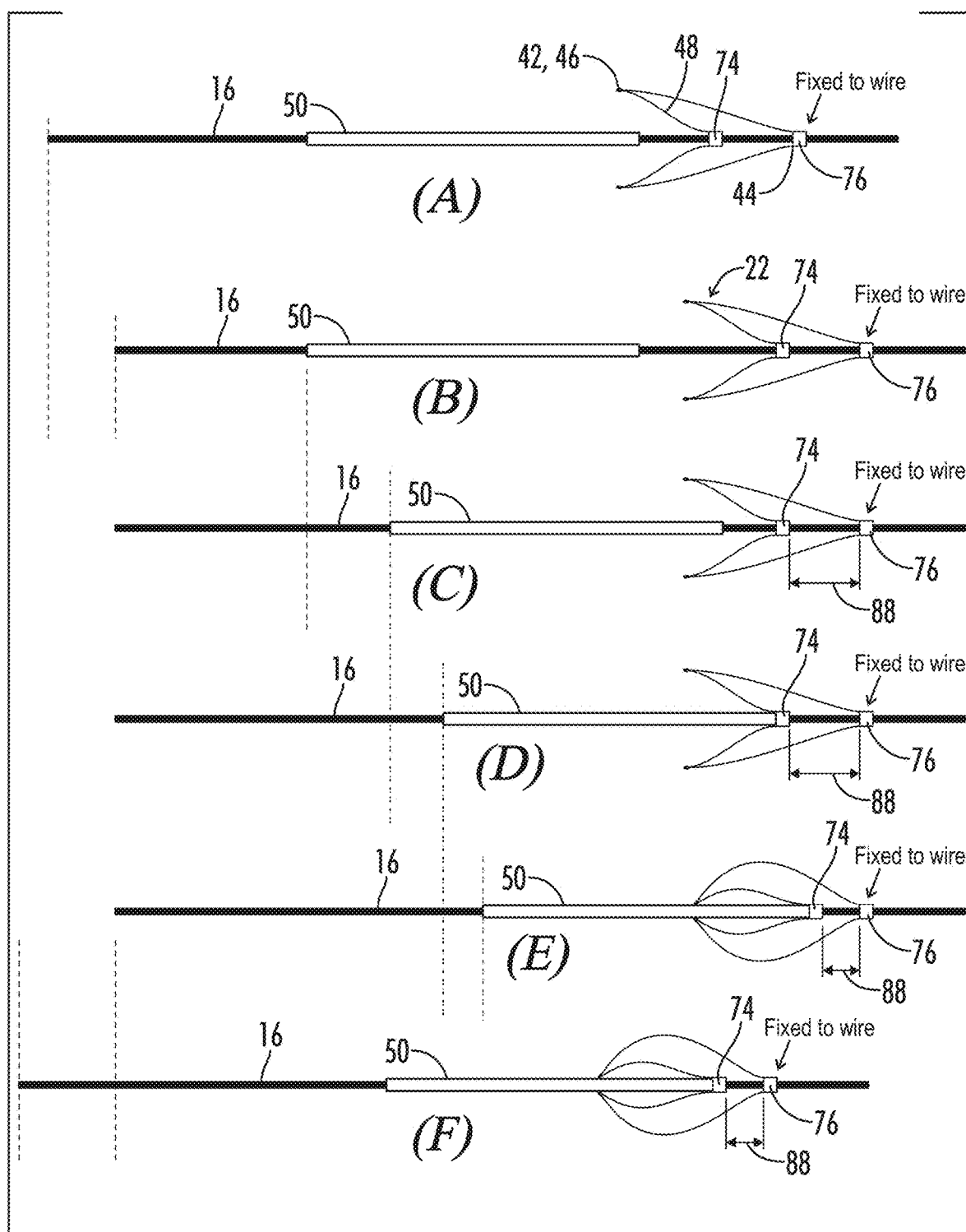
FIG. 9 illustrates a side, elevation view of a claw of one embodiment of the present invention being closed by a claw actuator tube.
Figure 10:
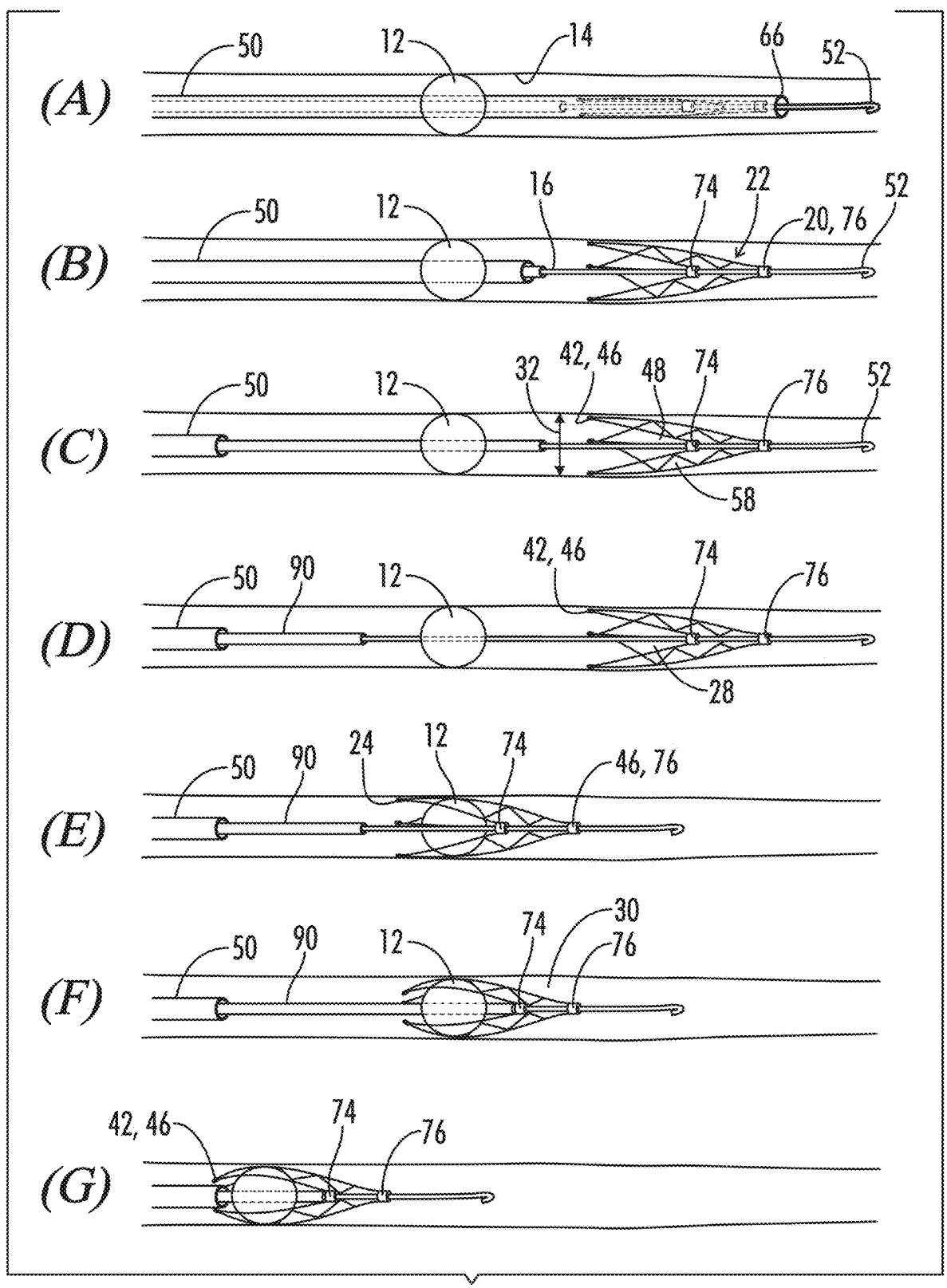
FIG. 10 illustrates a side, elevation view of a deployable system of one embodiment of the present invention being used to capture a blood clot.

In some embodiments, the distal body 22 is prepared by a process that includes one or more of the following steps, as illustrated in FIGS. 1-4 a) providing a single tube 68 comprised of a memory metal such as nitinol, the single tube 68 having an exterior, a substantially hollow interior, a wall separating the exterior from the substantially hollow interior, an open proximal end 74, an open distal end 76, a middle portion 78 between the open proximal end 74 and the open distal end 76 (see FIG. 1A);

b) cutting the wall of the middle portion 78 with a laser 80 (see FIG. 1B);

c) removing the pieces of the middle portion 78 cut by the laser 80 to form a proximal tube 74, a distal tube 76 and a middle portion 78 comprising a plurality of memory metal strips 82 attached to the proximal tube 74;

d) altering the shape of the middle portion 78 using a mandrel and allowing the middle portion 78 to expand relative to the distal tube 76 and proximal tube 74 to form the distal basket 54;

e) quenching the middle portion 78 at room temperature;

f) removing the mandrel from the middle portion 78 (see FIGS. 2 and 3A);

g) mechanically or chemically electropolishing the middle portion 78 to remove oxides;

h) cutting the memory metal strips 82 to form a first segment 84 comprising the proximal tube 74 and a proximal segment of the memory metal strips 82 and a second segment 86 comprising the distal tube 76 and a distal segment of the memory metal strips 82 (see FIG. 3B); and i) joining the proximal segments to the distal segments such that the distal segments form the proximal end 24 of the distal body 22, such that the proximal tube 74 is located inside the interior 28 of the distal body 22, and such the proximal tube 74 is located distal relative to the distal body proximal end 24 (see FIGS. 3C-3E).

In some embodiments, the method further includes placing the pull wire 16 through the proximal tube 74 so that the proximal tube 74 is slidable along at least a segment of the pull wire 16.

In some embodiments, the method further includes attaching the pull wire 16 to the distal tube 76 so that the distal tube 76 is not slidable along the pull wire 16 but instead the distal tube 76 moves with the pull wire 16.

In some embodiments, after step i, the proximal end 24 of the distal body 22 forms a claw 46 comprised of between 2 to 4 proximal memory metal strips 40, the claw proximal memory metal strips 40 configured to move towards each other and the pull wire 16 by moving the proximal tube 74 distally and toward the distal tube 76 (i.e., decreasing the distance 88 between the tubes 74 and 76) and the claw memory metal strips 40 configured to move away from each other and away from the pull wire (i.e., increasing the distance 88 between the tubes 74 and 76) by moving the proximal tube 76 proximally and away from the distal tube 76 (as described previously).

In some embodiments, the middle portion 78 is expanded by heating the mandrel and the middle portion 78 by, for example, placing the mandrel and the middle portion 78 in a fluidized sand bath at about 500° C. for about 3 to about 7 minutes. As the middle portion 78 is heated, the heating causes the crystalline structure of the memory metal tube 68 to realign. Preferably, the mandrel is tapered (e.g., substantially conical or bullet in shape) so that the distal basket 54 formed from the middle portion 78 tapers from the proximal end 60 to the distal end 62. Preferably, the proximal and distal ends of the tube 74 and 76 are not shape set by the mandrel and are not cut by the laser 80 so that the proximal and distal ends 74 and 76 do not change in shape and only slightly expand in size under heating and return to the size of the native tube 68 after the heat is removed. Preferably, the laser cuts are programmed via a computer. To ensure that the laser cuts only one surface of the tube wall at the time (and not the surface directly opposite the desired cutting surface), the laser 80 is preferably focused between the inner and outer diameter of the desired cutting surface and a coolant is passed through the memory metal tube 68 so that the laser 80 cools before reaching the surface directly opposite the desired cutting surface.

The portions of the wall not cut by the laser 80 create the distal basket 53, proximal and distal tubes 74 and 76, and memory metal strips 40, 48 and 56, as described.

Preferably, the memory metal selected for the native tube 68 has a heat of transformation below average human body temperature (37° C.) so that the distal body 22 has sufficient spring and flexibility after deployment from the catheter 50 in the human blood vessel 14.

In some embodiments, the native tube 68 (and hence the distal and proximal tubes 74 and 76) have an outer diameter of less than about 4 French, e.g., a diameter of about 1 to about 4 French. In some embodiments, the diameter of the pull wire 16 is between about 0.008 inches and about 0.051, as noted above, and in such embodiments, the diameter of the pull wire 16 may be approximately equal to the inner diameter 72 of the native nitinol tube 68.

Without being bound by any particular theory, it is believed that manufacturing the distal body 22 from a single memory metal tube 68 provides ease of manufacturing and safety from mechanical failure and provides tensile strength necessary for the system 10 to remove hard thrombus 12 and other obstructions.

The Embodiments of FIGS. 11-29

FIGS. 11-29 illustrate an alternate embodiment 200 that includes one or more of the following additional features, as described below: twisting proximal strips/tethers 252, unattached/free distal-pointing crowns 258 that optionally curve inward and have x-ray markers 244, and enlarged openings/drop zones 262 in the basket 246 immediately distal to the unattached, distal-pointing crowns 258 that allow the obstruction or other object 270 to enter the distal basket interior 222.

More specifically, as shown in FIGS. 11-29, the system 200 may include a pull wire 202 having a proximal end 204 and a distal end 206, as described above, a distal body 216 attached to the pull wire 202, the distal body 216 comprising an interior 222, a proximal end 218, a distal end 220, a distal body length 226 extending from the proximal end 218 to the distal end 220, a distal body height 224, a proximal hub/junction 228 (preferably in the form of a tube and which has a proximal end 230 and a distal end 232) forming the proximal end 218 of the distal body 216, a basket 246 comprised of a plurality of cells/openings 248 formed by a plurality of basket strips 291 that preferably are comprised of a memory metal, optionally a distal hub/junction 236 that forms the distal end of the basket 246 (preferably in the form of a tube that has a proximal end 238 and a distal end 240), and a plurality of proximal strips 252 (preferably the proximal strips 252 are comprised of a memory metal), each proximal strip 252 having a proximal end 254 attached to the proximal hub/junction/tube 228, and a distal end 256 attached to a cell 248 (more specifically a proximal-pointing crown of a cell 248 located at the proximal end of the basket 246), the basket comprising a basket interior 292, the distal body 216 having a relaxed state wherein the distal body 216 has a first height and width, a collapsed state wherein the distal body 216 has a second height and width, the second height less than the first height, the second width less than the first width; and a delivery catheter 208 for delivering the distal body 216, as described above, having an interior 210, a proximal end 212 leading to the interior 210 and a distal end 214 leading to the interior 210, the delivery catheter 208 comprised of a biocompatible (preferably polymeric) material and configured to envelope the distal body 216 when the distal body 216 is in the collapsed state. Optionally, the basket interior 292 is substantially hollow—i.e., unlike U.S. Patent Publication No. 2013/0345739, the basket interior 292 does not contain an inner elongate body. Optionally, instead of a distal hub/junction 236, the basket 246 includes an open distal end. Optionally, at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246. In other words, the distal crowns 258 of at least two cells 250 are free floating and are not attached to any strip except for the strips forming part of the at least two cells 250; such distal crowns 258 are referred to below as unattached, distal-pointing crowns 258. Preferably, the distal tips of the unattached, distal-pointing crowns 258 terminate at an x-ray marker 244. (Cells labeled with the numerals 250, 250A, 250B, 250C, and 250D refer to the at least two cells that include a proximal crown 260 pointing generally in the proximal direction and an unattached, distal-pointing crown 258, cells labeled with the numerals 262, 262A, 262B, 262C, and 262D refer to the enlarged cells/drop zones adjacent to (preferably immediately distal to) an unattached, distal-pointing crown 258, and cells designated with numeral 248 refer to generally the cells of the basket 246). (When it is said that the enlarged cells/drop zones 262 are preferably immediately distal to an unattached, distal-pointing crown 258, it will be understood that at least a portion of an enlarged cell/drop zone 262 is immediately distal to an unattached, distal-pointing crown 258, and that a portion of the enlarged cell/drop zone 262 may be proximal to an unattached, distal-pointing crown 258, as shown in FIGS. 11-12 due to the shape of the enlarged cells/drop zones 262). It will be understood that part number 250 refers generally to one or more of the at least two cells, whereas part numbers 250A, 250B, 250C, and 250D refer to a specific one of the at least two cells. Similarly, it will be understood that part number 262 refers generally to one or more of the enlarged cells/drop zones, whereas part numbers 262A, 262B, 262C, and 262D refer to a specific one of the enlarged cells/drop zones. Similarly, it will be understood that part number 258 refers generally to one or more of the unattached, distal-pointing crowns, whereas part numbers 258A, 258B, 258C, and 258D refer to a specific one of the unattached, distal-pointing crowns.

Optionally, at least two of the unattached, distal-pointing crowns 258 are located approximately 180 degrees (e.g., about 150 to about 180 degrees) relative to each other and approximately the same distance from the proximal hub/junction/tube 228, as best seen in FIG. 12A. Optionally, the basket 246 comprises a first pair of unattached, distal-pointing crowns 258A and 258B, each of the first pair of unattached, distal-pointing crowns 258A and 258B is located approximately the same distance from the proximal hub/junction/tube 228 and approximately 180 degrees relative to each other, and the basket 246 further comprises a second pair of unattached, distal-pointing crowns 258C and 258D located distally relative to, and approximately 90 degrees (e.g., between about 60 and about 90 degrees) relative to, the first pair of unattached, distal-pointing crowns 258A and 258B. Optionally, the second pair of unattached, distal-pointing crowns 258C and 258D form cells 250C and 250D that are adjacent to, but offset from, the cells 250A and 250B formed by the first pair of unattached, distal-pointing crowns 258A and 258B. (In other words, optionally, the center of cell 250A is about 90 degrees relative to the centers of cells 250C and 250D and optionally the center of cell 250B is also about 90 degrees relative to the centers of cells 250C and 250D). Optionally, at least one of (and preferably all) the unattached, distal-pointing crowns 258A, 258B, 258C or 258D comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the x-ray markers 244 comprise a heavy metal welded or soldered to the unattached, distal-pointing crowns 258. Optionally, the unattached, distal-pointing crowns 258 curve subtly towards the interior 222 of the distal basket 246, which decreases the likelihood that the unattached, distal-pointing crowns 258 will rub against and damage the vessel wall 268. Optionally, the basket 246 comprises at least two cells proximal to the at least two cells 250 that include the unattached, distal-pointing crowns 258. Optionally, the unattached, distal-pointing distal crowns 258 are located about at least 5 mm (e.g., about 5 to about 30 mm) from the proximal hub/junction/tube 228. Optionally, the unattached, distal-pointing crowns 258 are located at least about 5 mm from the distal hub/junction/tube 236. Optionally, the unattached, distal-pointing crowns 258 of the at least two cells 250 also each form part (namely a portion of the proximal boundary) of an enlarged cell 262 (which is the entry point of hard thrombus 270B into the basket interior 222) and further wherein the surface area of the enlarged cells 262 in the relaxed state is greater than the surface area of the other cells of the basket 246 in the relaxed state. Optionally, the unattached, distal-pointing crowns 258 serve several functions: 1) they form flex points of the basket 246, which makes it easier for the system 200 to navigate the curves of the blood vessels 266 of the brains; 2) through the use of x-ray markers 244 on the unattached, distal-pointing crowns 258, they allow the operator to locate the enlarged cells 262 of the basket 246 that form the point at which hard thrombuses 270B enter the basket 246; and 3) they allow the operator to ratchet or force the object 270 into the basket 246 by moving the unattached, distal-pointing crowns 258 proximally and distally relative to the object 270. (As explained below, the numeral 270 refers to clots/thrombuses and other objects generally, and 270A refers to a soft clot, 270B refers to a hard clot and 270C refers to a deformable, cohesive, adherent clot). Optionally, the proximal end 254 of a proximal strip 252 is located about 65-180 degrees (preferably approximately 180 degrees) relative to the distal end 256 of the same proximal strip 252, as best seen in FIG. 12B. In other words, preferably the proximal end 254 of a first proximal strip 252 is attached to the 12 o'clock position on the proximal tube 228 and the distal end 256 of the first proximal strip 252 (which terminates at a proximal cell 248 of the basket 246) is located at the 6 o'clock position (i.e., 180 degrees from the start position), and the proximal end 254 of a second proximal strip 252 is attached to the 6 o'clock position on the proximal tube 228 and the distal end 254 (which terminates at a cell 248 of the basket 246) of the second proximal strip 252 is located at the 12 o'clock position (i.e., 180 degrees from the start position). This twisting feature serves two functions: 1) it allows the proximal strips 252 to surround the object 270; and 2) it allows the manufacturer to insert a mandrel into the basket 246 during the shape-setting procedure. Optionally, the pull wire 202 is attached to the proximal tube 228 (e.g., by gluing, welding, soldering or the like). Preferably, the pull wire 202 does not extend through the distal basket interior 222. Optionally, the proximal strips 252 are integral with the distal end 232 of the proximal tube 228 and the entire distal body 216 is created from a single tube 264 of a memory metal. Optionally, the proximal crowns 260 of the at least two cells 250 that include the unattached, distal pointing-crowns 258 are each attached to another cell 248 of the basket 246. In other words, preferably the basket 246 does not have any free-floating proximal-pointing crowns, as free-floating proximal-pointing crowns could damage the vessel 266 when the distal body 216 is pulled proximally. Optionally, the system 200 further comprises a lead wire 286 extending distally from the distal tube 236, the lead wire 286 having a length of from about 3 mm to about 10 mm. Optionally, the distal hub/junction/tube 236, the proximal hub/junction/tube 228, and the basket 246 are comprised of a nitinol having the same material composition. In other words, as with the prior embodiment of FIGS. 1-10, optionally the entire distal body 216 is manufactured from a single tube of nitinol 264. Optionally, the proximal and distal hubs/junctions/tubes 228 and 236 comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the proximal and distal hubs/junctions/tube interiors 234 and 242 may comprise tantalum welded or otherwise attached to the interior 234 and 242 of the proximal and distal hubs/junctions/tubes 228 and 236. Optionally, the proximal and the distal tubes 228 and 236 are generally cylindrical in shape and each has an outer diameter and an inner diameter, the inner diameter forming apertures of the proximal and distal tubes 228 and 236 and further wherein the outer diameters of the proximal and distal tubes 228 and 236 are substantially the same size and further wherein the inner diameters of the proximal and distal tubes 228 and 236 are substantially the same size. Optionally, the outer diameters of the proximal and distal tubes 228 and 236 are from about 0.011 inches to about 0.054 inches, and further wherein the inner diameters of the proximal and distal tubes 228 and 236 are from about 0.008 inches to about 0.051 inches. Optionally, the pull wire 202 is generally cylindrical and further wherein the diameter of the pull wire 202 is between about 0.008 inches and about 0.051 inches. Optionally, the distal body 216 has a length of between about 10 and about 60 millimeters. Optionally, the first height 224 and first width 226 of the distal body 216 are between about 2 millimeters and about 6 millimeters.

The present disclosure also provides a method of removing a clot or other object 270 from an interior lumen 266 of an animal, the method comprising the steps of:

a) providing the system 200 of FIGS. 11-29, wherein at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246 (i.e., free-floating), and further wherein at least one of the unattached, distal-pointing crowns 258 comprises an x-ray marker 244;

b) positioning the system 200 in the lumen 266;

c) deploying the distal body 216 from the distal end 214 of the delivery catheter 208;

d) allowing the height and width 224 and 226 of the distal body 216 to increase;

e) irradiating the x-ray marker 244 with x-ray radiation and f) moving the object 270 into the distal basket interior 222.

Optionally, the object 270 enters the distal basket interior 222 adjacent to (preferably adjacent and immediately distal to) at least one of the unattached, distal-pointing crowns 258—i.e., in the enlarged cells/drop zones 262. In some embodiments, the distal body 216 is deployed so that at least one (e.g., preferably the two proximal 258A and 258B) of the unattached, distal-pointing crowns 258 is distal to the object 270. As explained below, the x-ray markers 244 of the unattached, distal-pointing crowns 258 are used to locate the distal body 216 relative to the clot or other object 270. It will be appreciated that clots 270 can generally be located in blood vessels 266 by injecting a contrast dye, for example, into the blood vessel 266 proximal and distal to the believed area of obstruction and viewing on an x-ray where the fluid stops moving in the blood vessel 266. It will also be appreciated that if the object 270 is not a blood clot but is a radio-opaque object, the object 270 may be viewed on an x-ray.

Figure 30:
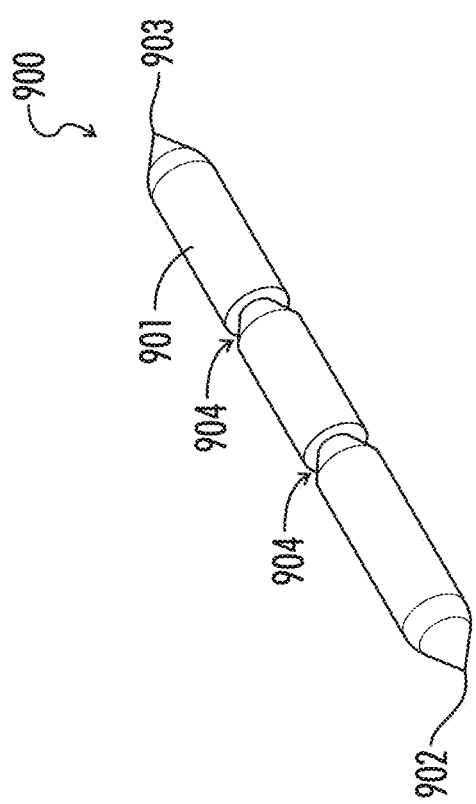
FIG. 30 illustrates a right side perspective view of a mandrel used to prepare unattached distal-pointing crowns that curve radially toward the basket interior.
Figure 31:
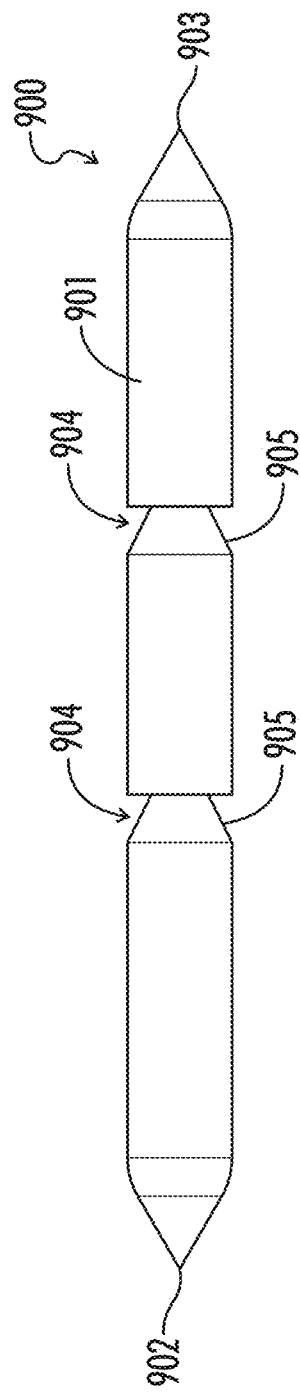
FIG. 31 illustrates a right side elevation view of the mandrel of FIG. 30.

FIGS. 11 and 14B illustrate a first, perspective view of one embodiment of a distal body 216 with twisting proximal strips 252, unattached distal-pointing crowns 258 that subtly curve inward and have x-ray markers 244, and enlarged openings/drop zones 262 in the basket 246 that allow the obstruction or other object 270 to enter. In FIGS. 11 and 14B, the distal body 216 is in Orientation 1. (To prepare a basket 246 with unattached distal-pointing crowns 258 that curve inward toward the basket interior 292, a mandrel 900 such as that illustrated in FIGS. 63 and 64 may be used. The mandrel 900 includes a generally cylindrical body 901 with tapered proximal and distal ends 902 and 903 that slope like the ends of a pencil. The cylindrical body 901 includes two grooves 904 that extend around the circumference of the cylindrical body 901. The grooves 904 include tapered portions 905 that slope towards the distal end 903, which are designed to shape the unattached distal-pointing crowns 258. The grooves 904 are generally in the shape of a truncated cone, as shown in FIGS. 30-31). The two proximal, unattached distal-pointing crowns 258A and 258B are located approximately the same distance from the proximal hub/junction/tube 228 and are oriented approximately 180 degrees relative to each other. The two distal, unattached distal-pointing crowns 258C and 258D are located approximately the same distance from the proximal hub/junction/tube 228 as each other (and distal to the two proximal, unattached distal-pointing crowns 258A and 258B) and are oriented approximately 180 degrees relative to each other and approximately 90 degrees to the proximal, unattached distal-pointing crowns 258A and 258B. For example, for purposes of FIGS. 11-29, "approximately the same distance from the proximal hub/junction/tube 228" means that if one free distal crown 258A of the first pair of distal crowns 258A/258B is located X distance from the proximal hub/junction/tube 228, the other distal crown 258B of the first pair of distal crowns 258A/258B is located X distance plus or minus (+/−) 3 millimeters (mm) from the proximal hub/junction/tube 228. Similarly, if one free distal crown 258C of the second pair of distal crowns 258C/258D is located Y distance from the proximal hub/junction/tube 228, the other distal crown 258D of the second pair of distal crowns 258C/258D is located Y distance plus or minus (+/−) 3 mm from the proximal hub/junction/tube 228. In a preferred embodiment, the first free distal crowns 258A and 258B are located the same distance+/−0.5 mm from the proximal hub/junction/tube 228. Similarly, in a preferred embodiment, the second free distal crowns 258C and 258D are located the same distance+/−0.5 mm from the proximal hub/junction/tube 228.

Figure 13:
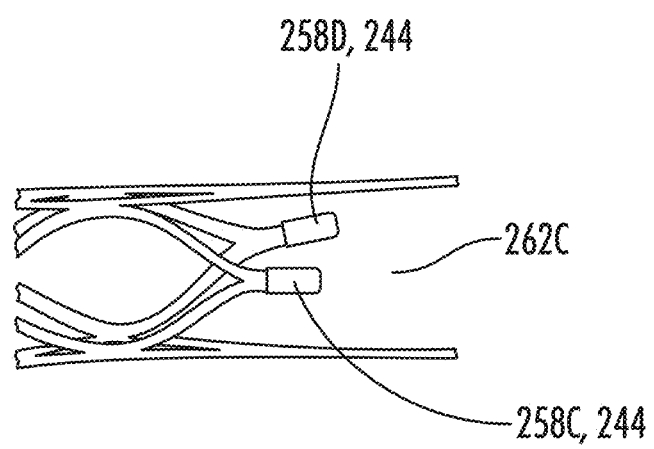
FIG. 13 illustrates a close-up, perspective view of two unattached distal-pointing crowns of the distal body of FIG. 11.

The two proximal enlarged openings/drop zones 262A and 262B distal to the proximal, unattached distal pointing crowns 258A and 258B are located approximately the same distance from the proximal hub/junction/tube 228 and the centers of the two proximal enlarged openings/drop zones 262A and 262B are oriented approximately 180 degrees relative to each other. (As noted above, preferably, the proximal, unattached distal-pointing crowns 258A and 258B form part of the proximal boundary of the proximal, enlarged cells/drop zones 262A and 262B, and the distal, unattached distal-pointing crowns 258C and 258C form part of the proximal boundary of the distal, enlarged cells/drop zones 262C and 262D). The two distal, enlarged openings/drop zones 262C and 262D distal to the distal, unattached distal pointing crowns 258C and 258D are located approximately the same distance from the proximal hub/junction/tube 228 and the centers of the distal, enlarged openings/drop zones 262C and 262D are oriented approximately 180 degrees relative to each other and approximately 90 degrees relative to the proximal enlarged openings/drop zones 262A and 262B. FIGS. 12A and 14C illustrate a second view of the distal body 216 of FIG. 11 (Orientation 2). FIG. 13 is a close-up view of two unattached, distal-pointing crowns 262. The lines in FIG. 14 show how a nitinol tube 264 is cut with a laser to create the distal body 216 shown in FIG. 14B and FIG. 14C. It will be appreciated that FIG. 14B is a simplified view of the distal body 216 and orientation shown in FIG. 11 and FIG. 14C is a simplified view of the distal body 216 and orientation shown in FIG. 12A.

As described below, FIGS. 15-19 describe how the distal body 216 is used to retrieve, soft clots 270A, hard clots 270B, and deformable, cohesive adhesive clots 270C in a human intracranial artery 266. (In FIGS. 15-19, the center of the artery 266 is denominated by the dashed line). As explained below, the distal body 216 has four rows of x-ray markers namely, 1) a first row of one x-ray marker, which is located inside the proximal tube denominated by the numeral 228, 244; 2) a second row of two x-ray markers, which are located at the two proximal, unattached distal-pointing crowns (the two markers are oriented 180 degrees relative to each other) denominated by the numerals 258A, 244 and 258B, 244; 3) a third row of two x-ray markers, which are located at the two distal, unattached distal-pointing crowns (these two markers are oriented 180 degrees relative to each other and 90 degrees relative to the two proximal, unattached distal-pointing crowns) denominated by the numerals 258C, 244 and 258D, 244; and 4) a fourth row of one x-ray marker, which is located inside the distal tube denominated by the numeral 236, 244. (It will be appreciated that the first number in the sequence describes the position of the x-ray marker and the second number, 244, represents the fact that the item is an x-ray marker). As explained below, upon deploying the distal body 216 so that the two proximal, unattached distal-pointing crowns 258A, 244 and 258B, 244 are immediately distal to the clot 270, the surgeon interventionalist (i.e., operator of the distal body 216) detects the four rows of x-ray markers using x-ray radiation from a first vantage point and from a second vantage point that is offset from the first vantage point (e.g. 90 degrees). Next, the surgeon moves the distal body 216 proximally relative to the clot 270 and takes additional x-rays from the first and second vantage points. As explained in greater detail below, the surgeon uses the x-ray markers of the proximal and distal, unattached distal-pointing crowns, namely 258A, 244; 258B, 244; 258C, 244; and 258D, 244 (more specifically, the convergence or lack thereof of the proximal and distal, unattached distal-pointing crowns 258A, 244; 258B, 244; 258C, 244; and 258D, 244 as shown on the x-ray) to determine whether the clot 270 is located inside the distal body interior 222 or whether the clot 270 is collapsing the distal body 216.

Figure 15A:
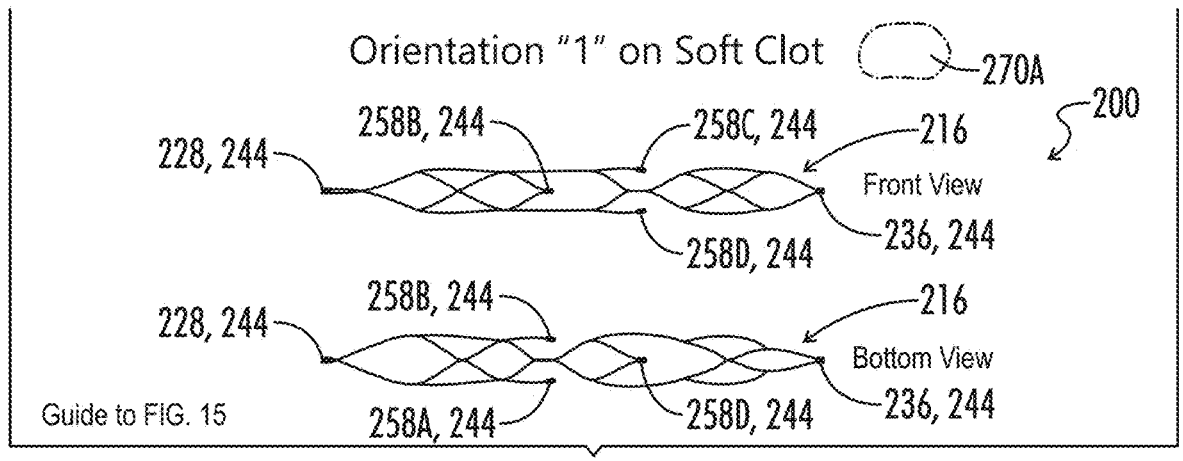
FIGS. 15A-G illustrate stepwise use of the distal body of FIG. 11 in retrieving a soft clot; the distal body is in Orientation 1.
Figure 15B:
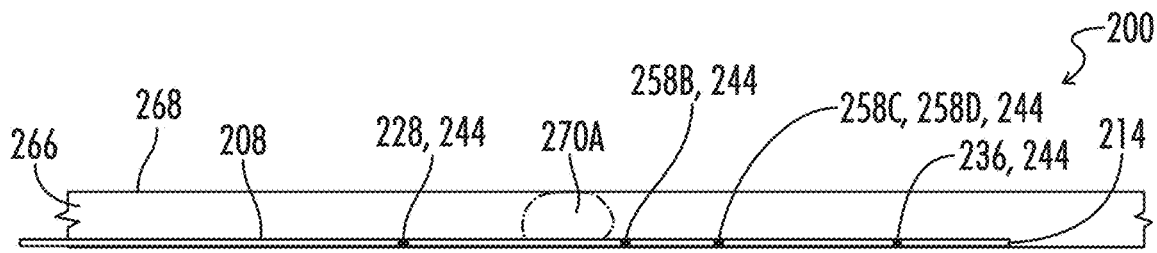
Figure 15C:
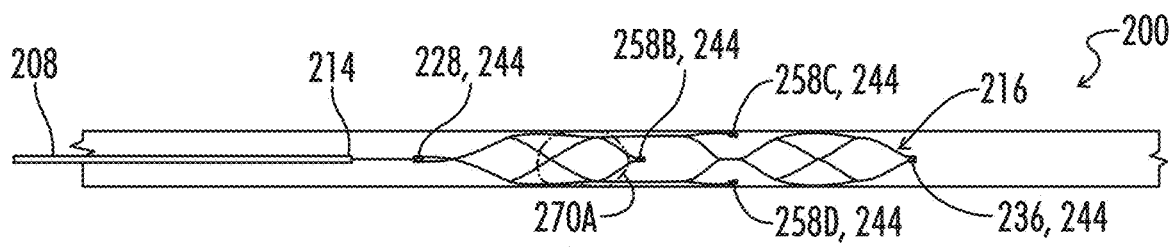
Figure 15D:
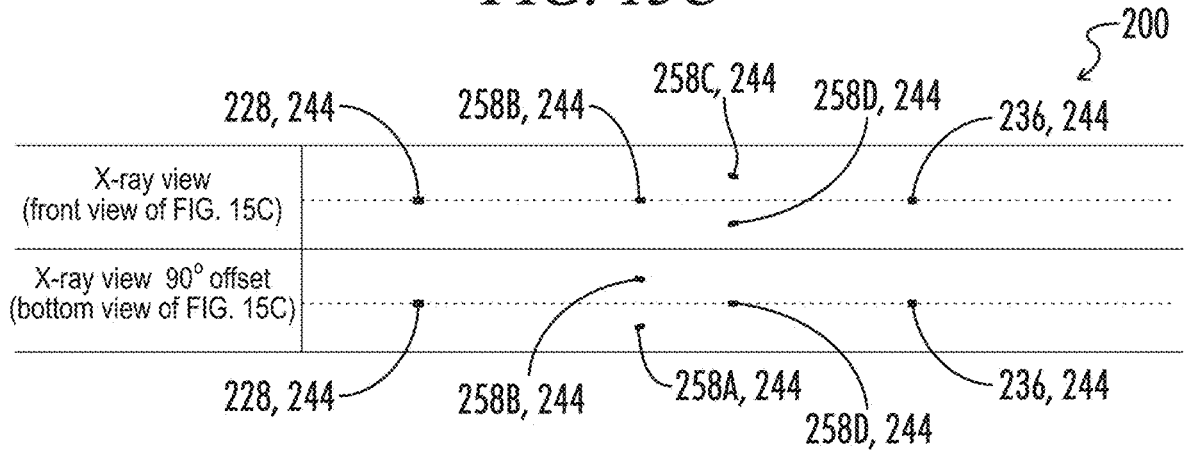
Figure 15E:
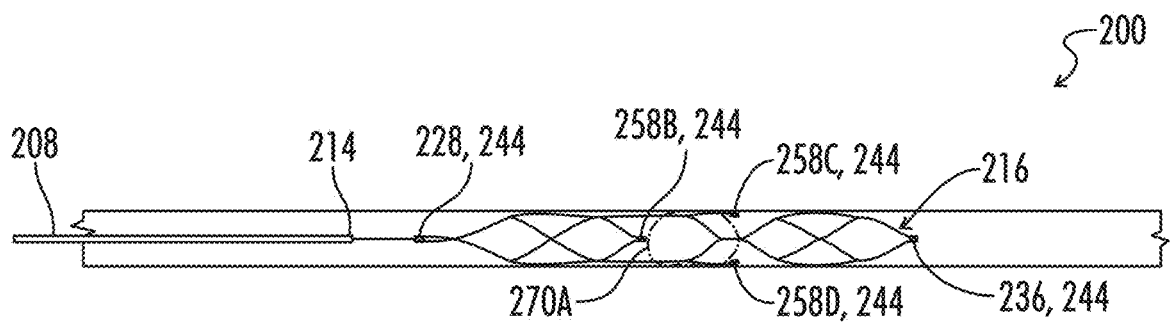
Figure 15F:
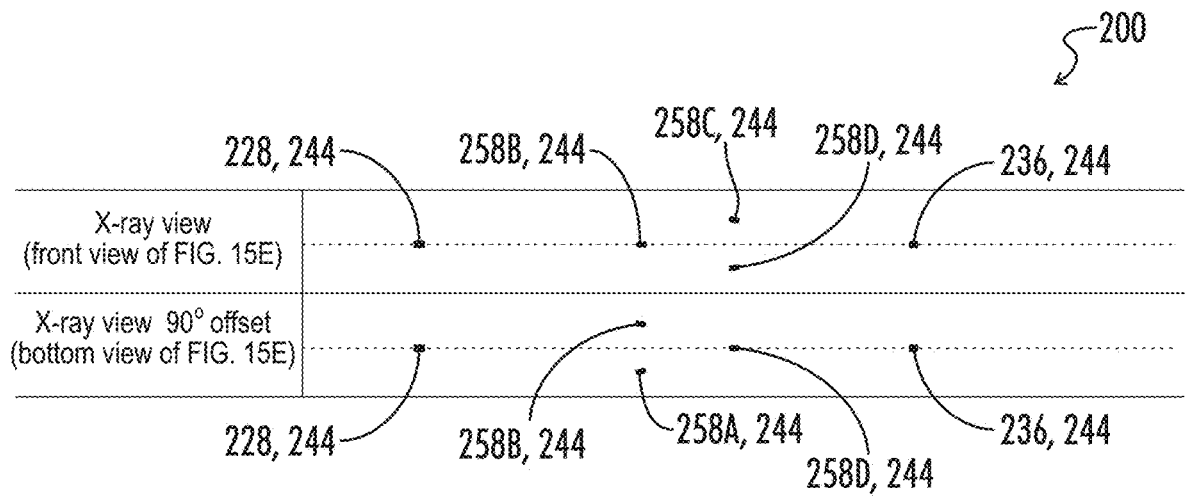
Figure 15G:
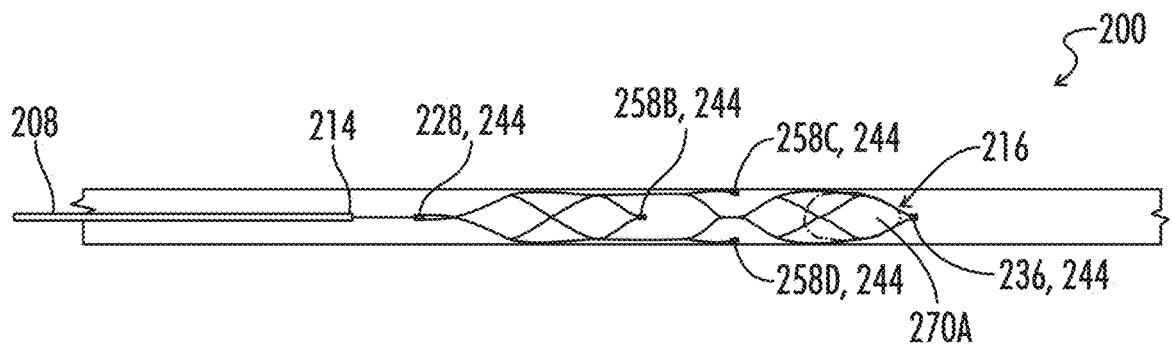

More specifically, FIGS. 15A-G illustrate stepwise use of the distal body 216 in retrieving a soft clot 270A in a human intracranial artery 266. (The distal body 216 in FIGS. 15A-15G is in Orientation 1). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 15B. The distal body 216 is then deployed from the delivery catheter 208 by moving the catheter 208 proximally. The soft clot 270A, which is unable to collapse the distal body 216, then enters the distal body interior 222. See FIG. 15C. However, at this time, the surgeon is unaware that the clot 270A has entered into the distal body interior 222. Thus, without moving the distal body 216, the surgeon irradiates the four rows of x-ray markers at a first vantage point (i.e., from the front of the distal body 216 in the orientation shown in FIGS. 15A-G; i.e., into the page). As shown in FIG. 15D, the first vantage point shows four rows of x-ray markers. The first row is a single point, which represents the x-ray marker located in the proximal tube 228, 244; the proximal tube x-ray marker 228, 244 always appears as a single point. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row 258C, 244 and 258D, 244 is hidden from view on the x-ray at this angle—rather, one marker 258C, 244 is located above the other marker 258D, 244—and as shown in FIG. 15C, the distal body 216 is not collapsed at the distal, unattached distal-pointing crowns 258C, 244 and 258D, 244. The fourth row is a single point, which represents the x-ray marker located in the distal tube 236, 244; the distal tube x-ray marker 236, 244 always appears as a single point. Without moving the distal body 216, the surgeon then irradiates the four rows of x-ray markers from a second vantage point 90 degrees offset from the first vantage point (i.e., from the bottom of the distal body 216 in the orientation shown in FIG. 15A). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker 258A, 244 and 258B, 244 in the second row is hidden from view on the x-ray at this offset angle—rather, one marker 258B, 244 is located above the other marker 258A, 244—and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the x-ray markers at the second row 258A, 244 and 258B, 244 nor the x-ray markers at the third row 258C, 244 and 258D, 244 (i.e., the x-ray markers at both the proximal and distal unattached distal pointing-crowns) have converged. As shown in FIG. 15E, the surgeon then moves the distal body 216 proximally relative to the soft clot 270A so that the distal, unattached distal-pointing crowns 258C, 244 and 258D, 244 are immediately distal to the clot 270A and then the surgeon irradiates the four rows of x-ray markers again from the first vantage point and the second vantage point. As shown in FIG. 15F, the results are the same as FIG. 15D. With the results from FIGS. 15D and 15F, the surgeon concludes that neither x-ray markers at the second row 258A, 244 and 258B, 244 nor the x-ray markers at the third row 258C, 244 and 258D, 244 (i.e., the x-ray markers at both the proximal and distal unattached distal pointing-crowns) converged at either the original position of the distal body 216 (FIGS. 15C and 15D) or the position after moving the distal body 216 proximally (FIGS. 15E and 15F), and, thus, the distal body 216 was expanded in the vessel 266 in both positions. Thus, the surgeon concludes that the clot is a soft clot 270A that has entered into the distal body interior 222 and the surgeon removes the distal body 216 and the soft clot 270A, captured by the distal body 216, by moving the distal body 216 proximally out of the vessel 266, as shown in FIG. 15G.

Figure 16A:
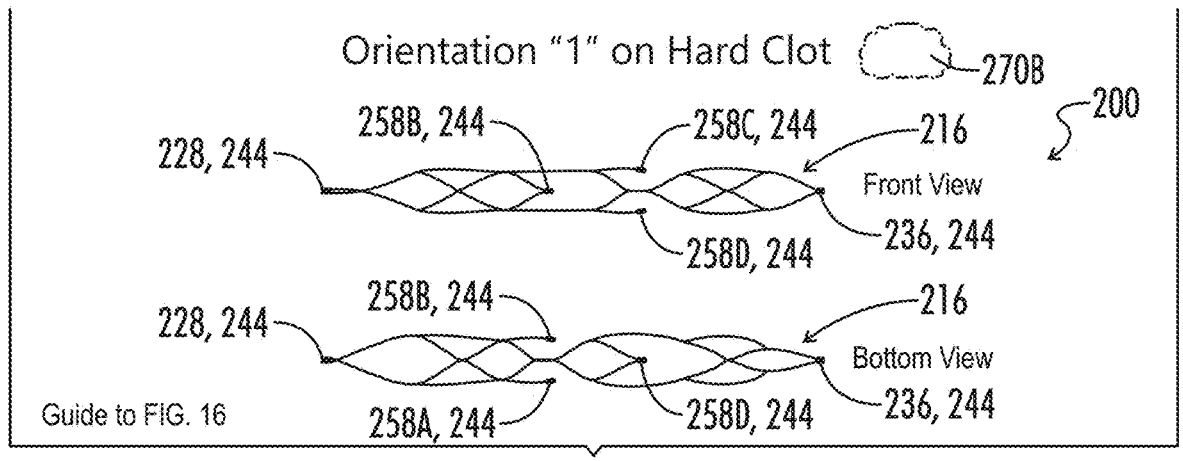
FIGS. 16A-H illustrate stepwise use of the distal body of FIG. 11 in retrieving a hard clot; the distal body is in Orientation 1.
Figure 16B:
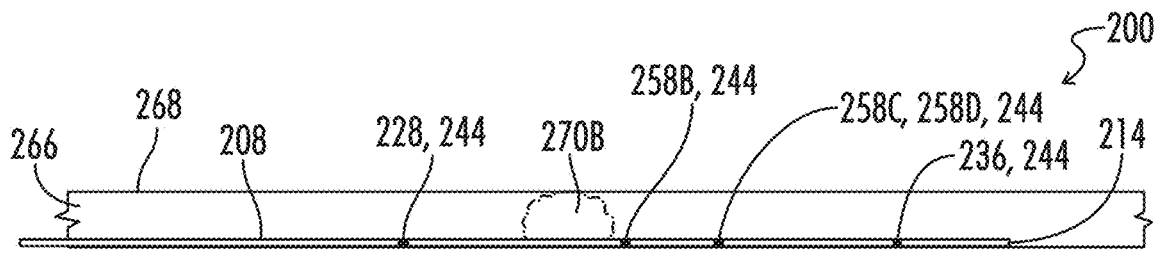
Figure 16C:
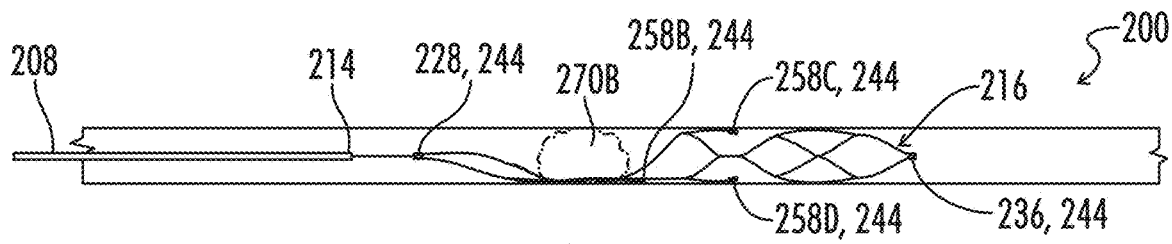
Figure 16D:
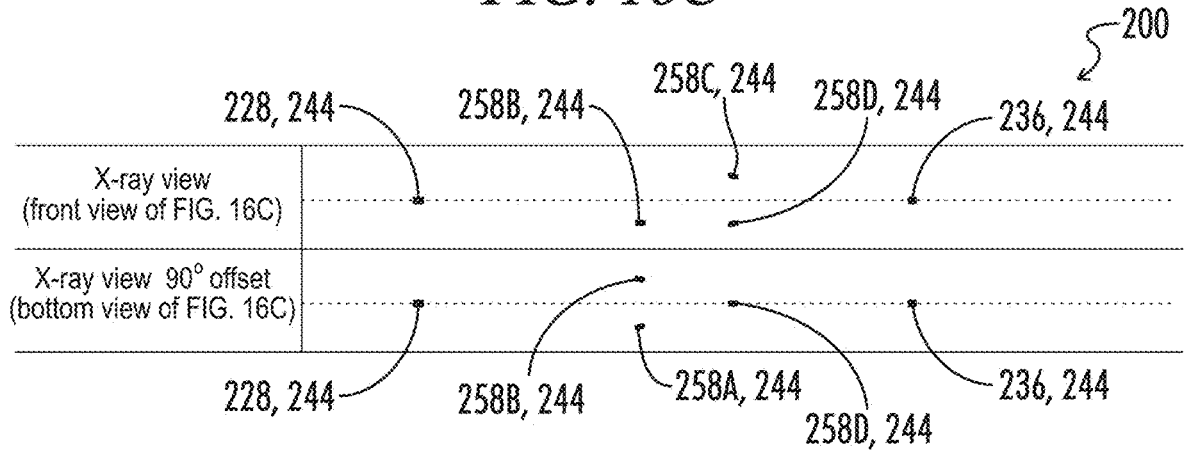
Figure 16E:
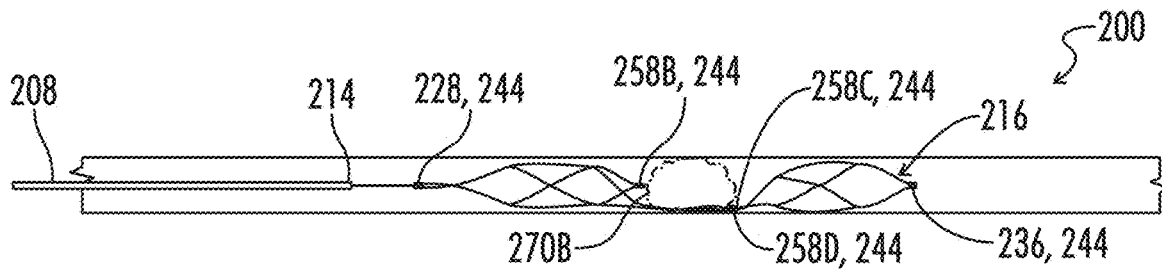
Figure 16F:
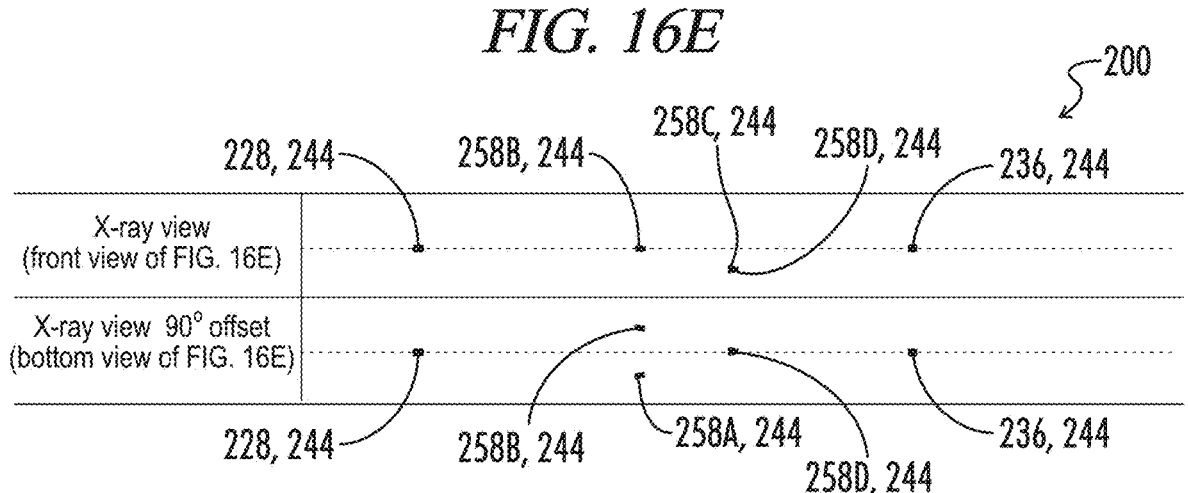
Figure 16G:
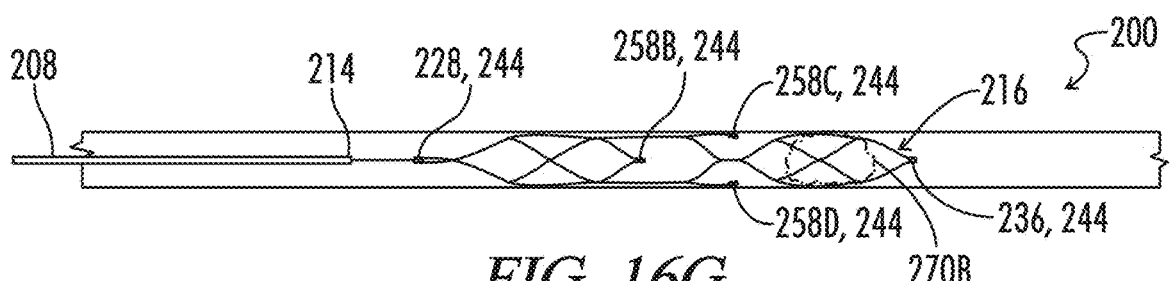
Figure 16H:
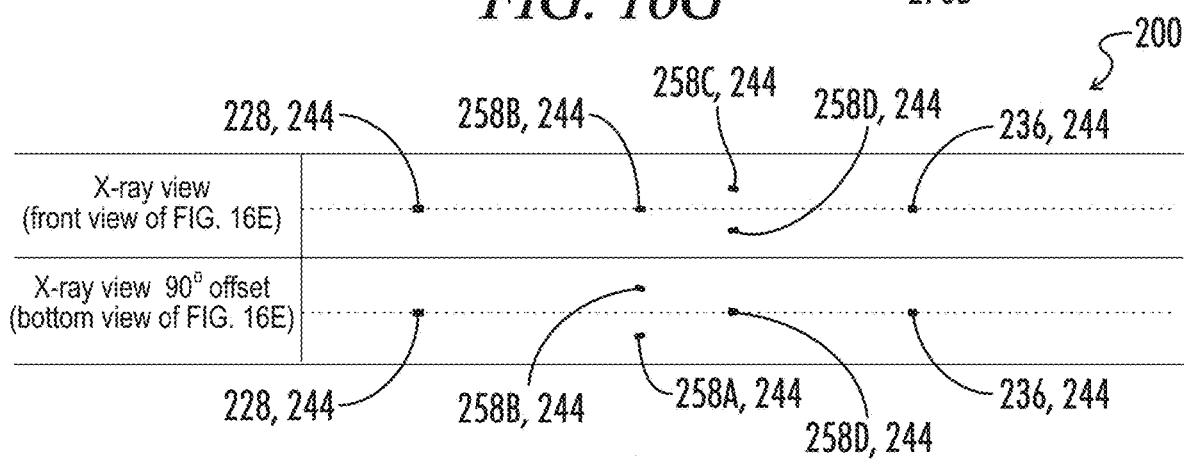

FIGS. 16A-H illustrate stepwise use of the distal body 216 in retrieving a hard clot 270B in a human intracranial artery 266. (In FIGS. 16A-H, the distal body 216 is in Orientation 1). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 16B. The distal body 216 is then deployed from the delivery catheter 208 by moving the catheter 208 proximally. The hard clot 270B, which is located above the distal body 216, collapses the distal body 216, as shown in FIG. 16C. However, at this time, the surgeon is unaware that the clot 270B has collapsed the distal body 216. Thus, without moving the distal body 216, the surgeon irradiates the x-ray markers at a first vantage point (i.e., from the front of the distal body 216; i.e., into the page). As shown in FIG. 16D, the first vantage point shows four rows of x-ray markers. The first row is, as always, a single point, representing the x-ray marker located in the proximal tube—i.e., 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row is hidden from view on the x-ray at this angle—rather, one marker 258C, 244 is located above the other marker 258D, 244—and as shown in FIG. 16C, the distal body 216 is not collapsed at the distal, unattached distal-pointing crowns 258C, 244 and 258D, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has two points, which represents the two x-ray markers located at the proximal, unattached distal-pointing crowns 258A, 244 and 258B, 244; the reason that this second row of markers shows up as two points is that neither marker in the second row is hidden from view on the x-ray at this offset angle—rather, one marker 258B, 244 is located above the other marker 258A, 244—and although the distal body 216 is collapsed at the proximal, unattached distal-pointing crowns as shown in FIG. 16C, the second row of x-ray markers have not converged because the clot 270B is on top of the second row of x-ray markers. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the second row 258A, 244 and 258B, 244 nor the third row 258C, 244 and 258D, 244 of x-ray markers (i.e., the x-ray markers at both the proximal and distal unattached distal pointing-crowns) has converged. As shown in FIG. 16E, the surgeon then moves the distal body 216 proximally so that the distal, unattached distal-pointing crowns 258C, 244 and 258D, 244 are immediately distal to the clot 270B and the surgeon then irradiates the x-markers again from the first vantage point. As shown in FIG. 16F, the first row is, as always, a single point, representing the x-ray marker located in the proximal tube 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has only one point because the clot 270B, which is on top of the third row of x-ray markers 258C, 244 and 258D, 244 (i.e., the markers at the distal, unattached distal-pointing crowns), has pushed the third row of x-ray markers 258C, 244 and 258D, 244 together. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker in the second row is hidden from view on the x-ray at this offset angle and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the bottom x-ray marker of the third row 258D, 244 is directly in front of the top x-ray marker of the third row 258C, 244, and thus, the top x-ray marker of the third row 258C, 244 is hidden from view. The fourth row is, as always, a single point, which represents the x-ray marker located in the distal tube 236, 244. Knowing that the distal, unattached distal-pointing crowns 258C, 244 and 258D, 244 have converged as shown in FIG. 16F, the surgeon moves the distal body 216 proximally and the hard clot 270B falls into the distal body interior 222 in the enlarged cell/drop zone 262C immediately distal to the top, distal, unattached distal-pointing crown 258C. See FIG. 16G. To confirm that the hard clot 270B has entered the distal body interior 222, the surgeon takes x-rays from the first and second vantage points. The results are shown in FIG. 16H. As compared to 16F, the front x-ray view of FIG. 16H shows that the distal, unattached distal-pointing crowns 258C, 244 and 258D, 244 are not converged, and, thus, the surgeon concludes that the hard clot 270B has entered the distal body interior 222. The surgeon then removes the distal body 216 and the hard clot 270B, captured by the distal body 216, by moving the distal body 216 proximally out of the vessel 266.

Figure 17A:
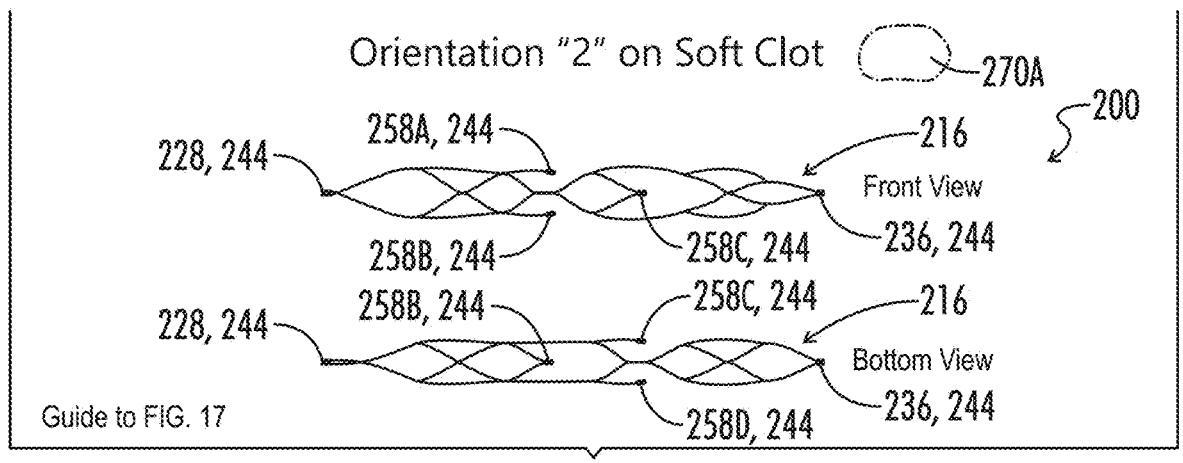
FIGS. 17A-G illustrate stepwise use of the distal body of FIG. 11 in retrieving a soft clot; the distal body is in Orientation 2.
Figure 17B:
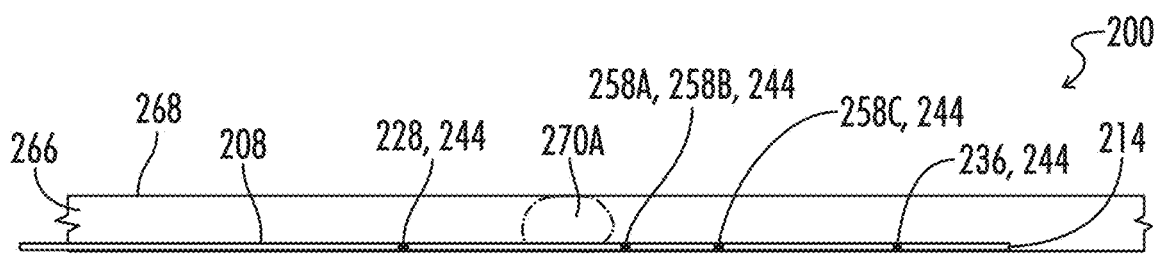
Figure 17C:
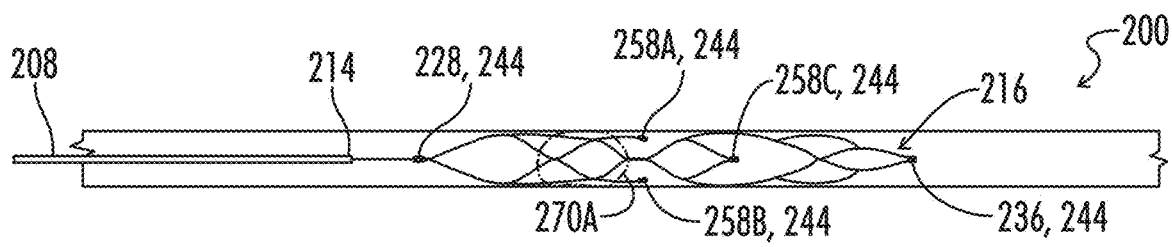
Figure 17D:
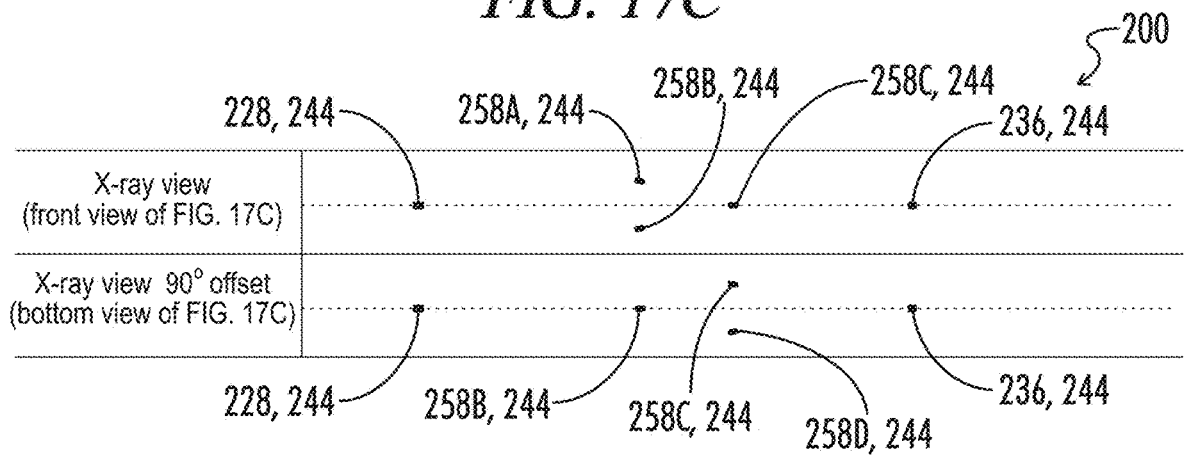
Figure 17E:
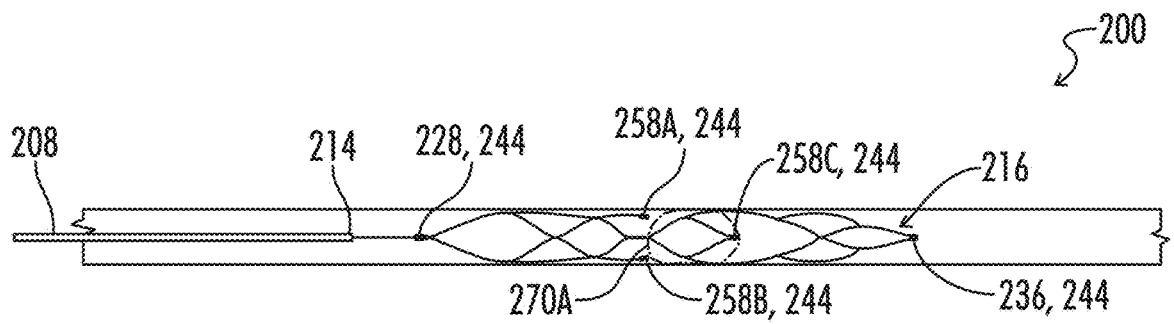
Figure 17F:
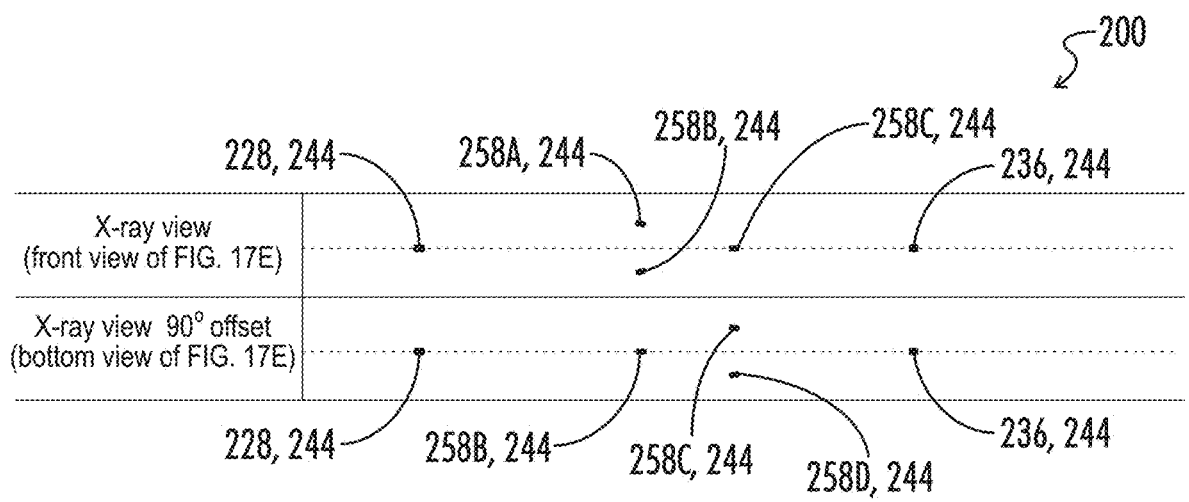

FIGS. 17A-G illustrate stepwise use of the distal body 216 in retrieving a soft clot 270A in a human intracranial artery 266. (In FIGS. 17A-G, the distal body 216 is in Orientation 2). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 17B. The distal body 216 is then deployed from the catheter 208 by moving the catheter 208 proximally. The soft clot 270A, which is unable to collapse the distal body 216, then enters the distal body interior 222. See FIG. 17C. However, at this time, the surgeon is unaware that the clot 270A has entered into the distal body interior 222. Thus, without moving the distal body 216, the surgeon irradiates the x-ray markers at a first vantage point (i.e., from the front of the distal body; into the page). As shown in FIG. 17D, the first vantage point shows four rows of x-ray markers. The first row is, as always, a single point, representing the x-ray marker located in the proximal tube 228, 244. The second row has two points, which represents the two x-ray markers located at the proximal, unattached distal-pointing crowns 258A, 244 and 258B, 244; the reason that this second row of markers has two points is that neither marker in the second row is hidden from view on the x-ray at this angle—rather, one marker 258A, 244 is located above the other marker 258B, 244—and as shown in FIG. 17C, the distal body 216 is not collapsed at the proximal, unattached distal-pointing crowns 258A, 244 and 258B, 244. The third row has a single point, which represents the x-ray marker located at the front (in Orientation 2), distal, unattached distal-pointing crown 258C, 244; the reason that this third row of markers is a single point is that the rear (in Orientation 2) x-ray marker 258D, 244 of the third row is hidden from view because it is directly behind the front x-ray marker 258C, 244 of the third row. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body, as shown in this view). As shown, the first row is, as always, a single point, which represents the x-ray marker located in the proximal tube 228, 244. The second row is a single point, which represents the x-ray marker located at the bottom (in Orientation 2), proximal, unattached distal-pointing crown 258B, 244; the reason that this second row of markers is a single point is that the top (in Orientation 2) x-ray marker of the second row 258A, 244 is directly behind the bottom x-ray marker of the second row 258B, 244, and thus, hidden from view. The third row has two points, which represents the two x-ray markers located at the distal, unattached distal-pointing crowns 258C, 244 and 258D, 244; the reason that this third row of markers shows up as two points is that neither marker in the third row is hidden from view on the x-ray at this offset angle and the distal body 216 is not collapsed at the distal, unattached distal-pointing crowns 258C, 244 and 258D, 244. The fourth row is, as always, a single point, which represents the x-ray marker located in the distal tube 236, 244. The surgeon, thus, concludes that neither the second row 258A, 244 and 258B, 244 nor the third row of x-ray markers 258C, 244 and 258D, 244 (i.e., the x-ray markers at both the proximal and distal unattached distal pointing-crowns) has converged. As shown in FIG. 17E, the surgeon then moves the distal body 216 proximally relative to the clot 270A so that the distal, unattached distal-pointing crowns 258C, 244 and 258D, 244 are immediately distal to the clot 270A and then the surgeon irradiates the x-markers again from the first vantage point and the second vantage point. As shown in FIG. 17F, the results are the same as FIG. 17D. With the results from FIGS. 17D and 17F, the surgeon concludes that neither the second row 258A, 244 and 258B, 244 nor the third row of x-ray markers 258C, 244 and 258D, 244 (i.e., the x-ray markers at both the proximal and distal unattached distal pointing-crowns) were converged at either the original position of the distal body 216 (FIGS. 17C and 17D) or the position after moving the distal body 216 proximally (FIGS.

Figure 17G:
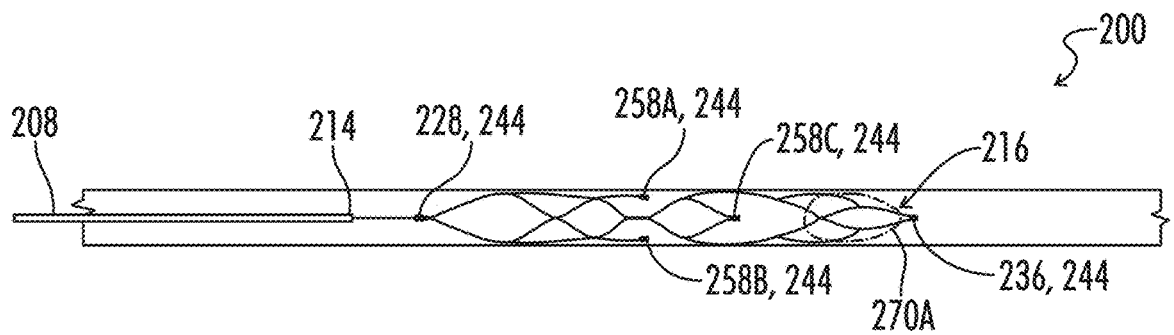

17E and 17F), and, thus, the distal body 216 was expanded in the vessel 266 in both positions. Thus, the surgeon concludes that the clot 270A is a soft clot 270A that has entered into the distal body interior 222 and the surgeon removes the distal body 216 and the soft clot 270A, captured by the distal body 216, by moving the distal body 216 proximally out of the vessel 266, as shown in FIG. 17G.

Figure 18A:
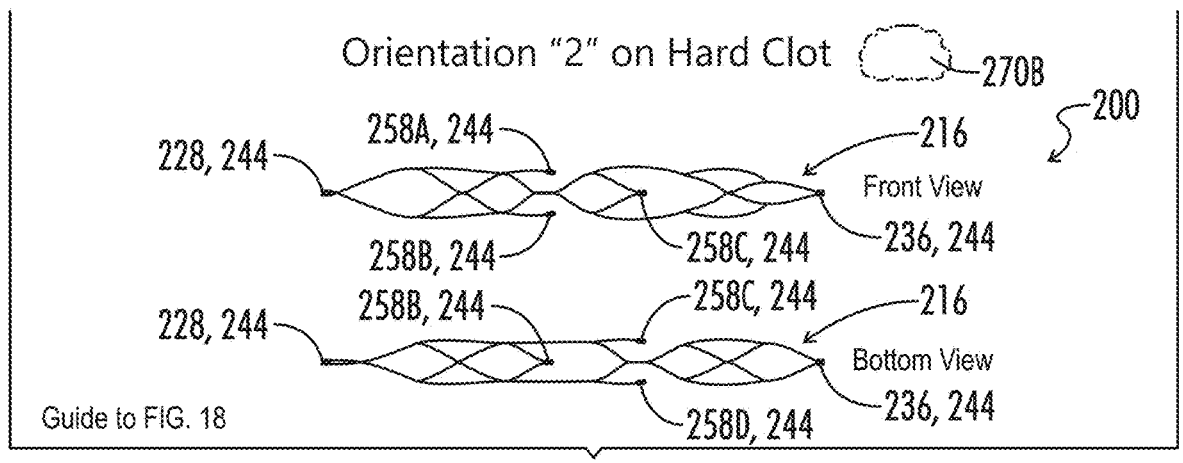
FIGS. 18A-G illustrate stepwise use of the distal body of FIG. 11 in retrieving a hard clot; the distal body is in Orientation 2.
Figure 18B:
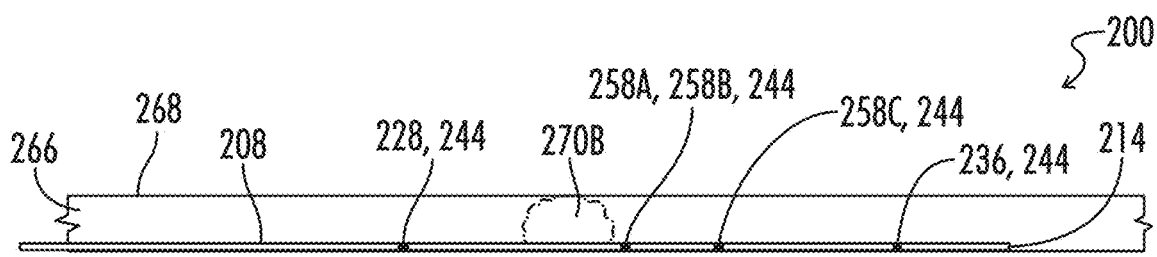
Figure 18C:
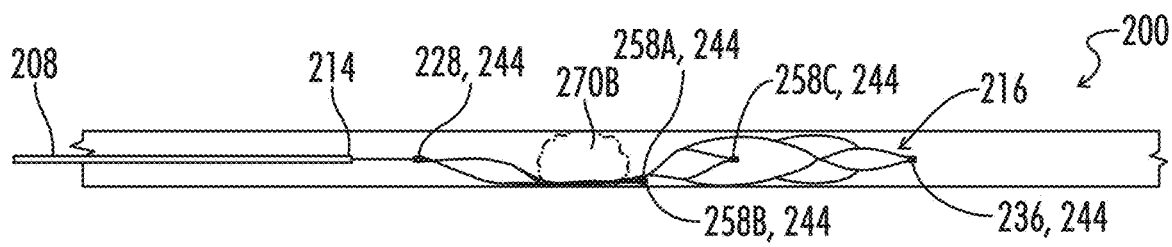
Figure 18D:
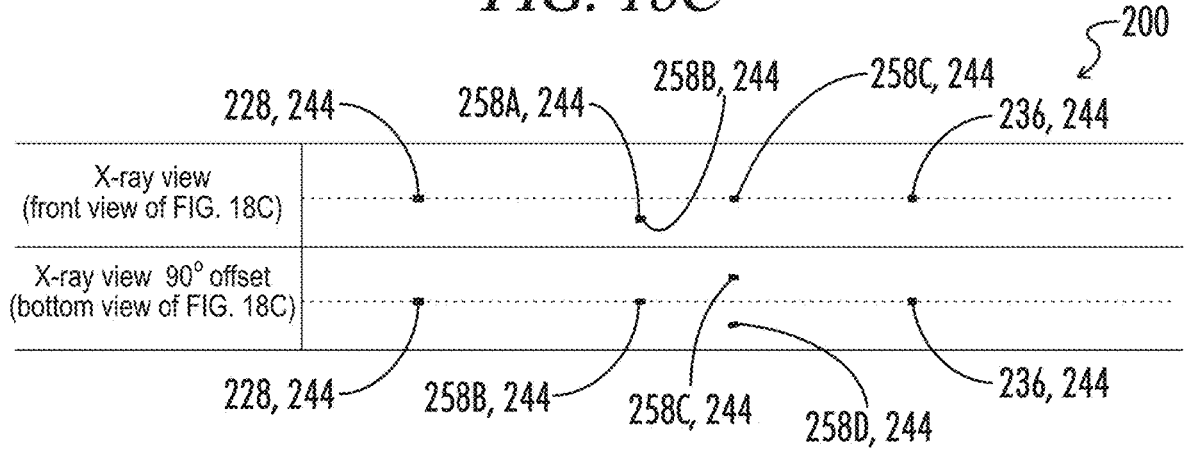
Figure 18E:
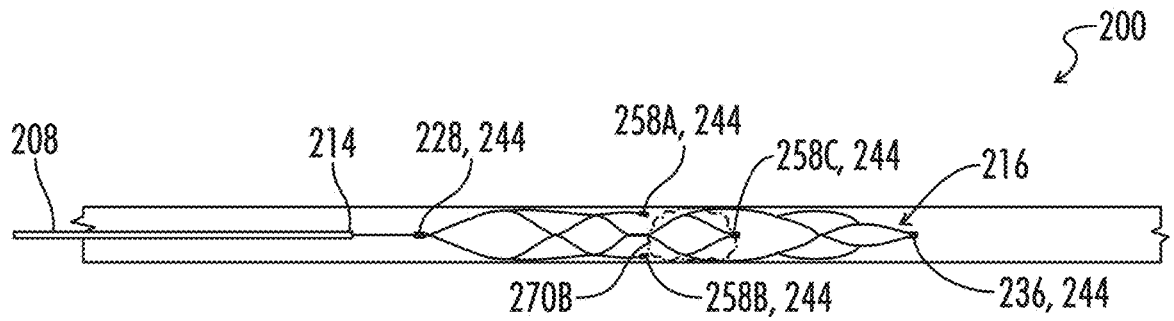
Figure 18F:
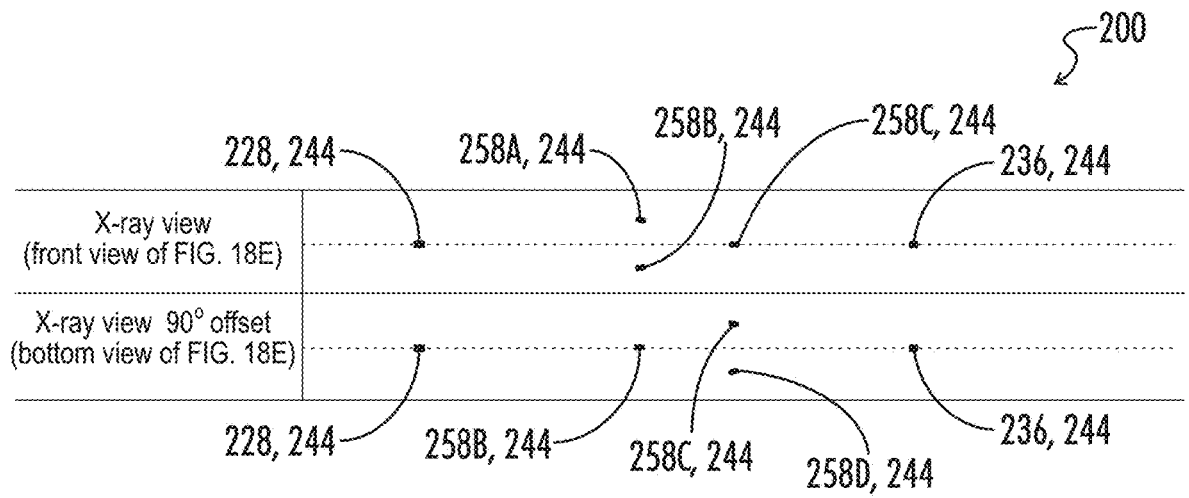
Figure 18G:
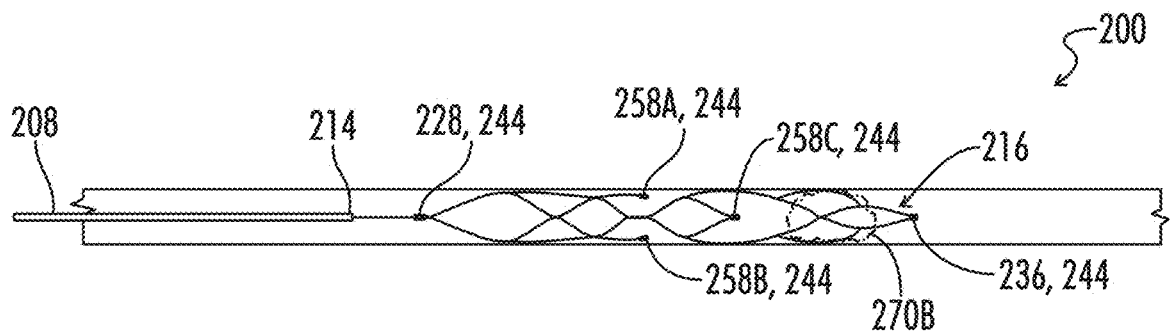

FIGS. 18A-G illustrate stepwise use of the distal body 216 in retrieving a hard clot 270B in a human intracranial artery 266. (In FIGS. 18A-G, the distal body 216 is in Orientation 2). (As described below, the primary differences between FIGS. 18A-G and FIGS. 16A-G is that the clot 270B enters the distal body interior 222 in an enlarged cell/drop zone 262A immediately distal to one of the proximal, unattached distal-pointing crowns 258A in FIGS. 18A-G, as compared to FIGS. 16A-G where the clot 270B enters the distal body interior 222 in an enlarged cell/drop zone 262C immediately distal to one of the distal, unattached distal-pointing crowns 258C). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 18B. The distal body 216 is then deployed from the catheter 208 by moving the catheter 208 proximally. The hard clot 270B, which is located above the distal body 216, collapses the distal body 216, as shown in FIG. 18C. However, at this time, the surgeon is unaware that the clot 270B has collapsed the distal body 216. Thus, without moving the distal body 216, the surgeon irradiates the x-ray markers at a first vantage point (i.e., from the front of the distal body in Orientation 2; into the page). As shown in FIG. 18D, the first vantage point shows four rows of x-ray markers. The first row is, as always, a single point, representing the x-ray marker located in the proximal tube 228, 244. The second row has only one point because the clot 270B, which is on top of the second row of x-ray markers 258A, 244 and 258B, 244 (i.e., the markers at the proximal, unattached distal-pointing crowns), has pushed them together. The third row has only one point, which represents the x-ray marker located at the front (in Orientation 2), proximal, unattached distal-pointing crown 258C, 244; the reason that this third row of markers is a single point is that the rear (in this view) x-ray marker of the third row 258D, 244 is hidden from view because it is directly behind the front x-ray marker of the third row 258C, 244. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the top (in Orientation 2) x-ray marker of the second row 258A, 244 is located behind the bottom (in Orientation 2) x-ray marker 258B, 244 and thus, the top x-ray marker of the second row 258A, 244 is hidden from view. The third row has two points, which represents the x-ray markers located at the distal, unattached distal-pointing crowns 258C, 244 and 258D, 244; in this x-ray view neither of the x-ray markers of the third row is hidden from view. The fourth row is, as always, a single point, which represents the x-ray marker located in the distal tube 236, 244. The surgeon, thus, concludes that the second row of x-ray markers 258A, 244 and 258B, 244 (i.e., the x-ray markers at the proximal, unattached distal pointing-crowns) has converged. As shown in FIG. 18E, the surgeon then moves the distal body 216 proximally so that the distal, unattached distal-pointing crowns 258C, 244 and 258D, 244 are immediately distal to the clot 270B. Unbeknownst to the surgeon, the clot 270B enters the distal body interior 222 immediately distal to the top (in Orientation 2), proximal unattached distal-pointing crown 258A and the distal body 216 is no longer collapsed. The surgeon then irradiates the x-markers again from the first vantage point. As shown in FIG. 18F, the first row is, as always, a single point, representing the x-ray marker located in the proximal tube 228, 244. The second row has two x-ray markers because the distal body 216 is not collapsed and neither the top (in Orientation 2) 258A, 244 nor the bottom 258B, 244 (in Orientation 2) x-ray marker of the second row (i.e., the marker at the proximal, unattached distal-pointing crowns) is hidden from view. The third row has only one point because the rear (in Orientation 2), distal unattached distal-pointing crown 258D, 244 is hidden behind the front (in Orientation 2), distal, unattached distal pointing-crown 258C, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the x-ray marker at the top (in Orientation 2), proximal, unattached distal-pointing crown 258A, 244 is hidden behind the bottom (in Orientation 2), proximal, unattached-distal pointing crown 258B, 244. The third row has two points because neither the front nor the rear x-ray markers at the distal, unattached, distal-pointing crowns 258C, 244 and 258D, 244 is hidden from view. The fourth row is, as always, a single point, which represents the x-ray marker located in the distal tube 236, 244. Based on the information from FIGS. 18D and 18F, the surgeon concludes that the clot 270B has entered into the distal body interior 222. The surgeon then removes the distal body 216 and the hard clot 270B, captured by the distal body 216, by moving the distal body 216 proximally out of the vessel 266, as shown in FIG. 18G. Upon comparing FIGS. 16A-G and FIGS. 18A-G it will be appreciated that the orientation of the enlarged cells/drop zone 262A-D relative to the orientation of a hard clot 270B determine which enlarged cell/drop zone 262A, 262B, 262C, or 262D, the hard clot 270 enters the distal body interior 222 through. For example, in FIG. 16C, the hard clot 270B is located above the distal body 216, and thus, the hard clot 270B must enter through the enlarged cell/drop zone located at the top of the distal body, which in the orientation of the distal body shown in FIGS. 16A-G, is the enlarged cell/drop zone 262C immediately distal to the top, distal, unattached, distal-pointing crown 258C. In FIG. 18C, the hard clot 270B is again located above the distal body and, thus, the hard clot 270B must enter through the enlarged cell/drop zone located at the top of the distal body. However, in FIG. 18C, the enlarged cell/drop zone located at the top of the distal body 216, in the orientation of the distal body 216 shown in FIGS. 18A-G, is the enlarged cell/drop zone 262A immediately distal to the top, proximal, unattached, distal-pointing crown 258A.

Figure 19A:
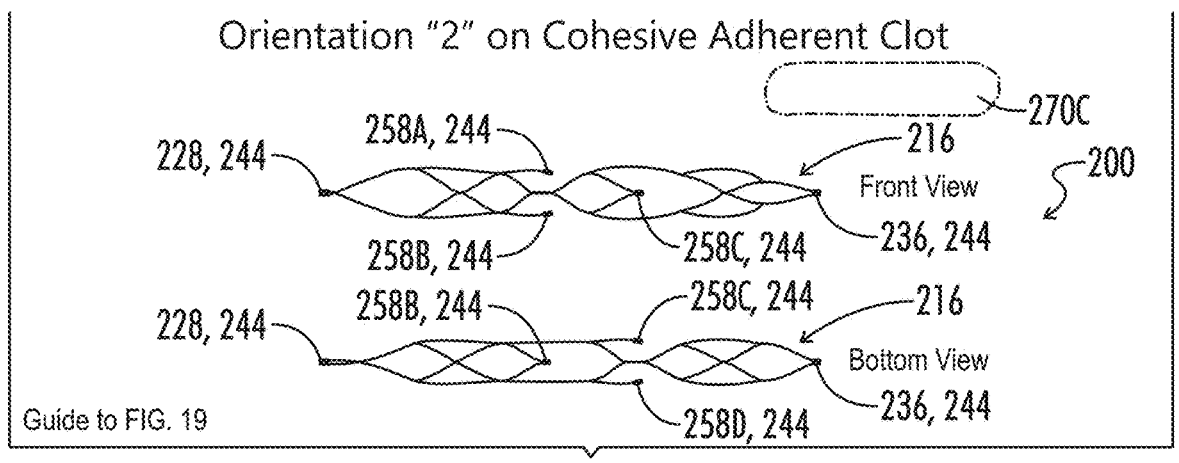
FIGS. 19A-N illustrate stepwise use of the distal body of FIG. 11 in retrieving a deformable, cohesive adherent clot; the distal body is in Orientation 2.
Figure 19B:
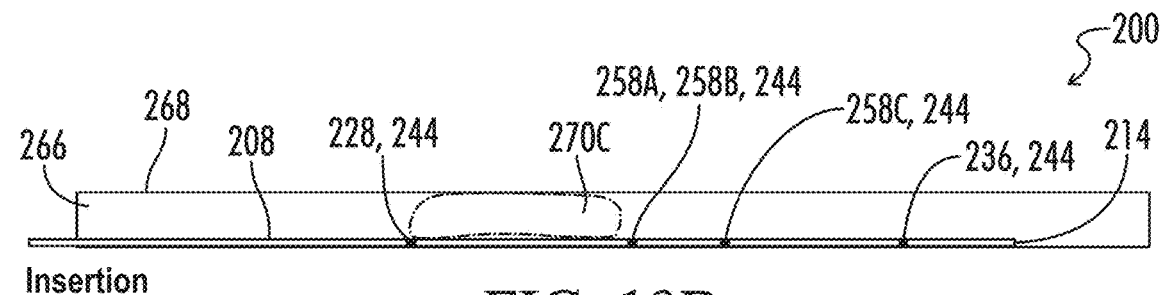
Figure 19C:
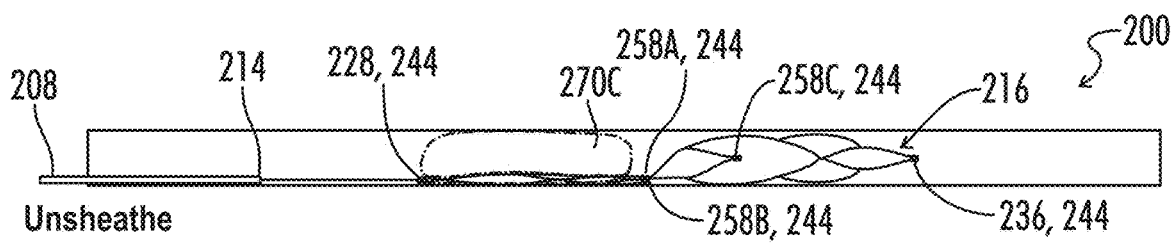
Figure 19D:
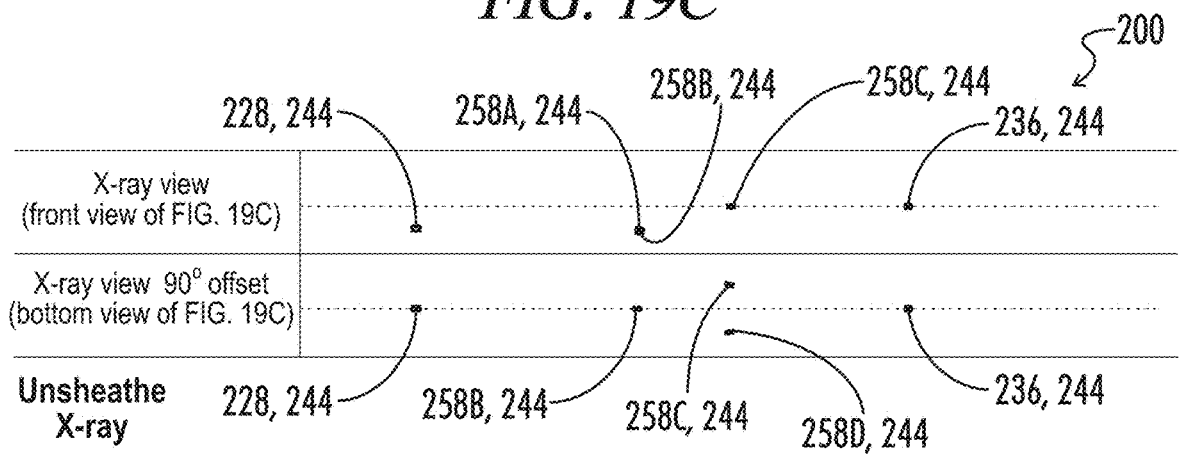
Figure 19E:
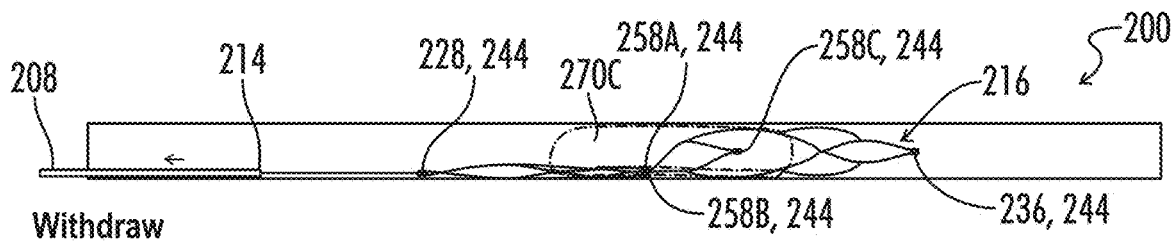
Figure 19F:
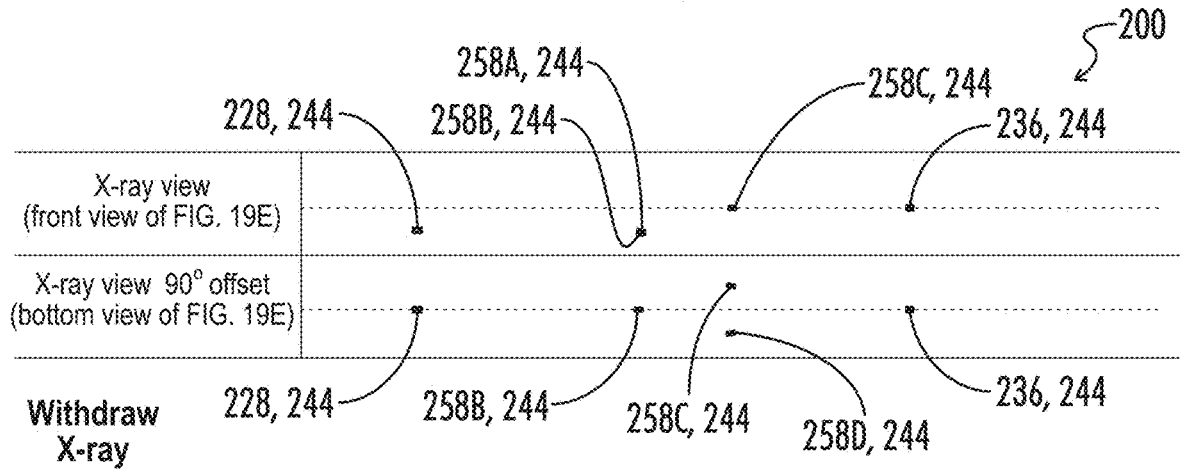
Figure 19G:
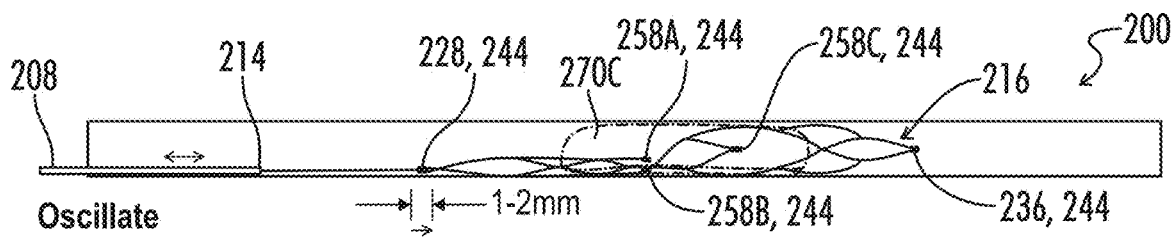
Figure 19H:
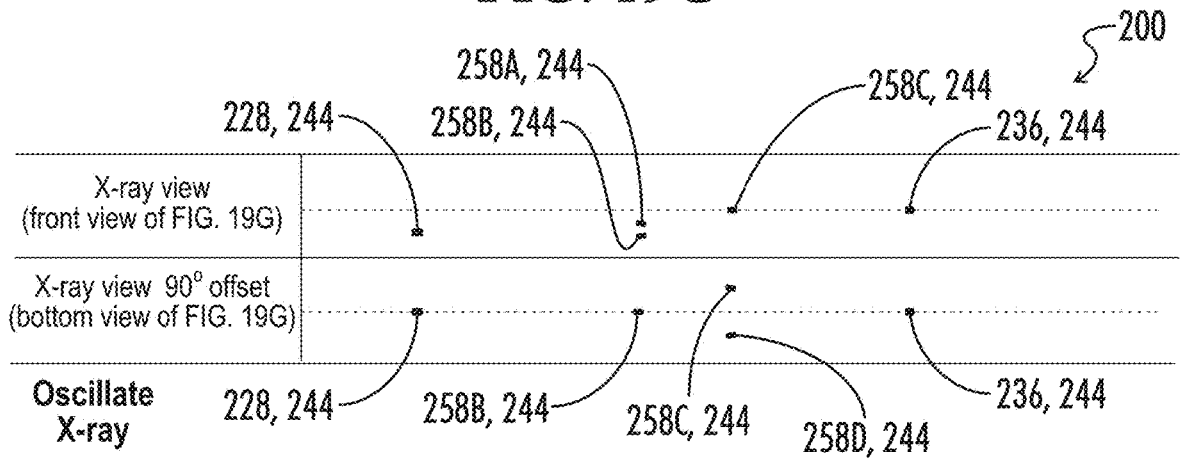
Figure 19I:
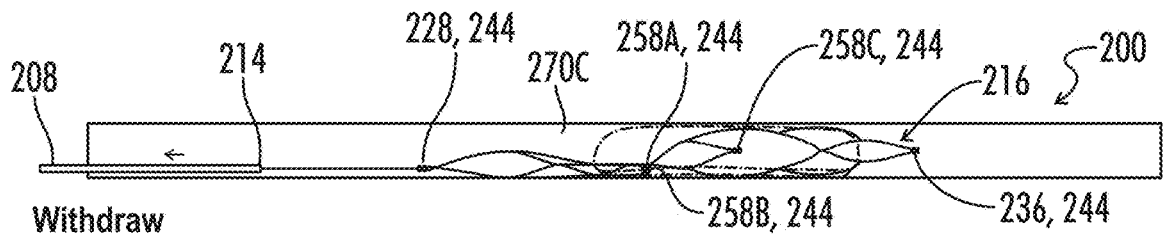
Figure 19J:
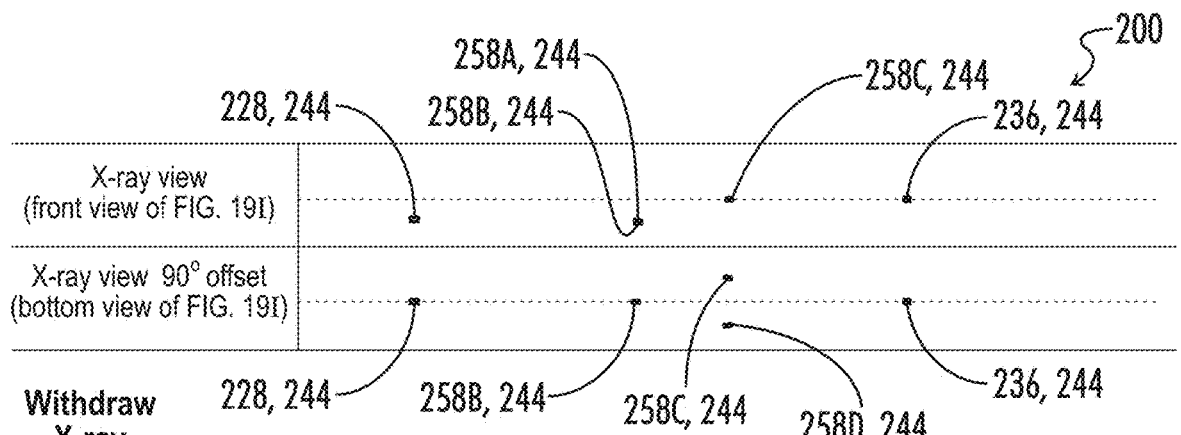
Figure 19K:
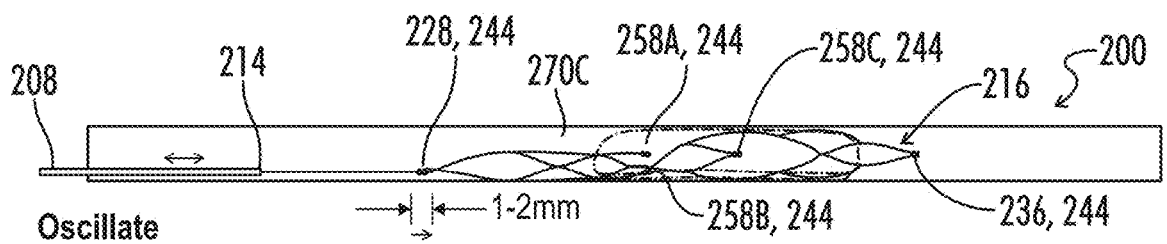
Figure 19L:
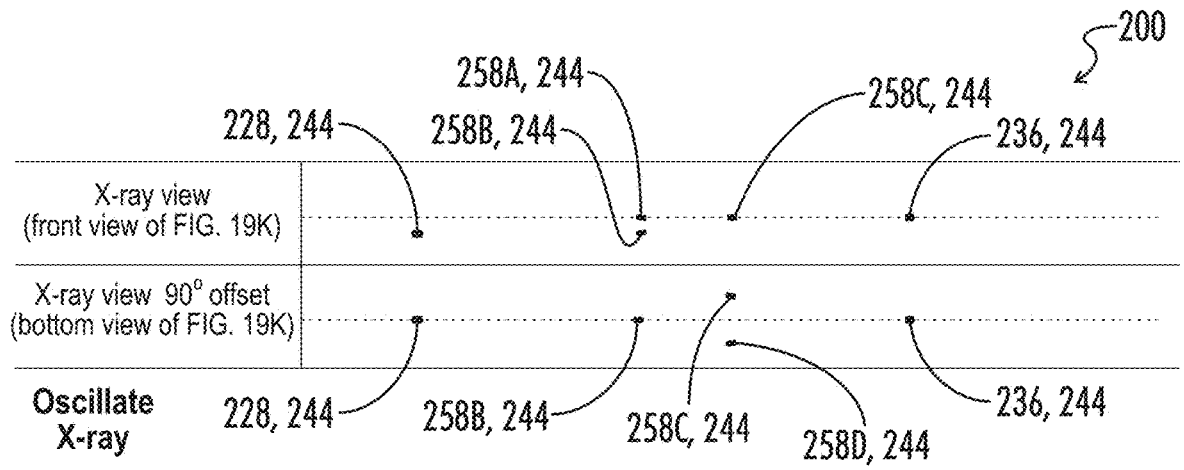
Figure 19M:
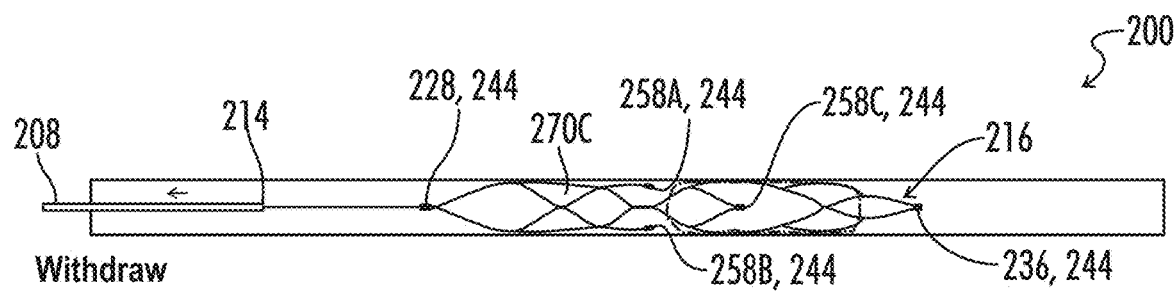
Figure 19N:
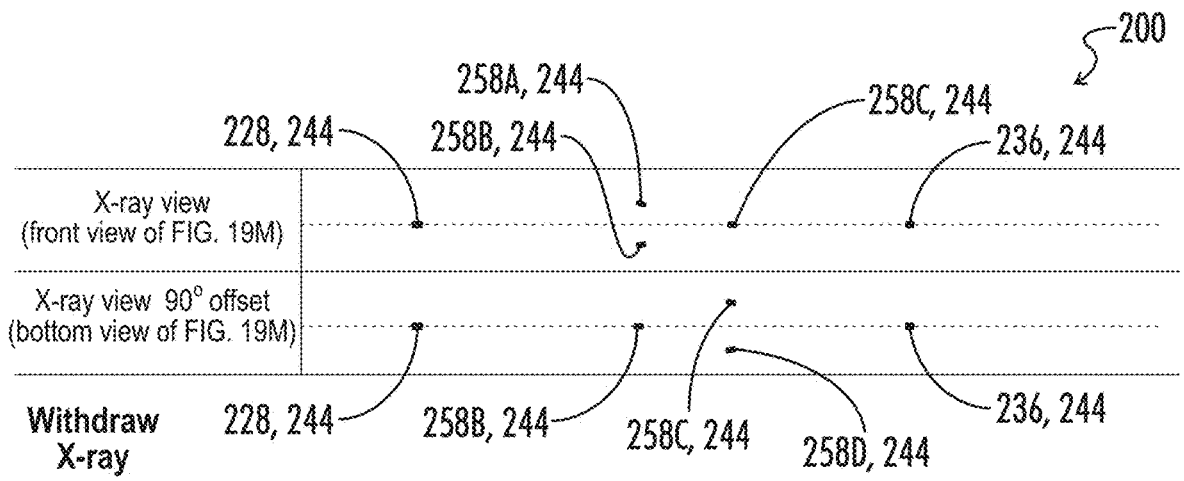

FIGS. 19A-N illustrate stepwise use of the distal body 216 in retrieving a deformable cohesive, adherent clot 270C—i.e., a clot that is difficult to break up and is tightly adhered to the vessel wall 268—in a human intracranial artery 266.

(In FIGS. 19A-N, the distal body 216 is in Orientation 2). First, as always, the surgeon determines the location of the clot 270C in the vessel 266 using, for example, a contrast dye injected proximal and distal to the clot 270C. Next, the delivery catheter 208, which is enveloping the distal body 216, is positioned in the blood vessel 266 so that the two proximal, unattached distal-pointing crowns 258A and 258B are immediately distal to the clot 270C. See FIG. 19B. The distal body 216 is then deployed from the catheter 208 by moving the catheter 208 proximally. The deformable, cohesive adherent clot 270C, which is located above the distal body 216, collapses the distal body 216, as shown in FIG. 19C. However, at this time, the surgeon is unaware that the clot 270C has collapsed the distal body 216. Thus, without moving the distal body 216, the surgeon irradiates the x-ray markers at a first vantage point (i.e., from the front of the distal body; i.e., into the page). As shown in FIG. 19D, the first vantage point shows four rows of x-ray markers. The first row is, as always, a single point, representing the x-ray marker located in the proximal tube 228, 244. The second row has a single point, corresponding to the top (in Orientation 2) and bottom (in Orientation 2), proximal, unattached distal-pointing crowns 258A, 244 and 258B, 244, which have converged because the clot 270C is collapsing the distal body 216. The third row has a single point, which represents the x-ray marker located at the front (in Orientation 2), distal, unattached distal-pointing crown 258C, 244; the x-ray marker located at the rear, distal, unattached distal-pointing crown 258D, 244 is hidden from view. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has a single point, which corresponds to the bottom (in Orientation 2), proximal, unattached distal-pointing crown 258B, 244; the top (in Orientation 2), proximal, unattached distal-pointing crown 258A, 244 is located behind the bottom, proximal, unattached distal-pointing crown 258B, 244 and hidden from view. The third row has two points, which correspond to the front (in Orientation 2) 258C, 244 and rear 258D, 244 (in Orientation 2), distal, unattached distal-pointing crowns, neither of which is blocked in this view. The fourth row is, as always, a single point, which represents the x-ray marker located in the distal tube 236, 244. As shown in FIG. 19E, the surgeon then moves the distal body 216 proximally (i.e., slightly withdraws the distal body 216). The surgeon then irradiates the x-markers again from the first and second vantage points. As shown in FIG. 19F, the results are exactly the same as in FIG. 19D. Based on the observation that the proximal, unattached distal-pointing crowns 258A, 244 and 258B, 244 have converged at both the original position (FIGS. 19C and 19D in which the proximal, unattached distal-pointing crowns 258A, 244 and 258B, 244 are immediately distal to the clot 270C) and the second position (FIGS. 19E and 19F), the surgeon concludes that the clot 270C is a deformable cohesive, adherent clot 270C. The surgeon then oscillates the distal body 216 proximally and distally a small distance (e.g., about 1 mm to about 2 mm) in the vessel 266, and the clot 270C begins to enter the distal body 216, as shown in FIG. 19G. The surgeon then irradiates the x-markers again from the first and second vantage points. As shown in FIG. 19H, the results are exactly the same as in FIG. 19D and FIG. 19F except that the second row of markers 258A, 244 and 258B, 244 (at the proximal, unattached distal-pointing crowns) are beginning to move apart. The surgeon then moves the distal body 216 proximally again, as shown in FIG. 19I. The surgeon then irradiates the x-markers again from the first and second vantage points. As shown in FIG. 19J, the results are exactly the same as in FIGS. 19D and 19F, as the clot 270C has caused the second row of markers 258A, 244 and 258B, 244 to re-converge. The surgeon then oscillates the distal body 216 proximally and distally a small distance (e.g., about 1 mm to about 2 mm) in the vessel 266, and the clot 270C begins to further enter the distal body interior 222, as shown in FIG. 19K. The surgeon then irradiates the x-markers again from the first and second vantage points. As shown in FIG. 19L, the results are the same as in FIG. 19H. The surgeon then moves the distal body 216 again proximally, and, instead of collapsing the second row of markers 258A, 244 and 258B, 244, the clot 270C fully enters the distal body interior 222, as shown in FIG. 19M. The surgeon then irradiates the x-markers again from the first and second vantage points. As shown in FIG. 19N, the results show that the second row of markers 258A, 244 and 258B, 244 (at the proximal, unattached distal-pointing crowns) have moved apart. Satisfied that the x-ray markers in the second row 258A, 244 and 258B, 244 (at the proximal, unattached distal-pointing crowns) are sufficiently far apart and that the x-ray markers in the third row (at the distal, unattached distal-pointing crowns) 258C, 244 and 258D, 244 have stayed far apart, the surgeon concludes that the deformable cohesive, adherent clot 270C has been sufficiently captured by the distal body 216 and the surgeon then removes the distal body 216 and the clot 270C, captured by the distal body 216, by moving the distal body 216 proximally out of the vessel 266.

Several observations can be made from FIGS. 15-19, as indicated above. For example, the x-ray markers at the proximal and distal, unattached distal-pointing crowns 258A-D, 244 provide the surgeon feedback concerning the interaction between the distal body 216 and the clot 270 in the blood vessel 266. In addition, the guiding principle of a soft clot 270A is that the soft clot 270A does not collapse the distal body 216, and thus, x-ray markers at the proximal and distal, unattached distal-pointing crowns 258A-D, 244 always appear as two points except when a marker is hidden behind another marker (due to the view). When it comes to a hard clot 270B, the hard clot 270B is generally able to enter the distal body interior 222 without needing to oscillate the distal body 216 proximally and distally (unlike a deformable cohesive, adherent clot 270C). However, to capture the hard clot 270B, the hard clot 270B must be oriented properly relative to the enlarged cell/drop zones 262A, 262B, 262C, or 262D. (This is the reason that the distal body 216 has four enlarged cells/drop zones: one enlarged cells/drop zone at 0 degrees 262B, one enlarged cells/drop zone at 90 degrees 262C, one enlarged cells/drop zone at 180 degrees 262A and one enlarged cells/drop zone at 270 degrees 262D). As a guiding principle, an enlarged cell/drop zone 262A, 262B, 262C, or 262D is properly oriented to the clot 270B when the x-ray markers at the proximal, unattached distal-pointing crowns 258A, 244 and 258B, 244 or the distal, unattached distal pointing crowns 258C, 244 and 258D, 244 are together at both a first x-ray view and a second x-ray view 90 degrees relative to the first x-ray view, and the hard clot 270B can enter the enlarged cell/drop zone 262A, 262B, 262C, or 262D by moving the distal body 216 proximally. See FIGS. 16F and 18D. Finally, the guiding principal of retrieval of deformable cohesive, adherent clots 270C is that oscillation of the distal body 216 causes the deformable cohesive, adherent clots 270C to gradually enter the distal basket interior 222 over time.

Figure 20A:
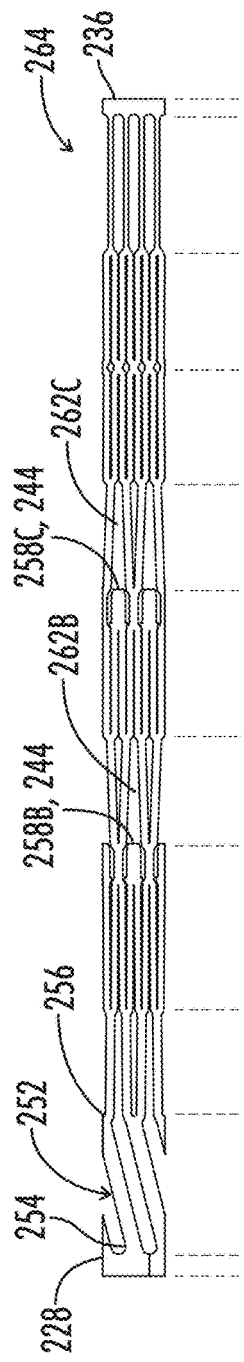
FIG. 20A illustrates a view of a native memory metal tube used to manufacture a distal body of yet another embodiment of the present invention; the native tube has been rolled out flat, the lines in the tube indicate where the tube has been cut by a laser, and the distal body of FIGS. 20A-20C is slightly shorter than the distal body of FIGS. 11-19 and is meant for use in tortuous blood vessels.
Figure 20B:
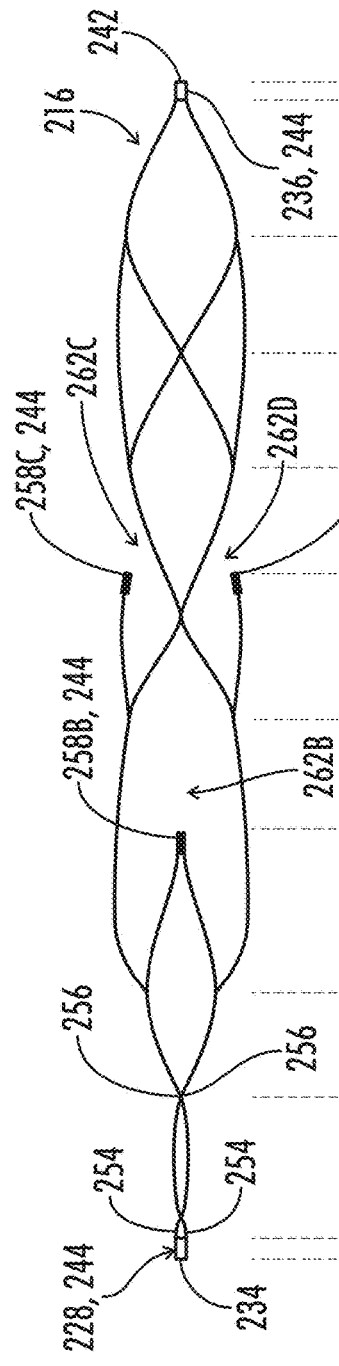
FIG. 20B illustrates a first, perspective view of the distal body manufactured from the native tube of FIG. 20A; the distal body is in Orientation 1.
Figure 20C:
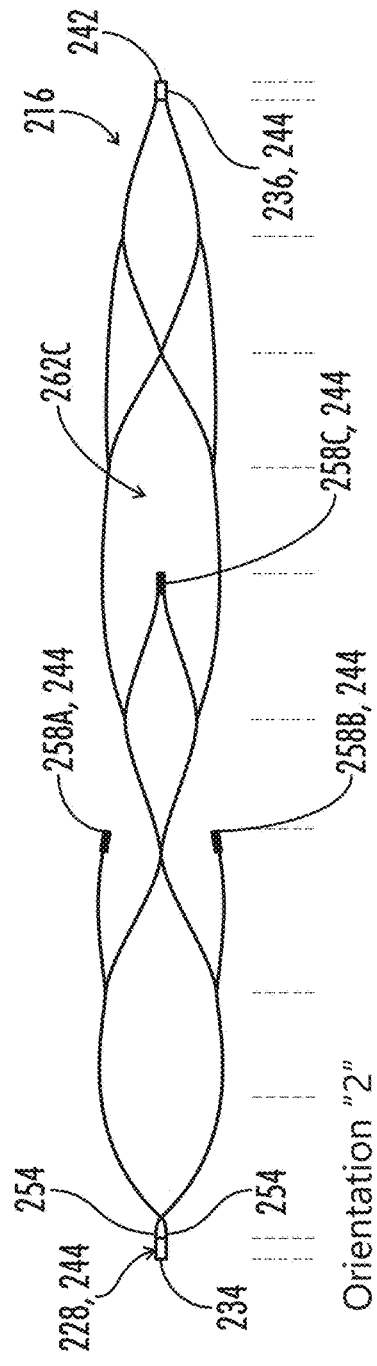
FIG. 20C illustrates a second, perspective view of the distal body manufactured from the native tube of FIG. 20A; the distal body is in Orientation 2.
Figure 21:
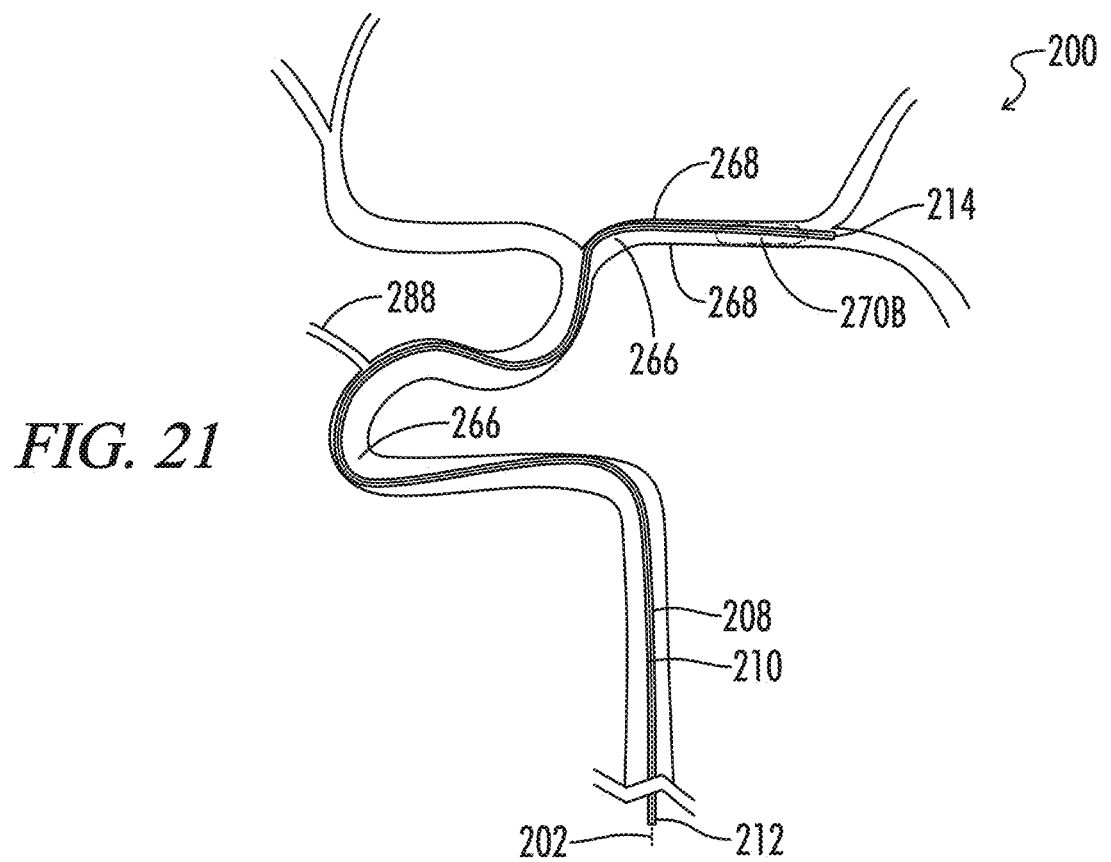
FIG. 21 shows a perspective view of a clot retrieval system that includes the distal body of FIGS. 20B-C being delivered in a blood vessel using a delivery catheter.

FIGS. 20A, 20B and 20C show a distal body 216 that is similar to the distal body 216 of FIGS. 14A, 14B and 14C except that the distal body 216 of FIGS. 20A, 20B and 20C is slightly shorter and its unattached, distal-pointing crowns 258A, 258B, 258C, and 258D are closer to the proximal tube 228. The shortened distal body 216 of FIGS. 20A, 20B and 20C is particularly adapted for tortuous blood vessels 266. FIG. 21-29 show stepwise deployment of the distal body 216 of FIGS. 20A, 20B and 20C in use with a manual (i.e., hand-operated), volume-dependent (i.e. volume locked) suction catheter 272 that is locked at between about 10 to about 60 cubic centimeters (cc). Optionally, the suction catheter 272 has an outer diameter of between about 0.05 inches and about 0.09 inches and its outer diameter is substantially larger than the outer diameter of the delivery catheter 208. The clot 270 is located in the vessel 266 through the use of, for example, contrast dye injected proximal and distal to the clot 270. As shown in FIG. 21, a delivery catheter 208 containing the distal body 216 of FIGS. 20A, 20B and 20C is positioned in the tortuous vessel 266 distal to the clot 270. The delivery catheter 208 is withdrawn, deploying the distal body 216. See FIG. 22. The distal body 216 is moved proximally relative to the clot 270 and tension is exerted on pull wire 202. See FIG. 23. While maintaining tension on the pull wire 202, a suction catheter 272 having a proximal end 274 and a distal end 276 is delivered over the pull wire 202 that is attached to the distal body 216. See FIG. 24. (The reason for exerting tension on the pull wire 202 is that the pull wire 202 serves as the guide/track for the movement of the suction catheter 272 and without tension, the suction catheter 272 and pull wire 202 could end up in the ophthalmic artery 288). The distal end 276 of the suction catheter 272 is positioned against the clot 270. A syringe 278 is attached to the suction catheter 272 using a rotating hemostatic valve 290, which allows the surgeon to aspirate while a pull wire 202 is in the system. The surgeon aspirates the syringe 278 by pulling back on the lever 280 to a mark on the base 282 corresponding to between about 10 and about 60 cubic centimeters of fluid. The surgeon then locks the lever 280 (and attached plunger) into place, leaving the suction catheter 272 under suction. The surgeon captures the clot 270 in the distal body 216 using the techniques described in FIGS. 15-19. The distal body 216 and clot 270 become captured by the suction catheter 272. See FIGS. 27 and 28. The surgeon then removes the suction catheter 272 and the distal body 216 and the clot 270, captured by the suction catheter 272, by moving the suction catheter 272 proximally out of the vessel 266. See FIG. 29. It is believed that the suction catheter 272 would be helpful in the event that a small portion of the clot 270 breaks off when retrieving the clot 270 using the distal body 216.

To examine effectiveness of the systems 200, the systems 200 of FIGS. 11-20, without the use of a suction catheter 272, were used to retrieve soft and hard clots 270A and 270B induced in a pig weighing between 30 to 50 kg. The weight of the pig was chosen so that the size of its vessels 266 would be approximate to the size of a human vessel. The pig was anesthetized. Several hard clots 270B were prepared by mixing pig blood and barium and incubating the mixture for 2 hours. Several soft clots 270A were prepared by mixing pig blood, thrombin and barium and incubating the mixture for 1 hour. The clots 270A and 270B, each of which had a width of 4 to 6 mm and a length of 10 to 40 mm, were then inserted into a vessel 266 having a diameter of 2 to 4 mm. (Only one clot 270A and 270B was located in the vessel 266 at a time). Angiograms were then performed to confirm occlusion. After waiting ten minutes after confirming occlusion, the distal bodies 216 of FIGS. 11-20 were then delivered distal to the clots 270A and 270B as described above and were used to retrieve the clots 270A and 270B as described in FIGS. 11-19. In each case, the distal bodies 216 were successful in retrieving the clots 270A and 270B. As shown, the distal body height in the relaxed state tapers/decreases as the proximal strips 252 approach the proximal hub/junction/tube 228 and also tapers/decreases as the basket strips 291 located at the distal end 220 of the basket 246 converge at the distal hub/junction/tube 236.

Figure 32:
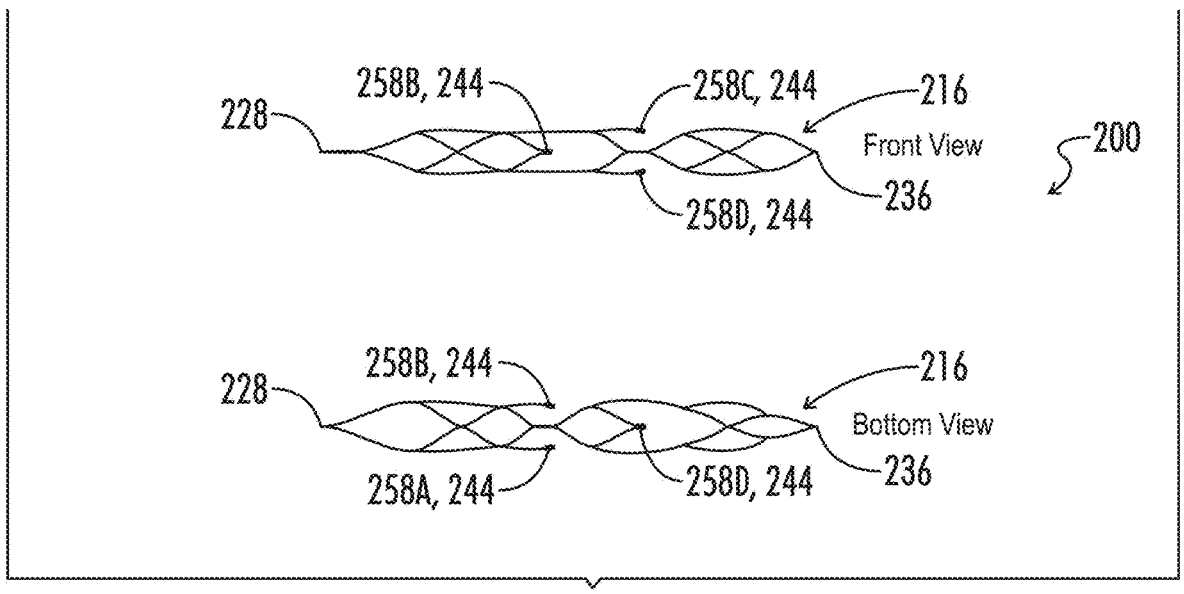
FIG. 32 illustrates an alternate embodiment of a distal body; in the distal body of FIG. 32, the proximal strips converge and are soldered or welded at the proximal hub/junction and the basket strips located at the distal end of the basket converge and are soldered or welded at the distal hub/junction.

The Alternate Embodiment of FIG. 32

FIG. 32 shows a distal body 216 in which the proximal strips proximal ends 254 converge and are soldered or welded at the proximal hub/junction 228 and the basket strips 291 located at the distal end 220 of the basket 246 converge and are soldered or welded at the distal hub/junction 236. To create such an embodiment, the distal body 216 may be prepared from a single tube, as described above, and the proximal and distal tubes may be clipped and the proximal ends 254 of the proximal strips 252 soldered or welded together (and optionally to the pull wire 202) and the basket strips 291 located at the distal end 220 of the basket 246 may also be welded or soldered or welded together. Optionally, the proximal and distal hubs/junctions 228 and 236 may include x-ray markers 244 as described above.

The Alternate Embodiments of FIGS. 33-35

Figure 33A:
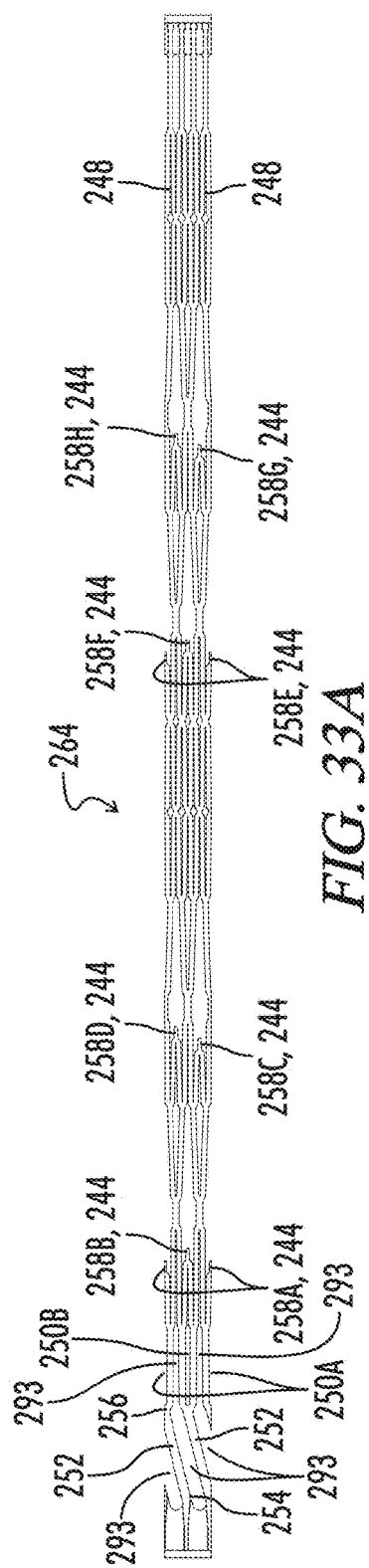
FIG. 33A illustrates a native memory metal tube used to manufacture a distal body of another embodiment of the present invention; the native tube has been rolled out flat and the lines in the tube indicate where the tube has been cut by a laser.
Figure 33B:
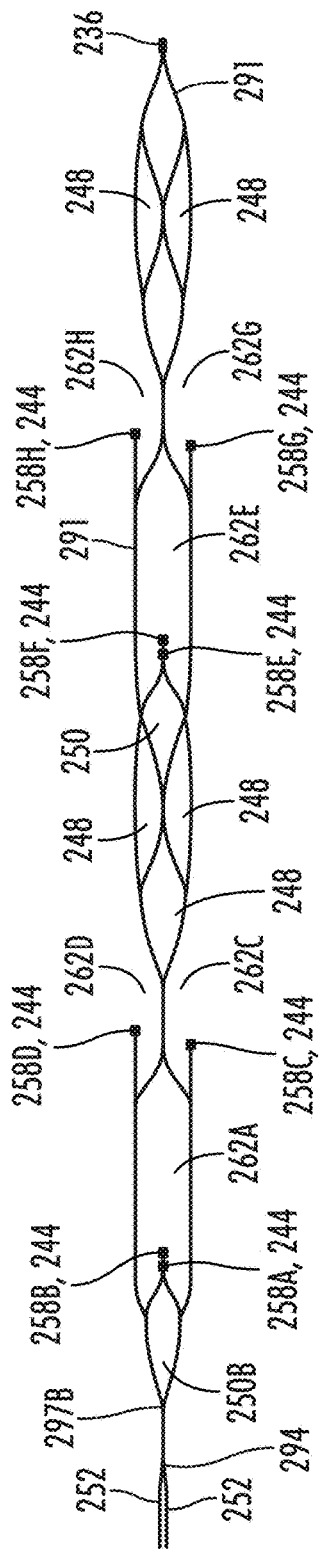
FIG. 33B illustrates a first, perspective view of the distal body manufactured from the native tube of FIG. 33A.
Figure 33C:
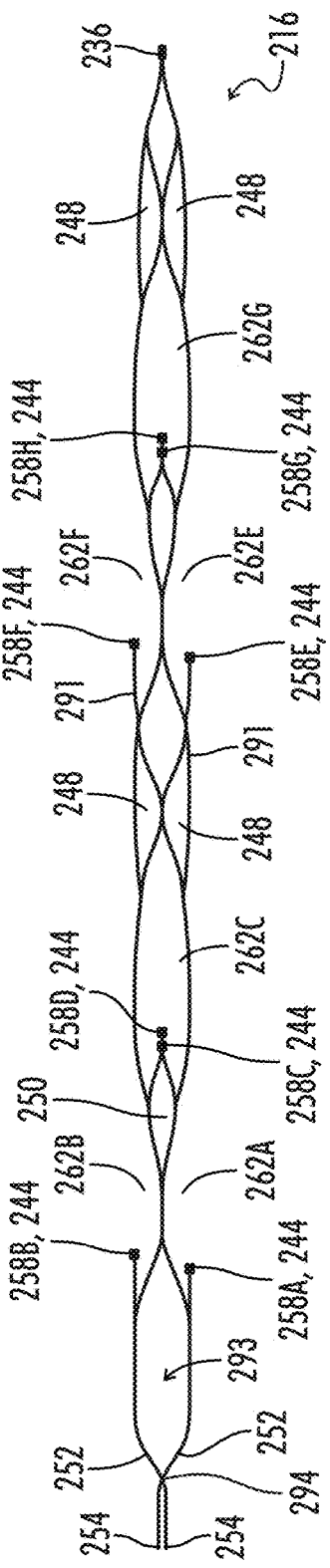
FIG. 33C illustrates a second, perspective view of the distal body manufactured from the native tube of FIG. 33A.

FIGS. 33A-33C and FIGS. 34A-34B (and the close-up views shown in FIGS. 35A and 35B) show an alternate embodiment in which no cells are proximal to the proximal-most cells 250A and 250B that have a free distal crown 258A and 258B. (FIGS. 33A-35B do not show the pull wire or catheter, both of which are preferably used with the distal body 216 and shown elsewhere, e.g., in FIGS. 11-20, and FIGS. 33B-33C and FIG. 35A-35B do not show the proximal hub 228). FIGS. 33A-33C has four pair of cells (only a few such cells are labeled with 250 or 250B and visible) with free distal-pointing crowns 258A-258H, which create four pairs of enlarged openings 262A-262H. FIGS. 34A-34B has five pair of cells (again not all labeled) with free distal-pointing crowns 258A-258J, which create five pairs of enlarged openings 262A-262J. More particularly, like FIGS. 11-20, in FIGS. 33A-33C and FIGS. 34A-34B, the distal body 216 has a proximal pair of free distal crowns 258A and 258B that have x-ray markers 244 and are located approximately the same distance from the proximal junction 228 and between 150 degrees and 180 degrees apart and then a second pair of free distal crowns 258C and 258D that have x-ray markers 244, and are located distal to the proximal pair of free distal crowns 258A and 258B. Like FIGS. 11-20, in FIGS. 33A-33C and FIGS. 34A-34B, the second pair of distal crowns 258C and 258D are located approximately the same distance from the proximal junction 228, are located between 150 degrees and 180 degrees apart and are located between about 60 degrees and about 90 degrees relative to the proximal pair of free distal crowns 258A and 258B.

The embodiments of FIGS. 33A-33C, FIGS. 34A-34B and FIGS. 35A-35B have several additional features. For example, in FIGS. 33A-33C, FIGS. 34A-34B, and FIGS. 35A-35B, the proximal pair of cells 250A and 250B having free distal crowns 258A and 258B each have a proximal crown 297A and 297B attached to a proximal strip 252. In FIGS. 33A-33C and FIGS. 34A-34B, distal to the second pair of free distal crowns 258C and 258D, the distal body 216 has a third pair of free distal crowns 258E and 258F that have x-ray markers 244, are located approximately the same distance from the proximal junction 228 and are located between 150 degrees and 180 degrees apart and are located between about 60 degrees and about 90 degrees relative to the second pair of free distal crowns 258C and 258D. In FIGS. 33A-33C and FIGS. 34A-34B, distal to the third pair of free distal crowns 258E and 258F, the distal body 216 also has a fourth pair of free distal crowns 258G and 258H that have x-ray markers 244, are located approximately the same distance from the proximal junction 228 and are located between 150 degrees and 180 degrees apart and are located between about 60 degrees and about 90 degrees relative to the third pair of free distal crowns 258E and 258F. In FIGS. 34A-34B, distal to the fourth pair of free distal crowns 258G and 258H, the distal body 216 also has a fifth pair of free distal crowns 258I and 258J that have x-ray markers 244, are located approximately the same distance from the proximal junction 228 and are located between 150 degrees and 180 degrees apart and are located between about 60 degrees and about 90 degrees relative to the fourth pair of free distal crowns 258G and 258H. An advantage having eight unattached distal-pointing crowns 258A-258H that are sequentially offset (as in FIGS. 33A-33C) and ten unattached distal-pointing crowns 258A-258J that are sequentially offset (as in FIGS. 34A-34B) is that each free distal crown 258A-258J creates an enlarged cell 262A-262J. Thus, in FIGS. 33A-33C and FIGS. 34A-34B, eight and ten, respectively, sequentially offset enlarged cells 262A-262H are formed, creating multiple clot entry points. In FIG. 34A-34B, with the exception of the enlarged cells 262A-262H, all of the cells located between the cells 250A and 250B (250A is hidden in FIGS. 34A-34B but shown in FIGS. 35A-35B) having the proximal pair of free distal crowns 258A and 258B and the cells having the distal-most pair of free distal crowns 258I and 258J have free distal crowns. Indeed, with the exception of the enlarged cells 262A-262H, all of the cells located between proximal-most free-distal crowns 258A and 258B and distal-most free crowns 258I and 258J have free distal crowns 258C-258H. By contrast, the distal body 216 of FIGS. 33A-33C has an intermediate group of cells 248 (i.e., a stent-like structure) with non-free distal crowns (distal crowns that are attached to a basket strip 291) between the second pair of enlarged openings 262C and 262D and the third pair of enlarged openings 262E and 262F. In FIG. 34A-34B, all of the cells 248 having distal crowns that are attached to a basket strip 291 are located at the distal end of the distal body 216 (i.e., distal to the distal-most enlarged openings 262G and 262H) to create a substantially closed distal end of the basket 246 to capture the clot.

Figure 35A:
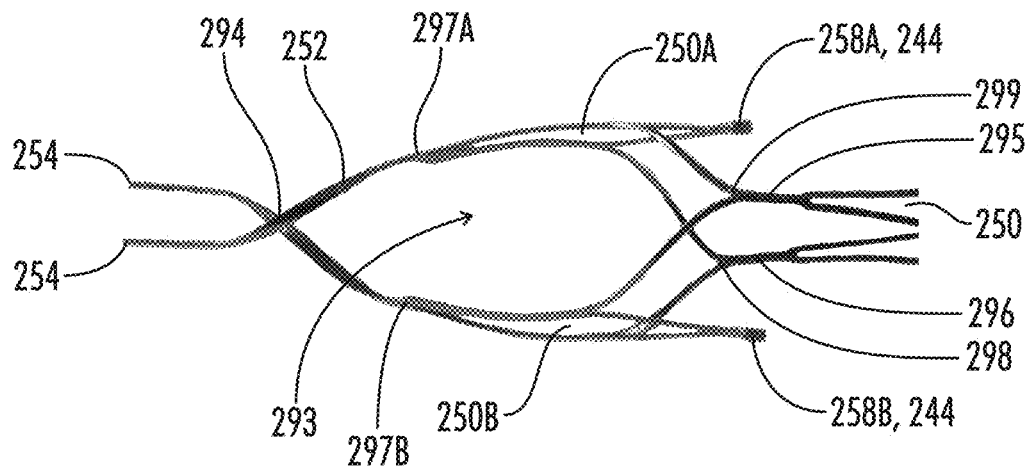
FIG. 35A illustrates a first, perspective view of a proximal portion of a distal body of another embodiment of the present invention.
Figure 35B:
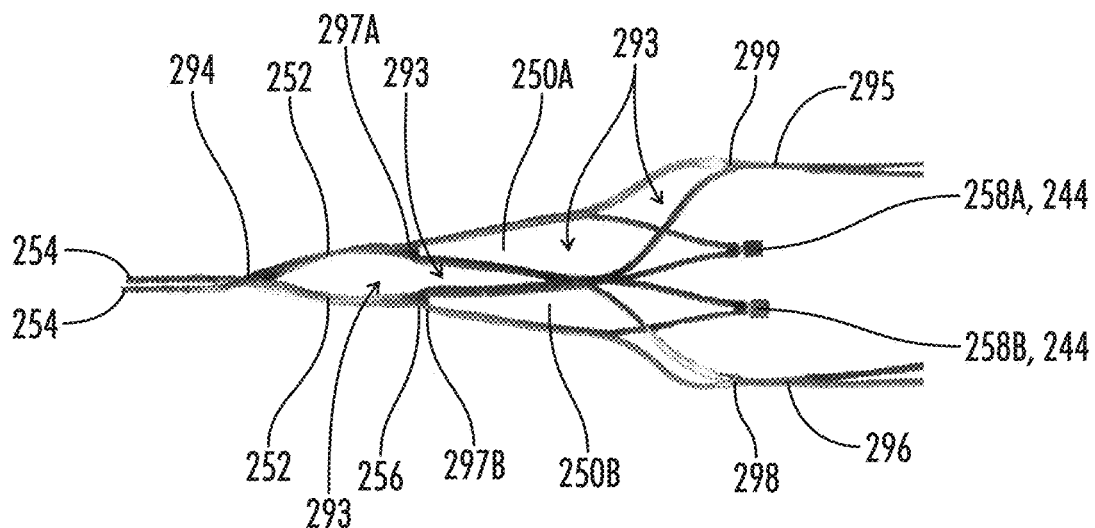
FIG. 35B illustrates a second, perspective view of the proximal portion of the distal body of FIG. 35A.

In addition, in FIGS. 33A-33C, 34A-34B, FIGS. 35A-35B, the distal body 216 has two proximal three-dimensional openings 293 that are located 180 degrees apart, as best seen in FIG. 33C and FIG. 34A and the close-up views of FIGS. 35A and 35B. (The proximal three-dimensional openings 293 are aligned and create a continuous void). One such three-dimensional opening 293 has a proximal end at the intersection point 294 of the proximal strips 252 and a distal end at a distal crown 299 attached to a first strut 295 located (lengthwise) approximately the same distance from the proximal hub/junction 228 as the free distal crowns 258A and 258B of the first pair of free distal crowns. The other such three-dimensional opening 293 is on the other side of the distal body 216 and has a proximal end at the intersection point 294 of the proximal strips 252 and a distal end at another distal crown 298 attached to a second strut 296 that is also located (lengthwise) approximately the same distance from the proximal hub/junction 228 as the free distal crowns 258A and 258B of the first pair of free distal crowns. The second strut 296 is located 180 degrees from the first strut 295. As shown in FIG. 35A, the intersection point 294 of the proximal strips 252 may be located approximately in the widthwise and heightwise center of the distal body 216 and the proximal crowns 297A and 297B of the proximal-most cells 250A and 250B having the free distal crowns 258A and 258B may be located approximately 150 degrees to 180 degrees apart (e.g., at the 12 o'clock and 6 o'clock positions as shown in FIG. 35A and the 3 o'clock and 9 o'clock positions in FIG. 35B) and at the maximum height/width of the distal body 216. The proximal crowns 297A and 297B of the proximal-most cells 250A and 250B having the free distal crowns 258A and 258B also are attached to the proximal strips 252 as shown in FIGS. 35A and 35B. Similarly, the bridge memory metal strips (distal struts) 295 and 296 may be located approximately 150 degrees to 180 degrees apart (e.g., at the 3 o'clock and 9 o'clock positions as shown in FIG. 35A and the 12 o'clock and 6 o'clock positions in FIG. 35B), at the maximum height/width of the distal body 216, and approximately 60 degrees to 90 degrees relative to the free distal crowns 258A and 258B.

The Embodiments of FIGS. 36-37

FIGS. 36A-36N and 37A-37K (also referred to herein as FIGS. 36-37 for brevity) show alternate embodiments of distal bodies 216 that are similar to the embodiments of FIGS. 11-35. The distal bodies 216 may be made by any method known in the art including but not limited to those described in U.S. Pat. No. 9,566,412, the entire contents of which are incorporated herein by reference.

FIGS. 36-37 are CAD drawings drawn to scale. However, it will be appreciated that other dimensions are possible.

More particularly, FIGS. 36-37 provide a system for removing objects from an interior lumen of an animal. The system may include, as previously described, a pull wire 202 having a proximal end (not shown in FIGS. 36-37) and a distal end 206. The system of FIGS. 36-37 also includes a distal body 216 that may be attached to the pull wire 202, preferably the pull wire distal end 206. As with the prior embodiments of FIGS. 11-35, the distal body 216 may include an interior 222, a perimeter 300, a proximal end 218, a distal end 220, a distal body length 226 extending from the proximal end 218 to the distal end 220, a proximal junction/hub/tube 228 that may be attached to the pull wire 202 and may form the proximal end 218 of the distal body 216, a plurality of proximal strips 252, a basket 246 comprised of a plurality of cells formed by a plurality of basket strips 291, and a distal junction/hub/tube 236 forming a distal end 302 of the basket 246. As with the prior embodiments of FIGS. 11-35, the basket 246 may include a basket interior 346, each proximal strip 252 may have a distal end 256 attached to a cell and a proximal end 254, the proximal ends 254 of the proximal strips 252 may converge at the proximal junction 228. As with the prior embodiments of FIGS. 11-35, the distal body 216 may have a relaxed state wherein the distal body 216 has a first height 224 and a first width 225, and a collapsed state (not shown in FIGS. 36-37) wherein the distal body 216 has a second height and a second width, the second height less than the first height 224, the second width less than the first width 225. As with prior embodiments, in the embodiments of FIGS. 36-37, the proximal strips 252 and the basket strips 291 are preferably comprised of a memory metal.

Like the embodiments of FIGS. 33-35, in the embodiments of FIGS. 36-37, in the relaxed state, the basket 246 may include a series of at least three pair of cells 250A-250F located on the distal body perimeter 300 having a proximal crown 260 pointing generally in the proximal direction and attached to a memory metal strip (either a proximal strip 252 or basket strip 291) and a free distal crown 258A-258F pointing generally in the distal direction. Optionally, as shown in FIGS. 36-37, in the series, the proximal-most free distal crowns 258A, 258B are located at the 12 and 6 o'clock positions and located about the same distance from the proximal junction 228, the next proximal-most free distal crowns 258C, 258D are located at the 3 and 9 o'clock positions and located about the same distance from the proximal junction 228, and the succeeding proximal-most free distal crowns 258E, 258F are located at the 12 and 6 o'clock positions (i.e., substantially aligned with proximal-most free distal crowns 258A, 258B) and located about the same distance from the proximal junction 228. Optionally, each free distal crown 250A-250F forms part of a different enlarged cell 262A-262F that is configured to allow a thrombus to enter the basket interior 346. In other words, like the prior embodiments, the enlarged cells 262A-262F are designed to capture a clot/thrombus. In the proximal and distal end views of FIGS. 36M, 36N, 37H, and 37I, miniature clocks with clock hands are used to illustrate the 12, 3, 6 and 9 o'clock positions.

For purposes of FIGS. 36-37, when it is said that a component, such as a free distal crown 258A-258J, is located "about the same distance from the proximal junction" 228, if one component (e.g., one free distal crown 258A of the pair of proximal-most free distal crowns 258A/258B) is located X distance from the proximal junction 228, the other component (e.g., the other free distal crown 258B of the pair of proximal-most free distal crowns 258A/258B) is located X distance plus or minus (+/−) 5 millimeters (mm) from the proximal junction 228. In a preferred embodiment, the other component is located X distance plus or minus (+/−) 3 mm from the proximal junction 228, more preferably X distance plus or minus (+/−) 0.5 mm from the proximal junction 228. (The same relationship will hold true for the other pairs of free distal crowns 258C-258F in the series— e.g., if one free distal crown 258C of the next proximal-most pair of free distal crowns 258C/258D is located Y distance from the proximal junction 228, the other free distal crown 258D of the next proximal-most pair of free distal crowns 258C/258D is located Y distance plus or minus (+/−) 5 mm from the proximal junction 228. Again, more preferably the other component is located Y distance plus or minus (+/−) 3 mm from the proximal junction 228, more preferably Y distance plus or minus (+/−) 0.5 mm from the proximal junction 228. The same relationship holds true from 258E and 258F.

In FIG. 37, like the embodiment of FIG. 34, the series includes at least five pair of cells 250A-250J located on the distal body perimeter 300 having a proximal crown 260 pointing generally in the proximal direction and attached to a memory metal strip (either a proximal strip 252 or basket strip 291) and a free distal crown 258A-258J pointing generally in the distal direction, and in the series, after the succeeding free distal crowns 258E, 258F, the next proximal-most free distal crowns 258G, 258H are located at the 3 and 9 o'clock positions and located about the same distance from the proximal junction 228 and form enlarged cells 262G, 262H, and the distal-most free distal crowns 258I, 258J are located at the 12 and 6 o'clock positions and located about the same distance from the proximal junction 228 and form the most distally-located enlarged cells 262I, 262J. Again, about the same distance from the proximal hub 228, means the same distance+/−5 mm from the proximal junction 228. In a preferred embodiment, 258G/258H are located the same distance+/−3 mm from the proximal junction 228, more preferably the same distance+/−0.5 mm from the proximal junction. The same relationship holds true from 258I and 258J.

As with prior embodiments, FIGS. 36-37 illustrate that in the relaxed state, the basket 246 may comprise a plurality of distal cells 248D distal to the distal-most free distal crown (i.e. 258E, 258F in FIGS. 36 and 258I, 258J in FIG. 37) that have a proximal crown attached to another cell of the basket 246 and pointing generally in the proximal direction and a distal crown pointing generally in the distal direction and attached to the distal junction 236. In other words, the distal cells 248D are designed to retain a clot/thrombus in the basket interior 346.

As with prior embodiments, FIGS. 36-37 illustrate that, in the relaxed state, each enlarged cell 262A-262J may have a proximal end 308 that may be comprised of two proximal crowns pointing generally in the proximal direction, a distal end 310 that may comprise a distal crown pointing generally in the distal direction, and a length 312 extending from the proximal end 308 to the distal end 310 of the respective enlarged cell 262A-262J.

As with prior embodiments, FIGS. 36-37 illustrate that in the relaxed state, each distal cell 248D may have a length 314 extending from the proximal crown to the distal crown 307 of the respective distal cell 248D.

As with prior embodiments, FIGS. 36-37, and particularly FIG. 36J, illustrate that in the relaxed state, each of the enlarged cells 262A-262J may be longer than each of the distal cells 248D.

As with prior embodiments, FIGS. 36-37, and particularly FIG. 36J, illustrate that in the relaxed state, for each of the enlarged cells 262A-262J, the distance 316 from the proximal end 308 of the enlarged cell 262A-262J to the free distal crown 258A-258J of the enlarged cell 262A-262J may be less than the distance 318 from the free distal crown 258A-258J of the enlarged cell 262A-262J to the distal end 310 of the enlarged cell 262A-262J. In other words, the free distal crowns 258A-258J do not protrude far enough into the enlarged cells 262A-262J to prevent a clot from entering the basket interior 346 through the enlarged cells 262A-262J.

As with prior embodiments, FIGS. 36-37 illustrate that the distal body 216 may further comprise a lead wire 286 extending distally from the distal junction 236. As with prior embodiments but not shown in FIGS. 36-37, the system may further comprise a catheter having an interior, a proximal end leading to the interior and a distal end leading to the interior, the catheter comprised of a biocompatible material and configured to envelop the distal body 216 when the distal body 216 is in the collapsed state. Deployment and use of the system may be as shown in FIGS. 15-29.

As with prior embodiments, FIGS. 36-37 illustrate that in the relaxed state, the basket 246 preferably does not have any free crowns that point generally in the proximal direction, as free proximal crowns could damage the vessel as mentioned previously.

As with prior embodiments, FIGS. 36-37 illustrate that the distal body 216, in the relaxed state, may comprise a distal tapered region 322 in which the distal body height 224 and width 225 decrease as the basket 246 approaches the distal junction 236.

As with prior embodiments, FIGS. 36-37 illustrate that the distal body 216, in the relaxed state may comprise a proximal tapered region 320 in which the distal body height 224 and width 225 decrease as the proximal strips 252 approach the proximal junction 228. It will be appreciated that the tapering of the proximal region 320 may take on a variety of shapes as shown in FIGS. 36 and 37.

As with prior embodiments, FIGS. 36-37 illustrate that in the relaxed state, each of the enlarged cells 262A-262J may be longer than each of the pair of cells 250A-250J.

As with prior embodiments, FIGS. 36-37 illustrate that in the relaxed state, each of the enlarged cells 262A-262J may extend from the 6 o'clock position to the 12 o'clock position or the 3 o'clock position to the 9 o'clock position, as best seen in the close-up views of FIGS. 36C, 36E and 36F and 37G but also shown in FIGS. 36A-36B, 36I-36L, 37A-37F.

As with the prior embodiments of FIGS. 11-19 and 21-32, FIG. 36 illustrates that in the relaxed state the basket 246 may further comprise a plurality of proximal cells 342 proximal to the proximal-most free distal crowns 258A, 258B, the plurality of proximal cells 342 having a proximal crown attached to the proximal junction 228 and pointing generally in the proximal direction and a distal crown pointing generally in the distal direction and attached to another cell of the basket 246. However, such proximal cells 342 are optional and not shown in FIG. 37, due to the length of the basket 246 which includes ten enlarged cells 262A-262J. If the proximal cells 342 are not included, optionally, as with the prior embodiments of FIGS. 20 and 33-35, FIG. 37 illustrates that in the relaxed state the proximal crowns of the cells 250A, 250B comprising the proximal-most free distal crowns 258A, 258B may be attached to the distal ends 256 of the proximal strips 252. Without being bound by any particular theory, a purpose of the proximal cells 342 may be to allow the clot to rest on the proximal cells 342 prior to entering through the enlarged cells 262A-262J.

In preliminary clot capture animal studies using a swine thrombectomy model, it has been observed the distal body 216 of FIG. 37 is particularly adept at capturing a clot. (Preliminary clot capture animal studies were performed using conditions similar to that described in Ulm et al., Preclinical Evaluation of the NeVa™ Stent Retriever: Safety and Efficacy in the Swine Thrombectomy Model, Interv Neurol. 2018 April; 7(5):205-217). Without being bound by any particular theory, it is believed that the clot capture ability of the distal body 216 of FIG. 37 is due to the minimal interference at the enlarged cells 262A-262J (i.e., that the basket strips 291 are flared apart at the distal crowns located at the distal ends 310 of the enlarged cells 262A-262J).

Thus, as shown in FIG. 37, in the relaxed state, for at least some enlarged cells 262A-262J (preferably for most, more preferably for each enlarged cell 262A-262J), two basket strips 291 meet to form the distal crown located at the distal end 310 of the enlarged cell 262A-262J, and the two basket strips 291 form an angle 328 greater than 65 degrees, more preferably greater than 70 degrees, more preferably greater than 75 degrees, more preferably greater than 80 degrees, more preferably greater than 85 degrees, more preferably greater than 90 degrees, more preferably greater than 95 degrees, more preferably greater than 100 degrees at the respective distal crown located at the distal end 310 of the enlarged cell 262A-262J. Preferably, the angle 328 is less than 150 degrees. It is believed that the flared nature of the basket strips 291 meeting at the distal crown at the distal end 310 of the enlarged cells 250A-250J assists in allowing the clot to enter the basket interior 346. By comparison, the basket strips 291 meeting to form the free distal crowns 258A-258J may have a much smaller angle 326 at the respective free distal crown 258A-258J, given that cells 250A-250J are not intended to be clot capture cells. For example, the angle 326 at the respective free distal crown 258A-258J may be less than 50 degrees, more preferably less than 45 degrees, more preferably less than 40 degrees. In other words, for some, most or all enlarged cells 262A-262J, the angle 328 at the distal crown at the distal end 310 may be at least 2 times (more preferably at least 2.5 times, more preferably at least 3 times) as large as the angle 326 at the free distal crown 258A-258J. Preferably, angle 328 is no more than 5 times as large as angle 326. Due to the symmetry of the distal body 216, the angle 326 at free distal crown 258A may be substantially the same as the angle 326 at free distal crown 258B, the angle 326 at free distal crown 258C may be substantially the same as the angle 326 at free distal crown 258D, the angle 326 at free distal crown 258E may be substantially the same as the angle 326 at free distal crown 258F, the angle 326 at free distal crown 258G may be substantially the same as the angle 326 at free distal crown 258H, the angle 326 at free distal crown 258I may be substantially the same as the angle 326 at free distal crown 258J. Similarly, the angle 328 at the distal crown at the distal end 310 of enlarged cell 262A may be substantially the same as the angle 328 at the distal crown of enlarged cell 262B, the angle 328 at the distal crown at the distal end 310 of enlarged cell 262C may be substantially the same as the angle 328 at the distal crown of enlarged cell 262D, the angle 328 at the distal crown at the distal end 310 of enlarged cell 262E may be substantially the same as the angle 328 at the distal crown of enlarged cell 262F, the angle 328 at the distal crown at the distal end 310 of enlarged cell 262G may be substantially the same as the angle 328 at the distal crown of enlarged cell 262H, and the angle 328 at the distal crown at the distal end 310 of enlarged cell 262I may be substantially the same as the angle 328 at the distal crown of enlarged cell 262J.

Because the basket strips 291 may be non-linear, the angles 326 and 328 may be determined as if the basket strips 291 were straight from their proximal ends 330 to their distal ends 332. (See dashed lines 350 and 355 in FIG. 37K). In other words, the angles 326 and 328 may be the average (mean) angle between the basket strips 291 along the basket strip lengths. In such measurements, the angles 326 and 328 are measured by drawing an arc between a point on each basket strip 291 at the same position along the distal body length 226. Alternatively, the angles 326 and 328 may be the maximum angle between the basket strips 291 along the basket strip lengths, drawing an arc between a point on each of the two basket strips 291 at the same position along the distal body length 226. See FIG. 37A, 37E, 37F, 37G for showing how arcs are drawn and maximum angles 326 and 328 are measured.

Figure 37A:
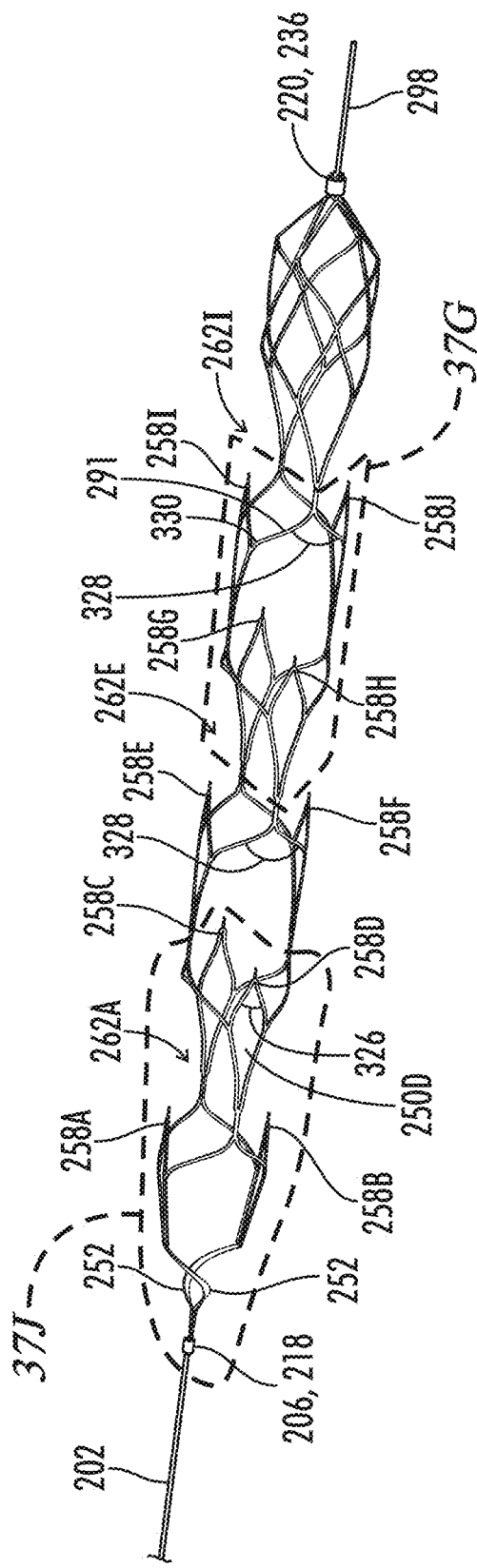
FIG. 37A illustrates a front perspective view of a distal body of another embodiment of the present invention.
Figure 37B:
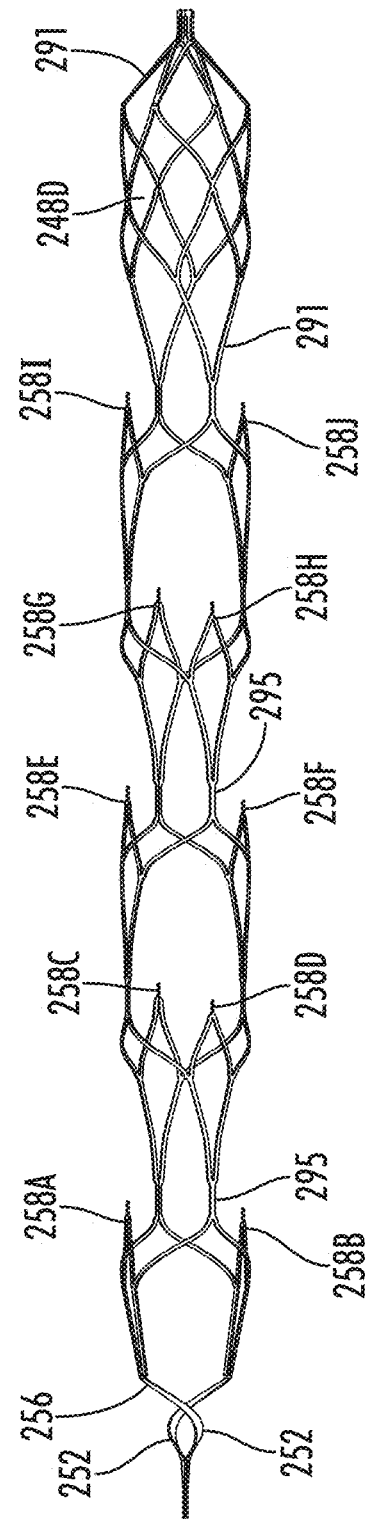
FIG. 37B illustrates another front perspective view of the distal body of FIG. 37A without the proximal and distal hubs/junctions and pull wire.
Figure 37C:
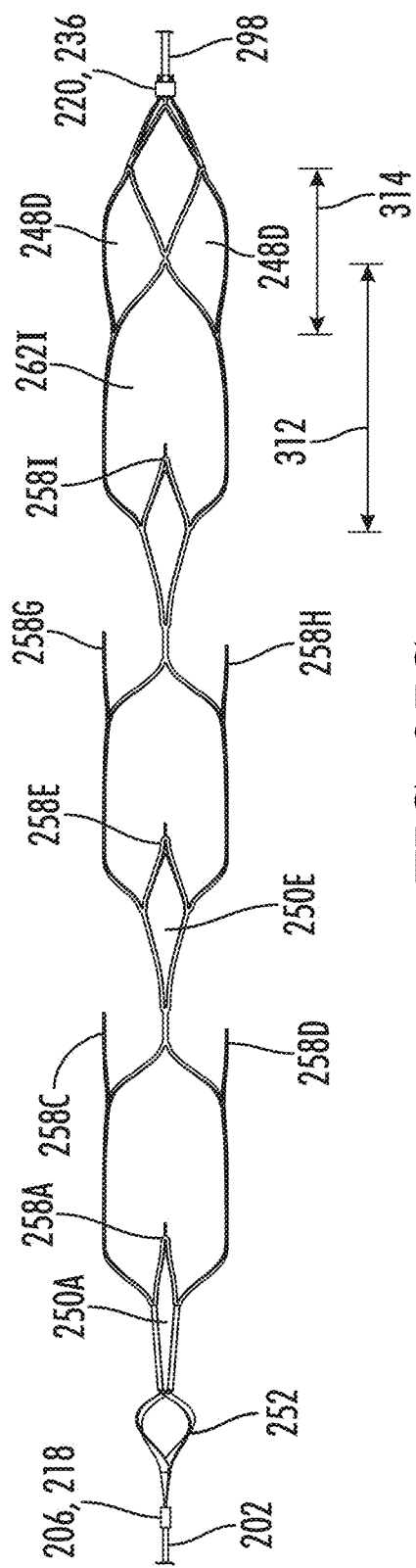
FIG. 37C illustrates a top plan view of the distal body of FIG. 37A.
Figure 37D:
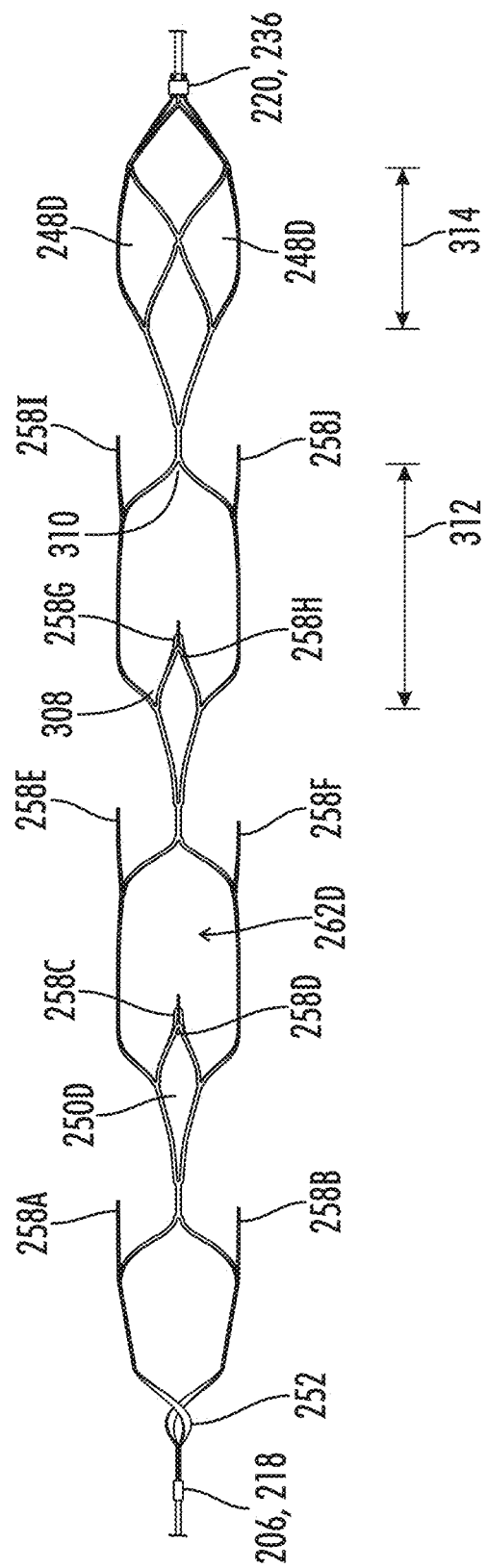
FIG. 37D illustrates a front elevation view of the distal body of FIG. 37A.
Figure 37G:
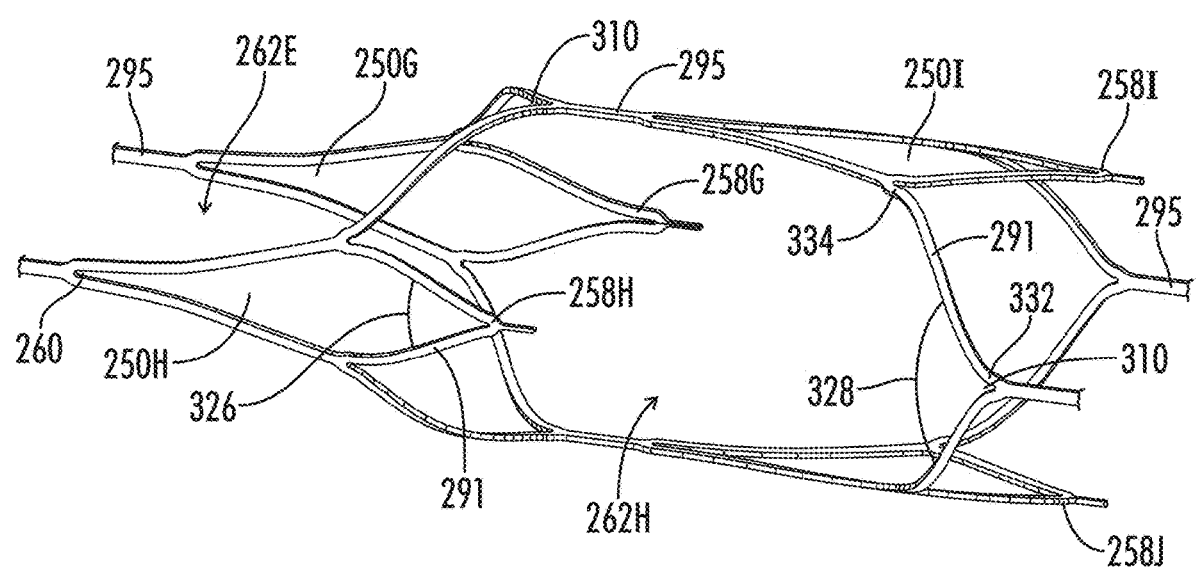
FIG. 37G illustrates an enlarged front elevation view of the area labeled 37G in FIG. 37A.
Figure 37H:
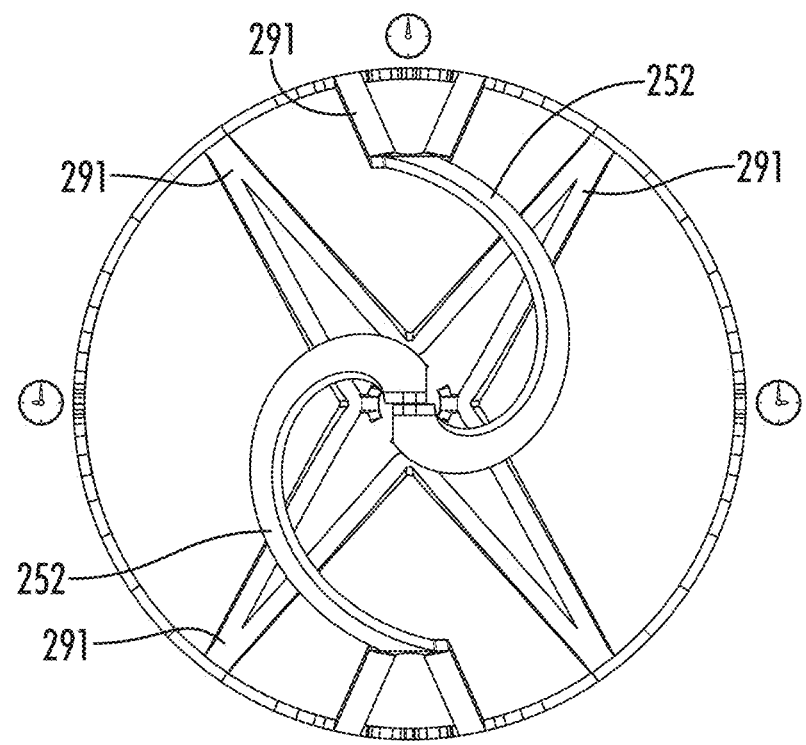
FIG. 37H illustrates a proximal elevation view of the distal body of FIG. 37A.
Figure 37I:
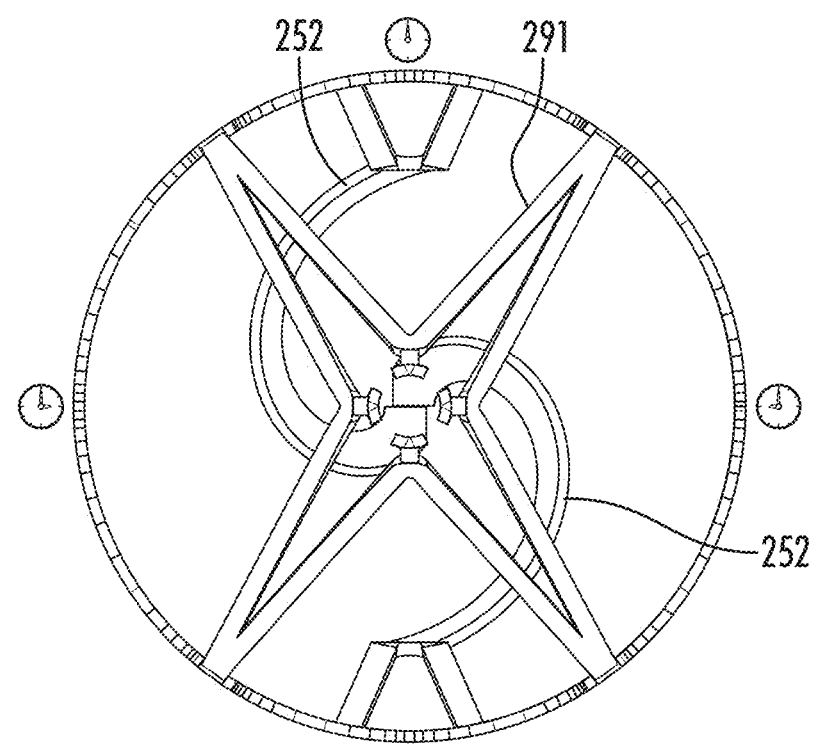
FIG. 37I illustrates a distal elevation view of the distal body of FIG. 37A.
Figure 37J:
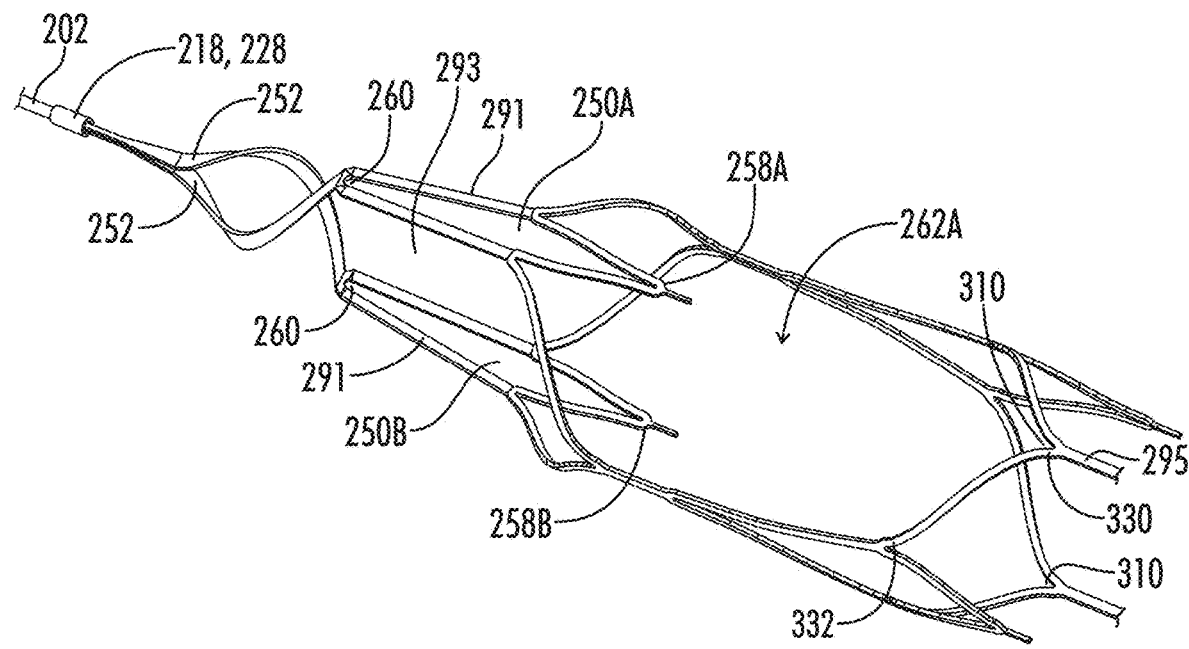
FIG. 37J illustrates an enlarged front perspective view of the area labeled 37J in FIG. 37A.

As an example, the maximum angles 328 between the basket strips 291 forming the distal crowns at the distal ends 310 of the enlarged cells 262C, 262F, and 262G, as illustrated in FIGS. 37E-37G, are approximately 100 degrees, whereas the maximum angles 326 between the basket strips 291 forming free distal crowns 258C, 258F, and 258G, as illustrated in FIGS. 37E-37G, by comparison are about 40 degrees. (It should be noted that the maximum angle 328 between the basket strips 291 forming the distal crown at the distal end 310 of distal-most enlarged cell 262J, as illustrated in FIG. 37E, is approximately 80 degrees, showing that there may be variability in the angles 326, 328).

Figure 37K:
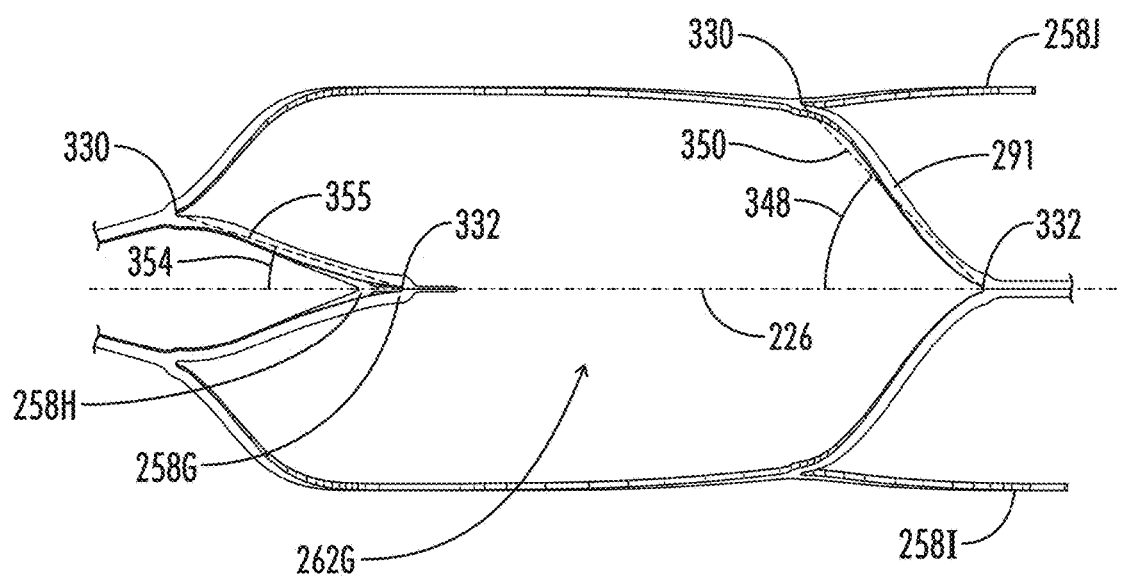
FIG. 37K illustrates an enlarged rear elevation view of the area labeled 37K in FIG. 37F.

Relatedly, optionally, in the relaxed state, each of the basket strips 291 meeting at the distal crown at the distal end 310 of some or all of the enlarged cells 250A-250J extends proximally from the respective distal crown at the distal end 310 at an angle 348 of at least 32.5 degrees, more preferably at least 35 degrees, more preferably at least 37.5 degrees, more preferably at least 40 degrees, more preferably at least 42.5 degrees, more preferably at least 45 degrees, more preferably at least 47.5 degrees, more preferably at least 50 degrees relative to a line bisecting the respective distal crown that is parallel to the distal body length 226 as best seen in FIG. 37K. The angle 348 may be determined by measuring the basket strip 291 as if it were straight from the proximal end 330 to the distal end 332. Thus, for example, each basket strip length, as measured from drawing a straight line from the proximal end 330 to the distal end 332 of the basket strip 291 may be at least 32.5 degrees, more preferably at least 35 degrees, more preferably at least 37.5 degrees, more preferably at least 40 degrees, more preferably at least 42.5 degrees, more preferably at least 45 degrees, more preferably at least 47.5 degrees, more preferably at least 50 degrees relative to a line bisecting the respective distal crown that is parallel to the distal body length 226 (as well as an adjacent bridge memory metal strip 336, which as explained herein may be substantially parallel to the distal body length 226). See FIG. 36K (dotted line 350 representing basket strip length, dotted line 226 drawn through the respective distal crown that is parallel to the distal body length 226, and angle 348 between the lines 350 and 226 measuring 45 degrees). Relatedly, for some, most or all the free distal crowns 258A-258J, the basket strip lengths, as measured from drawing a straight line from the proximal end 330 to the distal end 332 of the basket strip 291 may be less than 25 degrees, more preferably less than 22.5 degrees, more preferably less than 20 degrees relative to a line that bisects the free distal crowns 258A-258J and is parallel to the distal body length 226. See FIG. 36K (dotted line 355 representing basket strip length, dotted line 226 drawn through distal crown 258H that is parallel to the distal body length 226, and angle 354 between the lines 355 and 226 measuring 18 degrees at free distal crown 258H). Thus, for some, most or each enlarged cell 262A-262J, angle 348 at free distal crowns 258A-258J may be twice, more preferably 2.5 times, more preferably 3 times the size of angle 354.

Relatedly, in FIG. 37E, which shows a top plan view, the distal ends 332 of the basket strips 291 forming the distal crown of enlarged cell 262J are located approximately in the center of the distal body width 225 and the proximal ends 330 of the basket strips 291 are located approximately at the front and rear of the distal body 216. The proximal end 330 and distal ends 332 of the basket strips 291 meeting to form the distal crown located at the distal end 310 of enlarged cell 262H are also shown in the perspective view of FIG. 37G. Optionally, the lengths of each basket strip 291 meeting at the distal crown at the distal end 310 of some or all of the enlarged cells 250A-250J, as measured from their proximal ends 330 to their distal ends 332, may be approximately equal to ½ of the distal body width 225 and height 224.

Relatedly, optionally, as shown in the embodiment of FIG. 37 and best seen in FIGS. 37G and 37K, in the relaxed state, for at least some enlarged cells 262A-262J (preferably for each enlarged cell 262A-262J), in the relaxed state, the two basket strips 291 meeting to form the distal crown located at the distal end 310 of the enlarged cell 262A-262J may have distal ends 332 meeting at the respective distal crown and located approximately in the center of the distal body height 224 or width 225 and a proximal end 330 attached to another cell of the basket 246 and located approximately at the top, bottom or front side, or rear side of the distal body 216. In other words, in FIGS. 37F and 37K, which show front and rear elevation views, the distal ends 332 of the basket strips 291 forming the distal crown of enlarged cells 262G and 262H are located approximately in the center of the distal body height 224 and the proximal ends 330 of the basket strips 291 are located approximately at the top and bottom of the distal body 216.

As with the prior embodiments of FIGS. 34A-34B, in the distal body 216 of FIG. 37, as seen in FIGS. 37E-37F for example, in the relaxed state, due to the space occupied by the ten enlarged cells 250A-250J, from at least the proximal crowns 260 of the cells 250C, 250D comprising the next proximal-most free distal crowns 258C, 258D to the proximal ends 308 of the enlarged cells 262I, 262J formed by the distal-most pair of free distal crowns 258I, 258J, the basket 246 has no cells other than the enlarged cells 262A-262J and the cells 250C-250J comprising the free distal crowns 258C-258J.

In the distal body 216 of FIG. 36, in the relaxed state, due to the space occupied by the six enlarged cells 250A-250F, as seen in FIGS. 37E-37F for example, from at least the proximal crowns 260 of the cells 250C, 250D comprising the next proximal-most free distal crowns 258B, 258C to the proximal ends 308 of the enlarged cells 262E, 262F formed by the succeeding pair of free distal crowns 258E, 258F the basket 246 has no cells other than the enlarged cells 250A-250F and the cells 262C-262F comprising the free distal crowns 258C-258F.

The distal bodies 216 may be substantially symmetrical from front to rear and bottom to top, as shown in FIGS. 36I-36L and 37C-37F for example.

As with prior embodiments, FIGS. 36-37 illustrate that in the relaxed state, the distal crowns located at the distal end 310 of the enlarged cells 250A-250J may be attached to another cell of basket 246 (i.e., are not free floating).

Figure 36C:
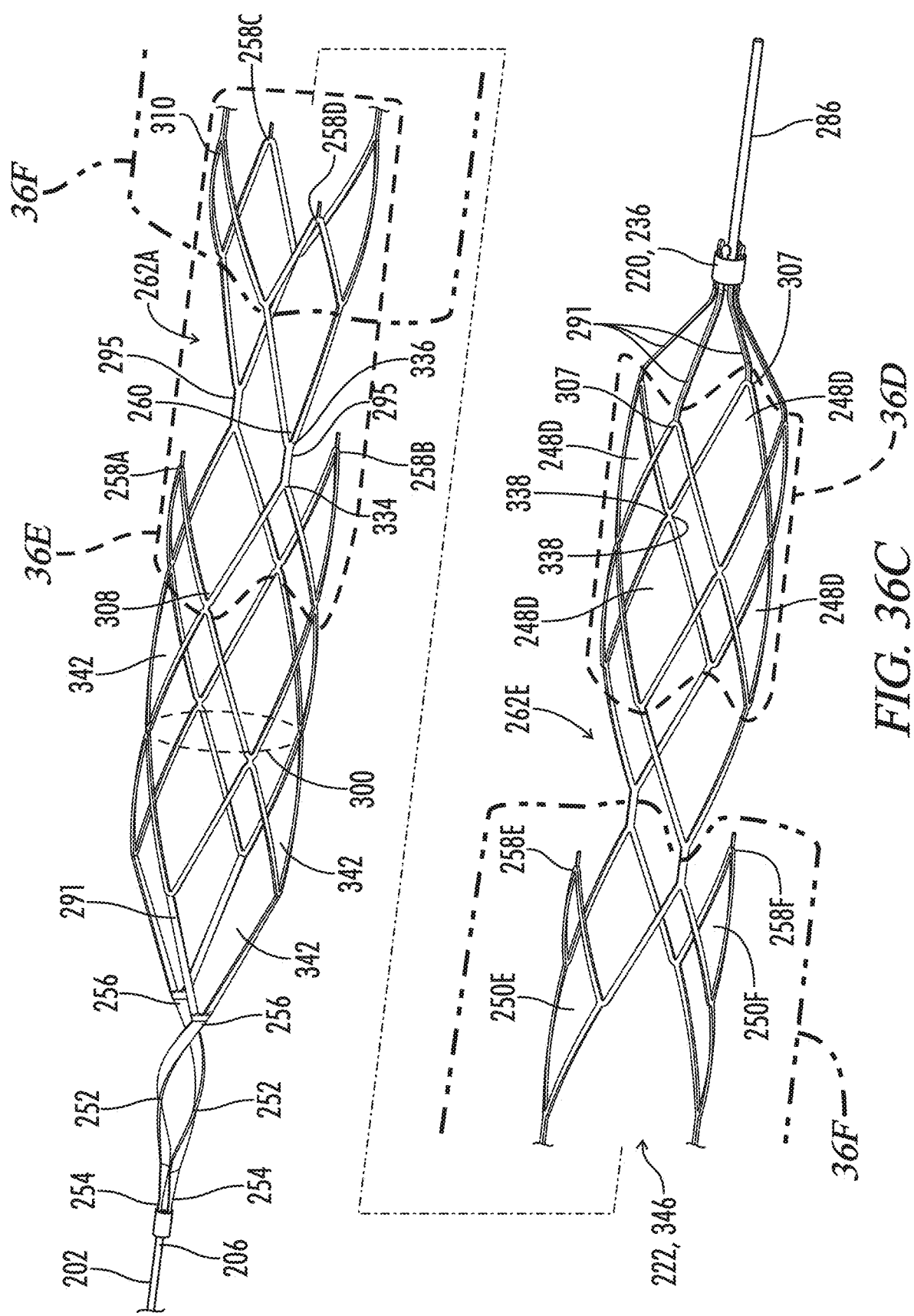
FIG. 36C illustrates an enlarged front perspective view of the distal body of FIG. 36A.
Figure 36D:
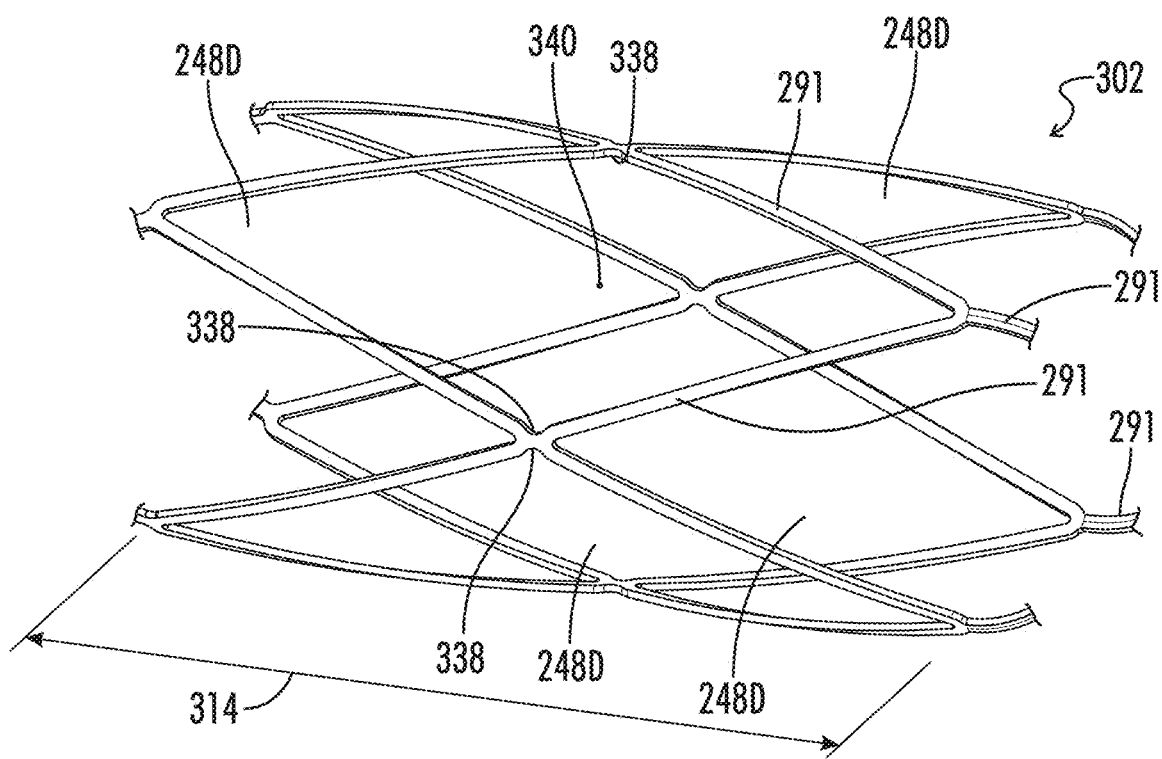
FIG. 36D illustrates an enlarged front perspective view of the area labeled 36D in FIG. 36C.
Figure 36E:
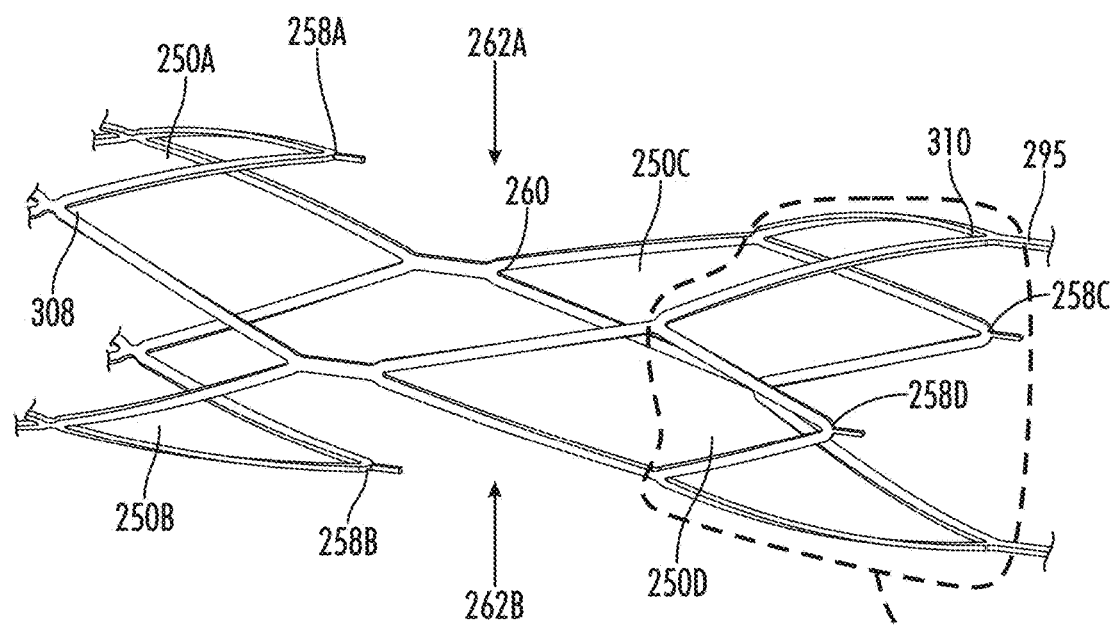
FIG. 36E illustrates an enlarged front perspective view of the area labeled 36E in FIG. 36C.
Figure 36F:
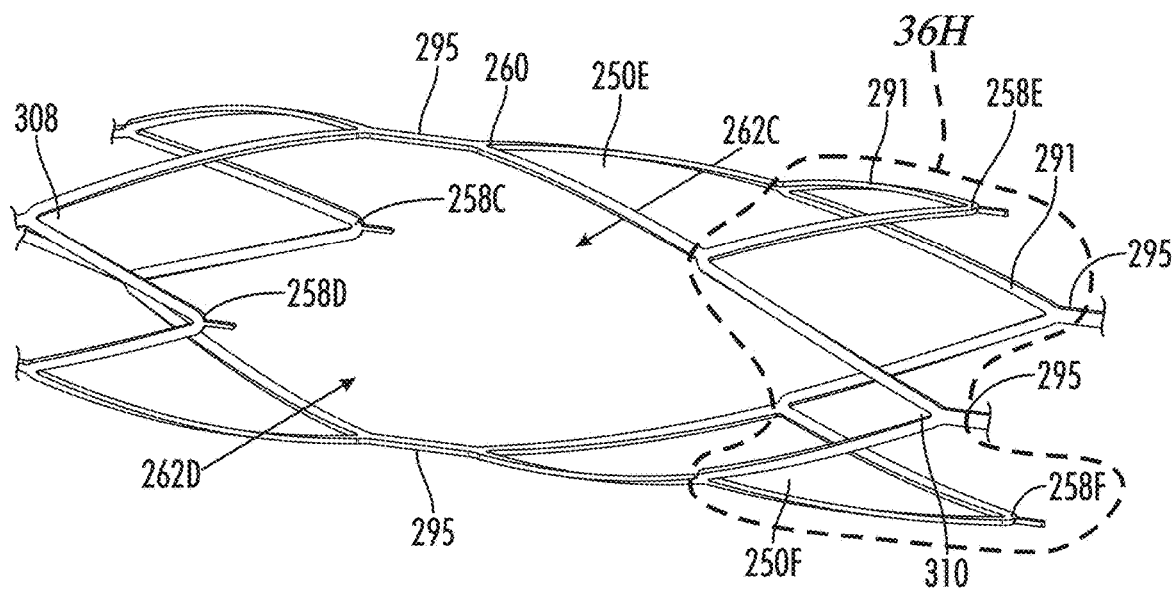
FIG. 36F illustrates an enlarged front perspective view of the area labeled 36F in FIG. 36C.
Figure 36G:
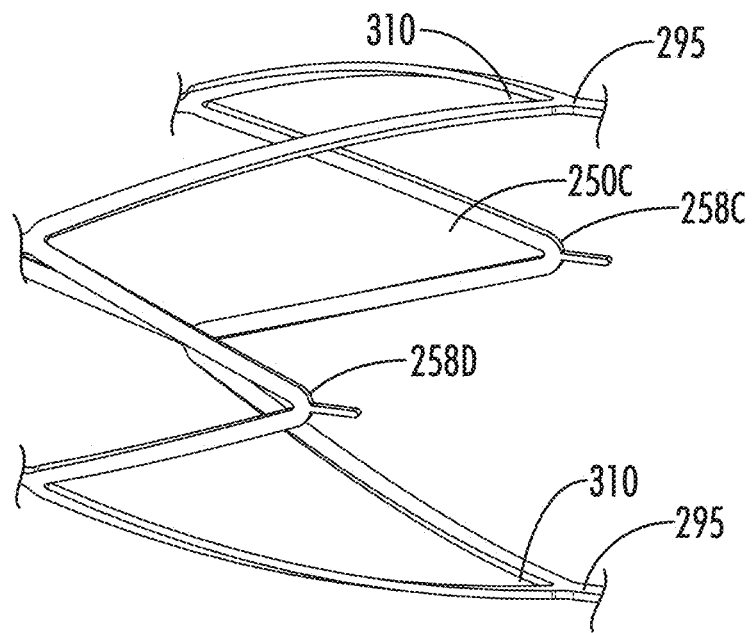
FIG. 36G illustrates an enlarged front perspective view of the area labeled 36G in FIG. 36E.
Figure 36H:
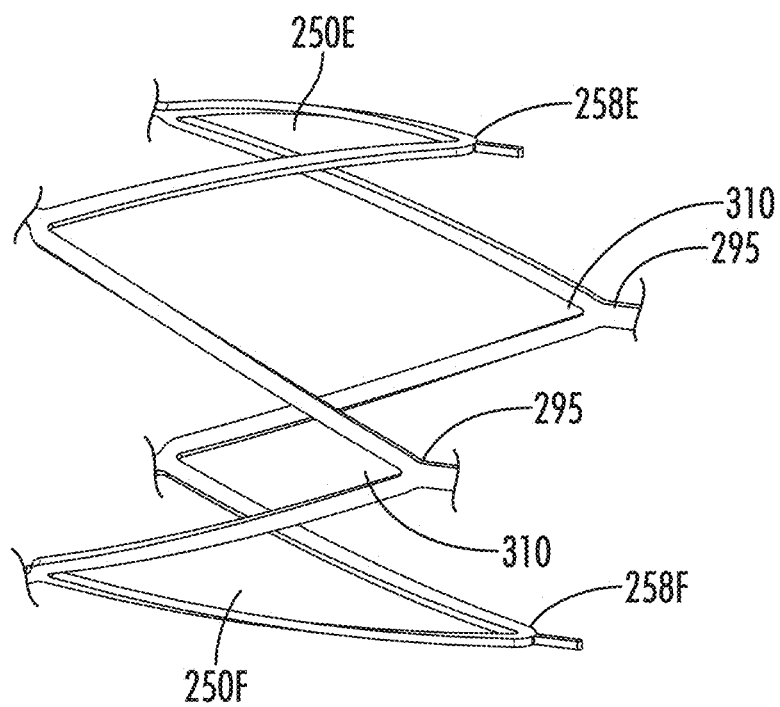
FIG. 36H illustrates an enlarged front perspective view of the area labeled 36H in FIG. 36F.
Figure 36K:
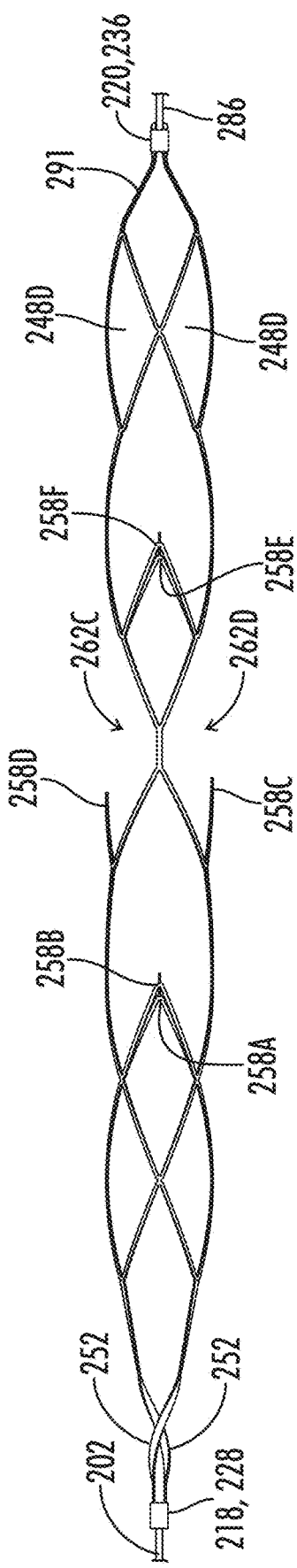
FIG. 36K illustrates a bottom plan view of the distal body of FIG. 36A.
Figure 36L:
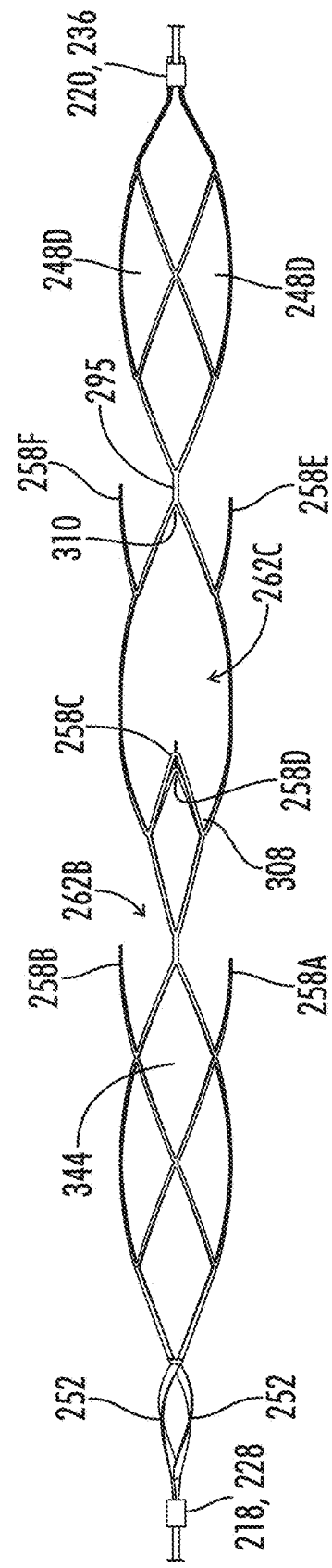
FIG. 36L illustrates a rear elevation view of the distal body of FIG. 36A.
Figure 36M:
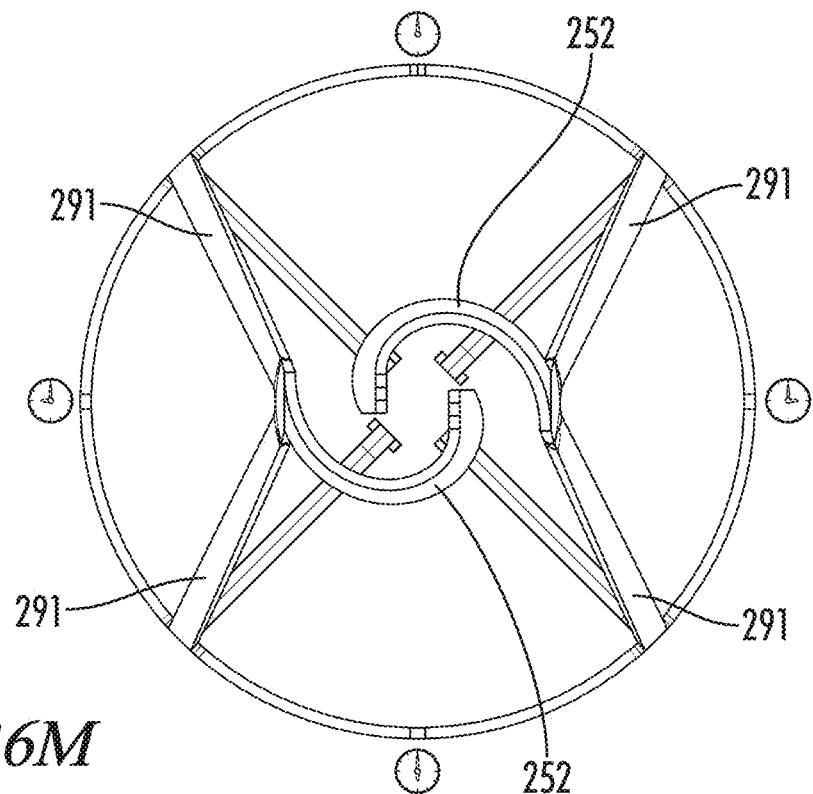
FIG. 36M illustrates a proximal elevation view of the distal body of FIG. 36A.
Figure 36N:
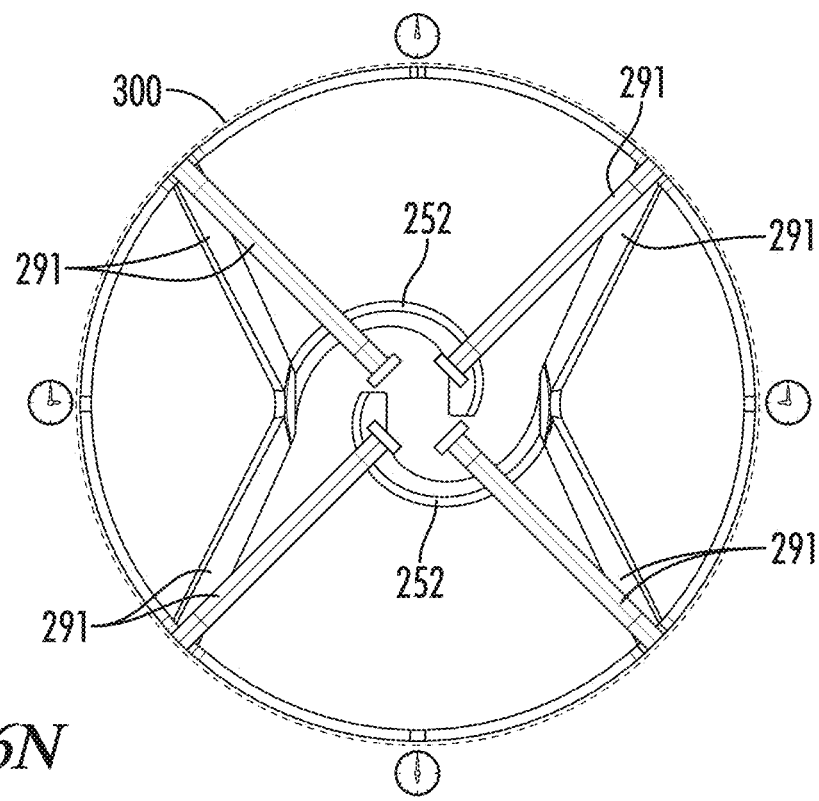
FIG. 36N illustrates a distal elevation view of the distal body of FIG. 36A.

Optionally, as with prior embodiments, in the embodiment of FIG. 36, as best seen in FIGS. 36J and 36L, in the relaxed state, the basket 246 further comprises an additional pair of cells 344 located about the same distance from the proximal junction 228 as the cells 250A, 250B comprising the proximal-most pair of free distal crowns 258A, 258B and located at the 9 and 3 o'clock positions, each cell of the additional pair of cells 344 having a proximal crown attached to a memory metal strip (either a basket strip 291 or a proximal strip 252) and a distal crown attached to another cell of the basket 246 (i.e., a non-free floating distal crown). Again, about the same distance means the same distance from the proximal hub 228+/−5 mm. (In preferred embodiments, the additional pair of cells 344 are located the same distance+/−3 mm, more preferably the same distance+/−0.5 mm, from the proximal hub 228). As best seen in FIGS. 36J and 36L, the additional pair of cells 344 may adjoin the enlarged cells 262A, 262B formed by the proximal-most free distal crowns 258A, 258B. Optionally, from at least the distal crowns of the additional pair of cells 344 to the proximal ends of the enlarged cells 262E, 262F formed by the succeeding free distal crowns 258E, 258F, the basket 246 has no cells other than the enlarged cells 262A-262F, the cells 250A-250F comprising the free distal crowns 258A-258F and the additional pair of cells 344.

As with prior embodiments, FIGS. 36-37 illustrate that in the relaxed state, the basket 246 may comprise a series of struts/bridge memory metal strips 295 having a proximal end 334 attached to a distal crown of a cell and a distal end 336 attached to a proximal crown of a distally-located cell. The proximal-most pair of bridge memory metal strips 295 may be located at the 3 and 9 o'clock positions, the next proximal-most pair of bridge memory metal strips 295 may be located at the 12 and 6 o'clock positions, the succeeding proximal-most pair of bridge memory metal strips may be located at the 3 and 9 o'clock positions, so that the bridge memory strips 295, like the free distal crowns 258A-258J, alternate along the distal body length 226. Each of the pair of bridge memory metal strips 295 may form part of at least one enlarged cell 262A-262J. Optionally, the bridge memory metal strips 295 are the sole distally-extending basket strips 291 attached to the respective proximal crowns and the sole proximally-extending basket strips 291 attached to the respective distal crowns.

As with prior embodiments, FIGS. 36-37 illustrate that in the relaxed state, each of the pair of bridge memory metal strips 295 may form part of two enlarged cells 262A-262J. As with prior embodiments, FIGS. 36 and 37 illustrate that in the relaxed state the bridge memory metal strips 295 may be substantially parallel to the distal body length 226.

As with prior embodiments, FIGS. 36-37 illustrate that in the relaxed state, the plurality of distal cells 248D may be comprised of four distal cells 248D located about the same distance from the proximal junction 228, each cell having a center 340, and the centers 340 of the cells 248D may be spaced at approximately 90 degree intervals about the distal body perimeter 300, and each of said four distal cells 248D may adjoin two of the other of said distal four cells 248D, as best seen in FIGS. 36C and 36D. Again, about the same distance means the same distance from the proximal hub 228+/−5 mm. (In preferred embodiments, the four distal cells 248D are located the same distance+/−3 mm, more preferably the same distance+/−0.5 mm, from the proximal hub 228). Optionally, in the relaxed state, as best seen in FIGS. 36C and 36D, each of the four distal cells 248D comprises two lateral crowns 338 pointing generally in a direction perpendicular to the distal body length 226 and each lateral crown 338 of one of said four cells 248D adjoins a lateral crown 338 of an adjacent of said four cells 248D.

As with prior embodiments, FIGS. 36-37 illustrate that the distal body 216 preferably has no more than four cells at any location along the distal body length 226.

As with prior embodiments, FIGS. 36-37 illustrate that each of the enlarged cells 260A-260J may be approximately the same size.

As with prior embodiments, FIGS. 36-37 illustrate that in the relaxed state, the basket interior 346 may be substantially hollow.

As with prior embodiments, FIGS. 36-37 illustrate that in the relaxed state, the enlarged cells 262A, 262B formed by the proximal-most free distal crowns 258A, 258B may be adjoining, the enlarged cells 262C, 262D formed by the next proximal-most free distal crowns 258C, 258D may be adjoining and the enlarged cells 262E, 262F formed by the succeeding free distal crowns 258E, 258F may be adjoining. Optionally, as shown in the illustrations of FIGS. 36-37, in the relaxed state each of the enlarged cells 262C, 262D formed by the next proximal-most free distal crowns 258C, 258D adjoins an enlarged cell 262A, 262B formed by a proximal-most free distal crown 258A, 258B and an enlarged cell 262E, 262F formed by a succeeding free distal crown 258E, 258F.

As with prior embodiments, FIGS. 36-37 illustrate that in the relaxed state, for at least some enlarged cells 262A-262J (preferably for each enlarged cell, as shown in the illustrations), the free distal crown 258A-258J may be aligned with the distal crown 307 located at the distal end 310 of the enlarged cell 262A-262J.

As with prior embodiments, FIGS. 36-37 illustrate that in the relaxed state, the distal cells 248D may be substantially the same size and attached to the distal junction 236 by a basket strip 291 having a proximal end attached to a distal crown of a distal cell 248D and a distal end attached to the distal junction 236.

As with prior embodiments, FIGS. 36-37 illustrate that in the relaxed state, the cells 250A-250J comprising the free distal crowns 258A-258J may be substantially the same size.

As with prior embodiments, the system of FIGS. 36-37 may be used in a method of removing a blood clot from a blood vessel of an animal the method comprising the steps of: a) providing the system; b) positioning the system in the blood vessel; c) allowing the height 224 and width 225 of the distal body 216 to increase; d) moving the blood clot into the basket interior 346; and e) moving the distal body 216 proximally out of the blood vessel.

As with prior embodiments, in FIGS. 36-37, not all parts are labeled in every drawing for clarity.

The embodiments of FIGS. 36-37 may include any feature described or shown with the prior embodiments. For example, as illustrated in FIGS. 36-37, the proximal junction 228 and distal junction 236 may be located approximately in the center of the distal body width 225 and distal body height 224 in the relaxed state. Additionally, as illustrated in FIGS. 36-37, each pair of enlarged cells 262A/262B; 262C/262D; 262E/262F; 262G/262H; 262I/262J may be substantially aligned such that each pair of enlarged cells 262A/262B; 262C/262D; 262E/262F; 262G/262H; 262I/262J and the substantially hollow interior 346 create a void extending from one side of the basket 246 through the substantially hollow interior 346 to the opposite side of the basket 246. In addition, FIGS. 36-37 illustrate the previously mentioned and shown twisting proximal strips 252. For example, the proximal end 254 of a first proximal strip 252 may be located at least about 65 degrees relative to the distal end 256 of the first proximal strip 252, the proximal end 254 of a second proximal strip 252 may be located least about 65 degrees relative to the distal end 256 of the second proximal strip 252, and the first and second proximal strips 252 may intersect adjacent and distal to the proximal junction 228 and the intersection may be located approximately in the center of the first height 224 and first width 225 in the relaxed state. In addition, FIG. 37 illustrate that the distal body 216 may have a void located between the proximal junction 228 and the cells 250A, 250B comprising the proximal-most free distal crowns 258A, 258B. In addition, FIGS. 36-37 illustrate that the basket 246 has a non-uniform outward radial force from the proximal strips 252 to the basket distal end 302. As with prior embodiments, in the embodiments of FIGS. 36-37, the free distal crowns of each pair of free distal crowns 258A/258B; 258C/258D; 258E/258F; 258G/258H; 258I/258J may be configured to contact each other when an exterior, external compressive force is exerted on the free distal crowns 258A-258J when the distal body 216 is in the relaxed state. As with prior embodiments, in the embodiments of FIGS. 36-37, the proximal junction 228 and distal junction 236 may be in the form of tubes. In addition, the distal body 216 may include the three-dimensional openings 293 mentioned previously. As with the prior embodiments, in the embodiments of FIGS. 36 and 37, some or all of the free distal crowns 258A-258J, as well as proximal and distal junctions 228 and 236, may include x-ray markers, as previously described.

The Embodiments of FIGS. 38-45

FIGS. 38-45 illustrate yet another clot retrieval system 400 in accordance with the present invention. The system 400 of FIGS. 38-45 is particularly adapted to capture a clot 402 (e.g., a pulmonary embolism) in a pulmonary blood vessel 404, which taper in diameter less gradually than cranial vessels. The system 400 includes a suction catheter (also known as an aspiration catheter) 436 that passes into the interior 422 of a cage 408 and includes one or more suction openings 444 so that when the suction catheter 436 is connected to a suction source (such as a syringe or pump that is proximal to the suction opening 444 and located adjacent to the suction catheter proximal end 440) that applies a proximal suction force (i.e., a suctional force in the proximal direction such as shown in FIGS. 44A and 44B where the arrows generally point in the proximal direction), the surgeon is able to use the suction opening 444 to draw a clot 402 into the interior 422 of the cage 408. Nonetheless, the system of FIGS. 38-45 may be used to retrieve other objects in other lumens of the body.

Figure 38:
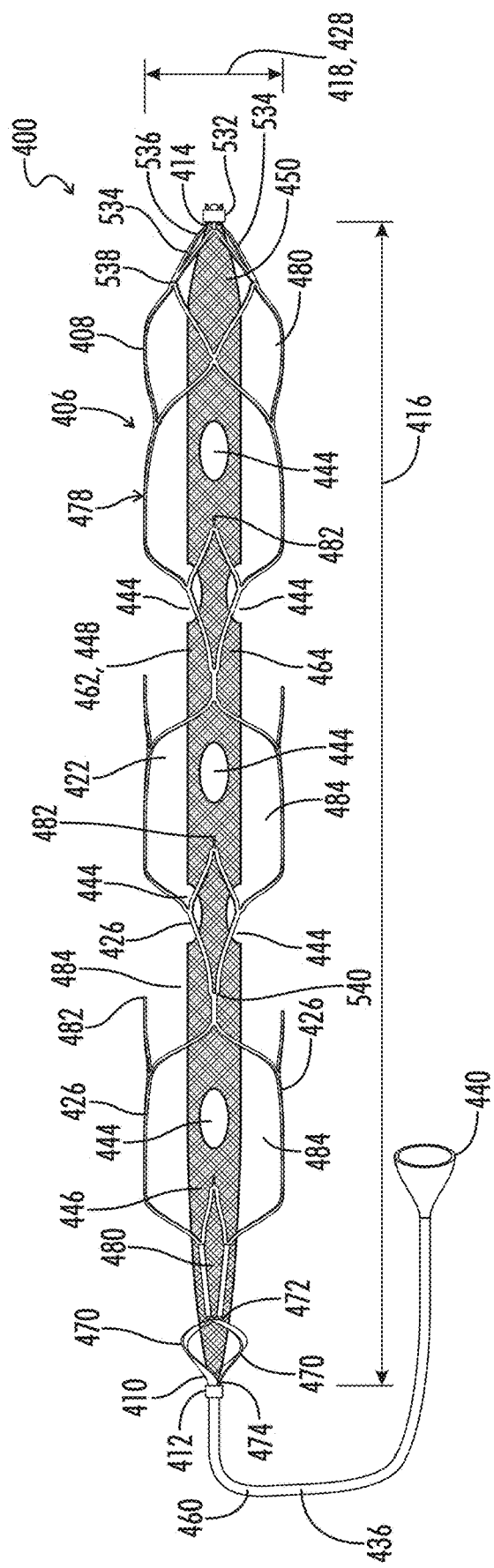
FIG. 38 illustrates a side elevation view of a distal body and an expandable suction catheter of another embodiment of the present invention.
Figure 39:
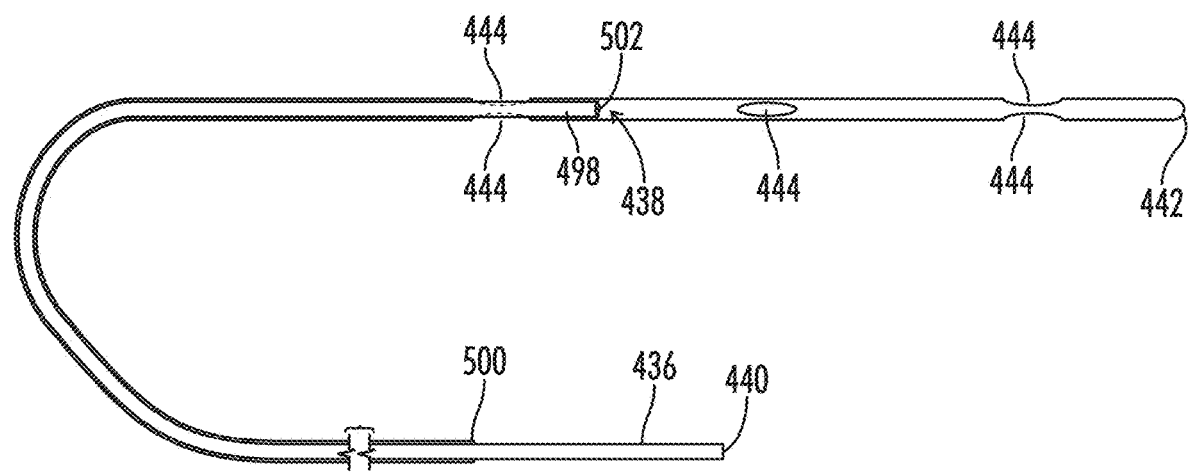
FIG. 39 illustrates a side elevation view of a non-expandable suction catheter of another embodiment of the present invention with the suction catheter made transparent to show the inner blocking catheter.
Figure 40:
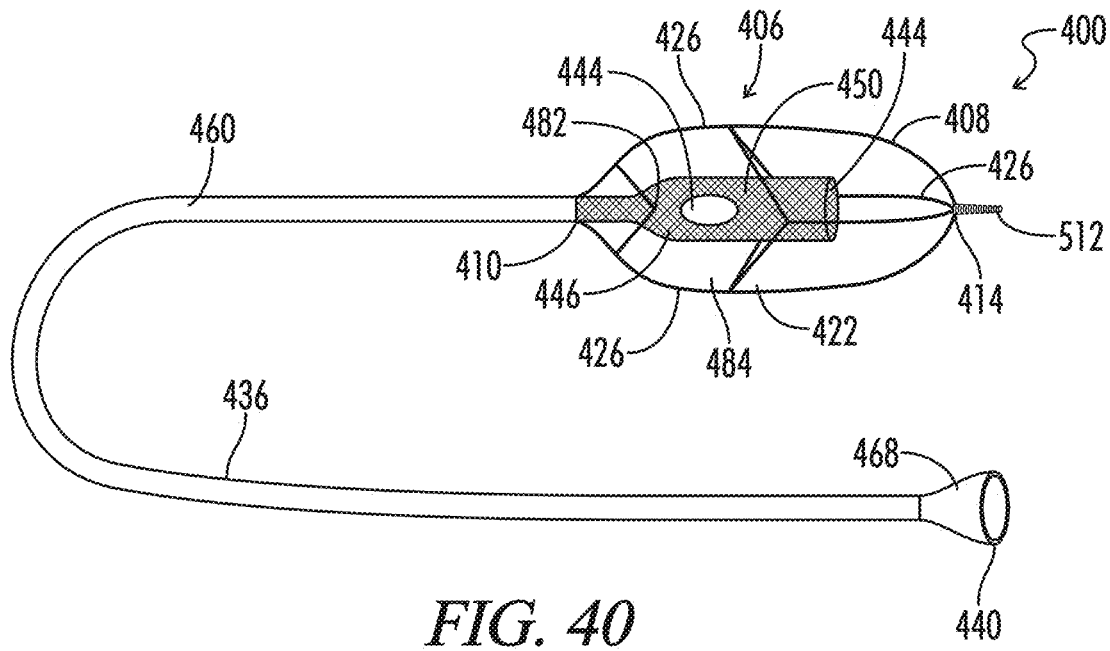
FIG. 40 illustrates a side perspective view of a distal body and an expandable suction catheter of another embodiment of the present invention.
Figure 41:
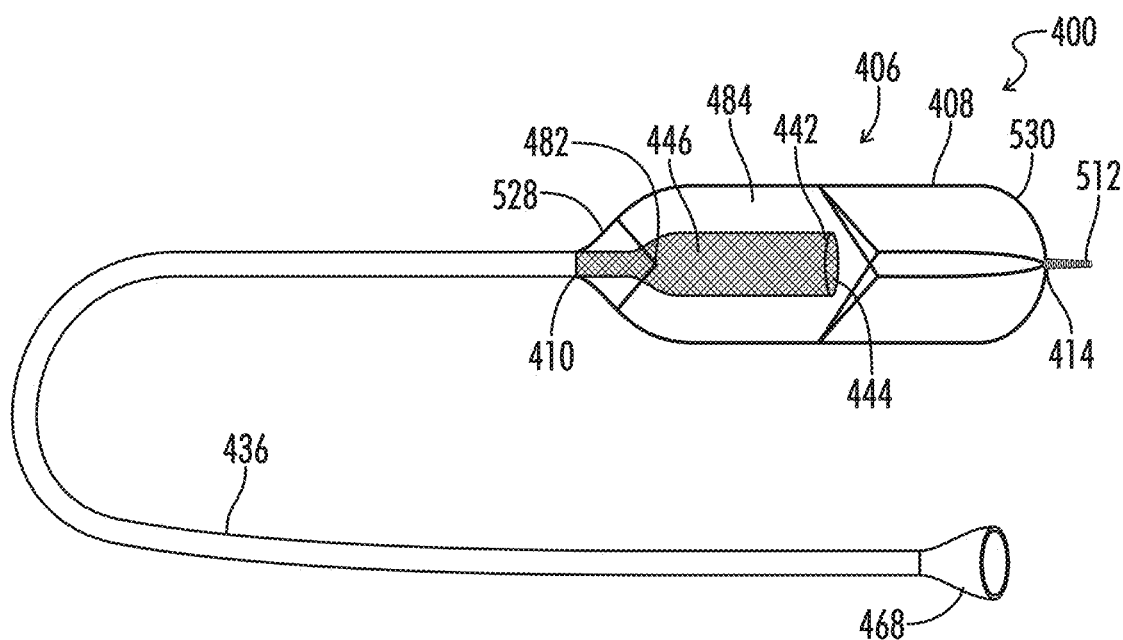
FIG. 41 illustrates a side perspective view of a distal body and an expandable suction catheter of another embodiment of the present invention.

In the embodiment of FIGS. 38-45, the system 400 may include a distal body, which may be in the form of a cage 408 comprising a cage proximal end 410 that may comprise a proximal junction 412, a cage distal end 414, a cage length 416 extending from the cage proximal end 410 to the cage distal end 414, a cage height 418 perpendicular to the cage length 416, a cage width perpendicular to the cage length 416 and cage height 418, a cage interior 422 and a cage perimeter (not specifically labeled but denoted in other embodiments with numeral 300) comprised of a plurality of memory metal strips 426. Optionally, the cage 408 has a relaxed state wherein the cage has a first height 428 and a first width, and a collapsed state wherein the cage has a second height 432 and a second width, the second height 432 of the cage 408 less than the first height 428 of the cage 408, the second width of the cage 408 less than the first width of the cage 408. In some embodiments, as shown in FIGS. 38 and 40-41, the cage 408 is in the form of a stent retriever with a plurality of cells 480 and is similar in design to the distal bodies of the previous embodiments. In other embodiments, as shown in FIGS. 42-45 the cage 408 may take a slightly different design.

The system 400 may also include a suction catheter 436 comprising a generally hollow interior 438, a proximal end 440 located proximal to the cage proximal end 410, and a distal end 442. The suction catheter 436 may be attached to the cage proximal end 410 and may pass into the cage interior 422. In some embodiments, the suction catheter 436 may be attached to the cage distal end 414, as shown in FIG. 38. In other embodiments, the suction catheter distal end 442 may be proximal to the cage distal end 414, as shown in FIGS. 40-45. Within the cage interior 422, the suction catheter 436 may comprise at least one suction opening 444, which preferably is located between the cage proximal end 410 and the cage distal end 414, and leads to the suction catheter generally hollow interior 438. The at least one suction opening 444 allows the suction catheter 436 to apply suction force to draw the clot 402 from outside the cage interior 422 into the cage interior 422, as shown in FIGS. 44A-44B, for example.

In some embodiments, the suction catheter 436 is not expandable, as shown in FIG. 39. In other embodiments, the suction catheter 436 may comprise an expandable distal tip 446, which may be comprised of a memory metal. In such embodiments, the suction catheter 436 may comprise an expandable distal tip 446 that is located adjacent to the suction catheter distal end 442 and is comprised of a memory metal framework 448 and, optionally, a film/coating 450 attached to the memory metal framework 448. Optionally, the expandable distal tip 446 has a relaxed state wherein the expandable distal tip 446 has a first height 452 and a first width, and a collapsed state wherein the expandable distal tip 446 has a second height 456 and a second width, the second height 456 of the expandable distal tip 446 is less than the first height 452 of the expandable distal tip 446, as best seen comparing FIG. 45E with FIG. 45D. Optionally, the first height 452 of the expandable distal tip 446 is less than the first height 428 of the cage 408 and the first width of the expandable distal tip 446 is less than the first width of the cage 408, as shown in FIG. 38, and FIGS. 40-45.

Figure 39A:
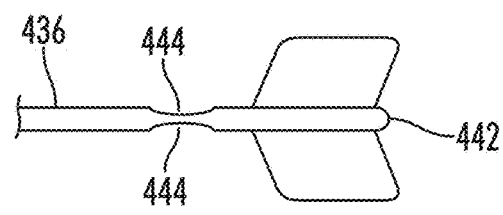
FIG. 39A illustrates a side elevation of a distal end of a suction catheter of another embodiment of the present invention.
Figure 39B:
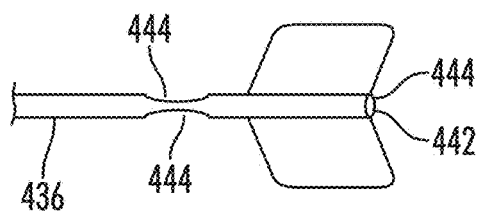
FIG. 39B illustrates a side elevation of a distal end of a suction catheter of another embodiment of the present invention.

Optionally, in the relaxed state, the expandable distal tip 446 of the suction catheter 436 is tapered in shape (e.g., in the shape of a funnel) in the relaxed state, as shown in FIGS. 40-45. Optionally, the distal end 442 of the suction catheter 436 forms the maximum height and width of the expandable distal tip 446 in the relaxed state, as shown in FIGS. 40-45. Optionally, the distal end 442 of the suction catheter 436 is flared inward, as shown in FIGS. 39A and 39B.

Optionally, the cage 408 comprises a width and a height 418 of between about 15 and about 35 millimeters in the relaxed state. Optionally, the suction catheter 436 comprises a non-expandable proximal segment 460, which is comprised of a different material than the expandable distal tip 446, is located immediately proximal to the expandable distal tip 446, and the non-expandable proximal segment 460 is configured to maintain substantially the same height and same width when the expandable distal tip 446 moves between the collapsed state and the relaxed state. Optionally, the expandable distal tip 446 comprises a maximum width in the relaxed state that is between about 2 and about 6 times greater than the width of the proximal segment. Optionally, the expandable distal tip 446 comprises a maximum height in the relaxed state that is between about 2 and about 6 times greater than the height of the proximal segment.

Optionally, the memory metal framework 448 is comprised of woven/braided linear memory metal strands 462, as shown in FIGS. 38 and 40-45. Examples of woven/braided linear memory metal strands with films/coatings are known in the art. For example, the Anaconda suction catheters with such frameworks and films/coatings are sold by Anaconda Biomed SL (Barcelona, Spain) and described in European Patent Application EP3634768, where it is described that the woven/braided linear strands may be dipped into a polymeric coating or sprayed onto the strands and that the film/coating may create a watertight compartment. Woven/braided linear strands also are described in Applicant's own U.S. Pat. Nos. 10,321,925 and 10,226,268, for example. The contents of the aforementioned European Patent Application and U.S. patents are incorporated herein by reference. Optionally, each woven linear strand may rotate about the distal portion perimeter relative to the cage length/longitudinal axis a plurality of times in a helical fashion. Optionally, the suction catheter expandable distal tip 446 may be flexible and invertible, as with the Anaconda suction catheter.

Optionally, the at least one suction opening 444 is located at the distal end 442 of the suction catheter 436, as shown in FIGS. 39B, 40-45. Alternatively, the distal end 442 of the suction catheter 436 may be closed, as shown in FIGS. 38-39 and 39A.

Optionally, as shown in FIGS. 38-40, the at least one suction opening 444 is located in the film 450 proximal to the suction catheter distal end 442. It will be understood that the term "at least one suction opening" allows for the suction catheter 436 to have multiple suction openings 444 within the cage interior 422, as shown in FIGS. 38, 39B and 40 for example. Optionally, if one side of the suction catheter 436 (e.g., the top) includes a suction opening 444, preferably the opposite side (e.g., the bottom) also includes an aligned suction opening 444, as best seen in FIGS. 38 and 39B. This can also be inferred in FIG. 40, for example, because there is no film 450 on the side opposite of the suction opening 444 visible. In other words, optionally, the centers of the suction openings 444 are aligned longitudinally and located between 150 and 180 degrees apart.

Figure 42:
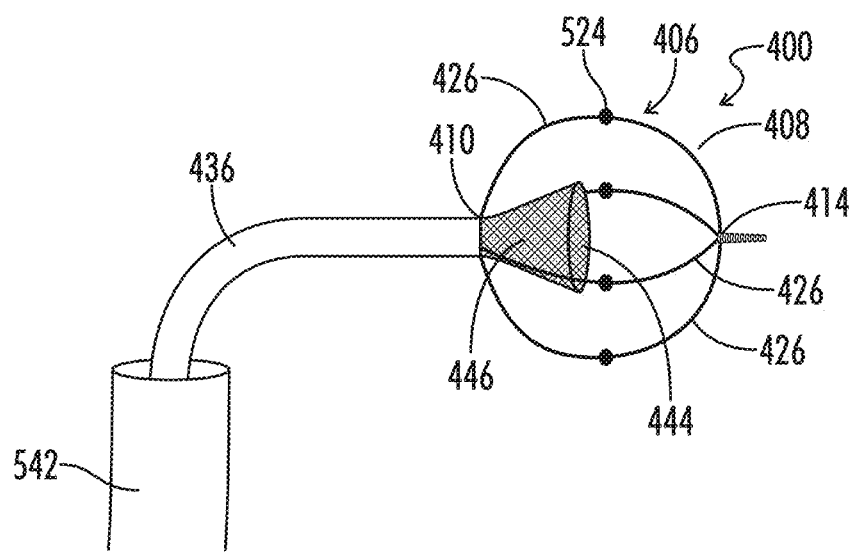
FIG. 42 illustrates a side perspective view of a distal body, a portion of an expandable suction catheter and a guide catheter of another embodiment of the present invention.
Figure 43:
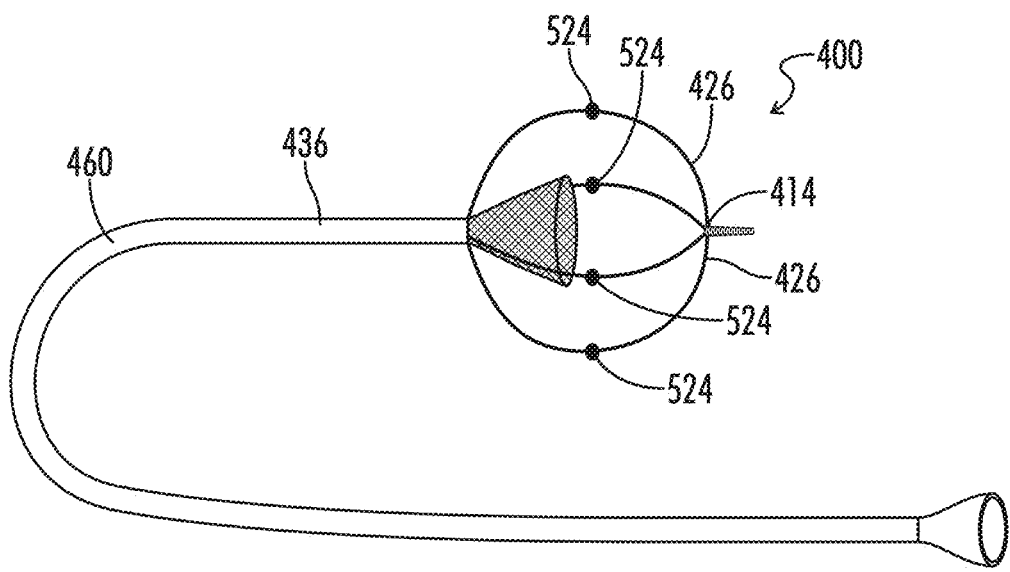
FIG. 43 illustrates a side perspective view of the distal body and suction catheter of FIG. 42.
Figure 44A:
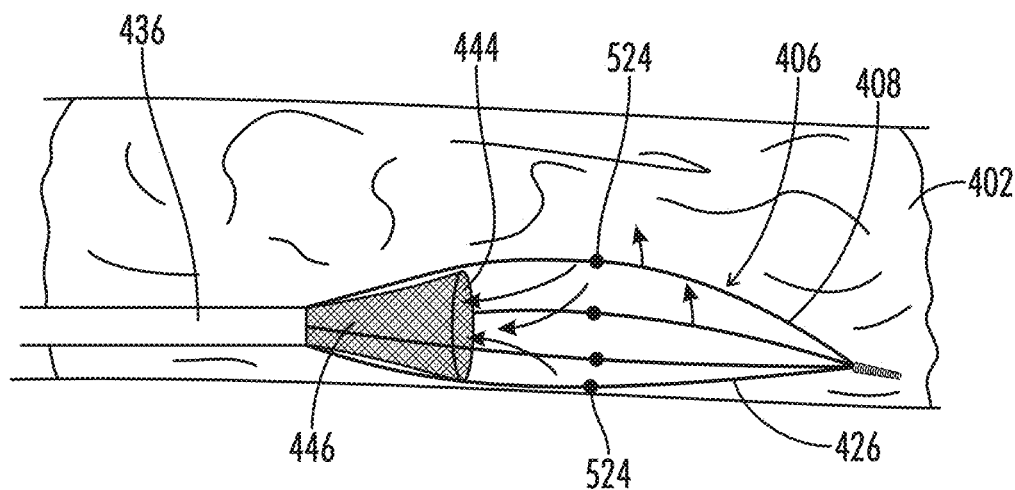
FIG. 44A illustrates a side perspective view of the distal body and suction catheter of FIG. 42 being used to capture a clot in a pulmonary blood vessel; as shown by the arrows pointing upward, the distal body is expanding into the clot; as shown by the arrows pointing toward the suction catheter, a suction force is drawing the clot towards the suction catheter.
Figure 44B:
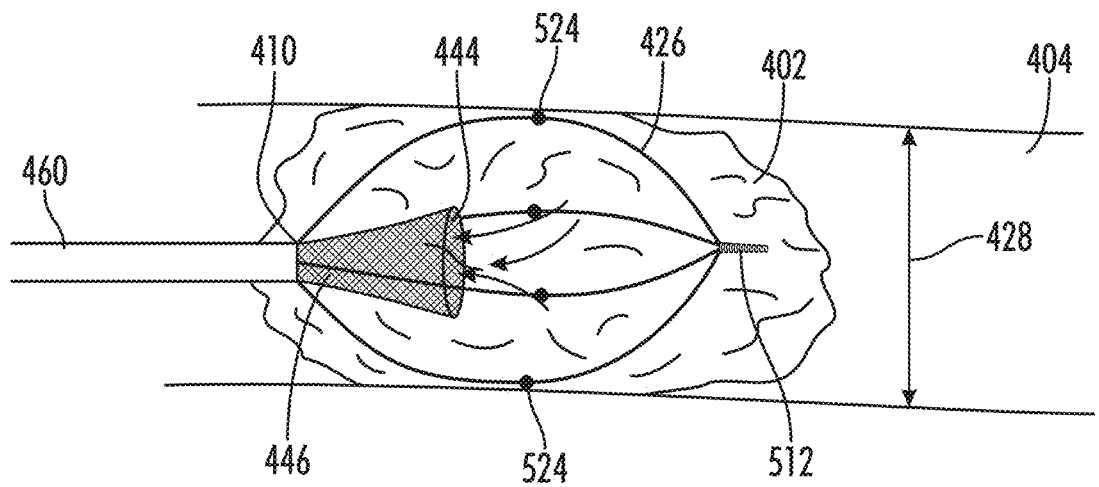
FIG. 44B illustrates a side perspective view of the distal body and suction catheter of FIG. 44A being used to capture the clot; as compared to FIG. 44A, in FIG. 44B, the distal body is fully expanded (i.e., fully in its relaxed state).

Optionally, the cages 408 comprise a plurality of x-ray markers 524 located between the suction catheter distal end 442 and the cage distal end 414, as best seen in FIGS. 42-44. Optionally, as best seen in FIGS. 42-44, the x-ray markers 524 are aligned longitudinally (i.e., each of the x-ray markers 524 is located approximately the same distance from the cage proximal end 410). Without being bound by any particular theory, the plurality of x-ray markers 524 may inform the operator/surgeon the location of the cage 408 relative to the clot 402 so that the operator deploys the cage 408 in the correct location in the vessel 404.

Optionally the proximal end 440 of the suction catheter 436 is connected to a syringe or a pump, not shown but well-known in the art.

Optionally, the cage 408 is not free floating on the suction catheter 436 but instead the attachment of the suction catheter 436 to the cage 408 is configured to allow an operator to pull the cage 408 proximally by pulling the suction catheter 436 proximally and to push the cage 408 distally by pushing the suction catheter 436 distally. In other words, the surgeon may be able to move the cage 408 proximally and distally by moving the suction catheter 436 proximally and distally.

Optionally, the proximal 440 end of the suction catheter 436 comprises a tapered (e.g., funnel shaped) hub/coupler 468 configured to connect the proximal end 440 to a suction source, as shown in FIGS. 38, 40, 41 and 43 for example.

Optionally, in the relaxed state, the cage 408 comprises a tapered proximal region 528 in which the cage height 418 and the cage width decrease as the memory metal strips 426 located at the proximal end of the cage 408 approach the cage proximal end 410, as shown in FIGS. 38, and 40-45.

Optionally, in the relaxed state, the cage 408 comprises a tapered distal region 530 in which the cage height 418 and the cage width decrease as the memory metal strips 426 located at the distal end of the cage 408 approach the cage distal end 414, as shown in FIGS. 38, and 40-45.

Optionally, the cage 408 further comprises a cage proximal junction 412 located at the cage proximal end 410 and a plurality of proximal strips 470, each proximal strip 470 having a distal end 472 and a proximal end 474, the proximal ends of the proximal strips 470 converging at the cage proximal junction 412, and further wherein the suction catheter 436 passes through the cage proximal junction 412, as shown in FIG. 38.

Optionally, as shown in FIGS. 38 and 40-45, the cage 408 further comprises a cage distal junction 532 located at the cage distal end 414 and a plurality of distal strips 534, each distal strip 534 having a distal end 536 and a proximal end 538, the distal ends 536 of the distal strips 534 converging at the cage distal junction 532.

Optionally, the suction catheter 436 is attached to the cage distal junction 532, as shown in FIG. 38. Optionally, the suction catheter distal end 442 may extend distally beyond the cage distal end 414. Optionally, the suction catheter 436 is not attached to the cage distal end 414.

Optionally, the suction catheter 436 has a length of from about 60 centimeters to about 150 centimeters.

Optionally, the suction catheter 436 comprises a plurality of suction openings 444 and at least some of the plurality suction openings 444 are located proximal to the suction catheter distal end 442, as shown in FIGS. 38-40.

Optionally, as shown in FIGS. 38 and 40-41 the cage 408 is comprised of a framework 478 comprising a plurality of cells 480 formed by the plurality of memory metal strips 426. Optionally, in the relaxed state, at least one of the suction openings 444 located proximal to the suction catheter distal end 442 is aligned with a cell 480 to allow the operator to use the suction opening 444 to move the clot through the cell 480 and into the cage interior 422. For example, as shown in FIGS. 38 and 40-41, the heightwise center of the suction opening 422 may be aligned with the heightwise center of the cell 480 so that the suction force is centered in the cell 480. Optionally, in the relaxed state, as shown in FIGS. 38 and 40-41, the framework 478 comprises at least one pair of distal crowns 482 not attached to another cell 480 and pointing generally in the distal direction, the distal crowns 482 in the at least one pair of distal crowns 482 located approximately the same distance from the cage proximal end 410 and located between 150 degrees and 180 degrees relative to each other. Optionally, each distal crown in the at least one pair of distal crowns 482 forms part of a different enlarged cell 484, each enlarged cell 484 having a center. Optionally, the centers of the enlarged cells 484 of the at least one pair of distal crowns 482 are between 150 degrees and 180 degrees relative to each other. Optionally, the enlarged cells 484 are configured to allow a clot 402 to pass therethrough and into the cage interior 422. Optionally, one or more of the suction openings 444 located proximal to the suction catheter distal end 442 is aligned with an enlarged cell 484. Optionally, as shown in FIG. 38, as with prior embodiments, the enlarged cells 484 are sequentially offset (e.g., the proximal-most pair of enlarged cells 484 are offset 60-90 degrees from the next proximal most pair of enlarged cells 484, which are offset 60-90 degrees from the succeeding proximal-most pair of enlarged cells and so forth) and the suction openings 444 are likewise sequentially offset.

Optionally, as shown in FIG. 38, the cage 408 further comprises a cage proximal junction 412 located at the cage proximal end 410 and a plurality of proximal strips 470, each proximal strip 470 having a distal end 472 attached to a proximal crown 540 of a cell of the cage 408 and a proximal end 474, the proximal ends of the proximal strips 470 converging at the cage proximal junction 412.

Figure 45A:
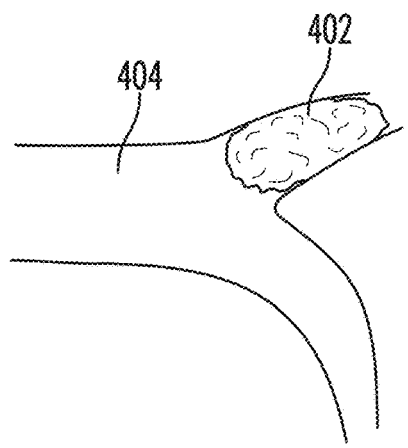
FIGS. 45A-45G illustrate side perspective views of the stepwise sequence of the distal body and suction catheter of FIG. 42 being used to capture a clot in a pulmonary blood vessel, with the guide catheter also shown in FIGS. 45B-45G, and with FIG. 45G showing how the clot is being moved proximally out of the blood vessel.
Figure 45B:
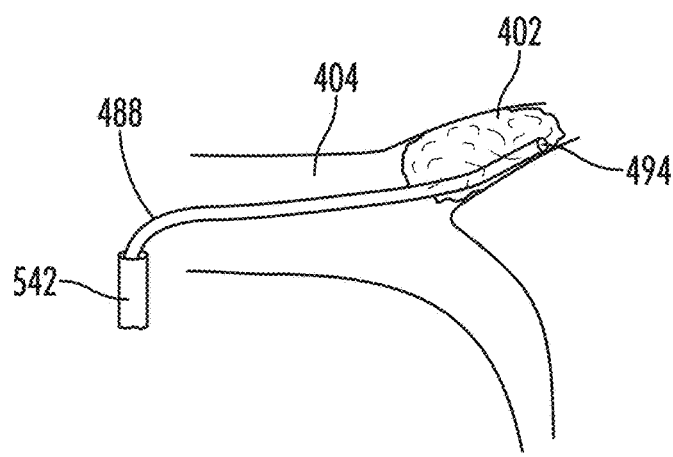
Figure 45C:
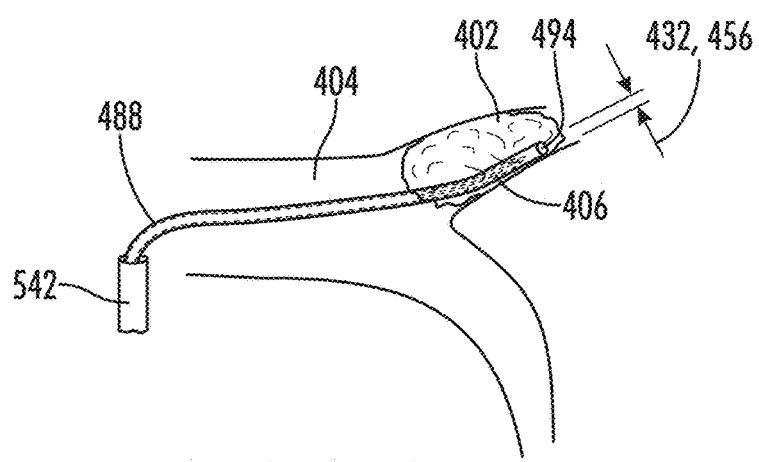
Figure 45D:
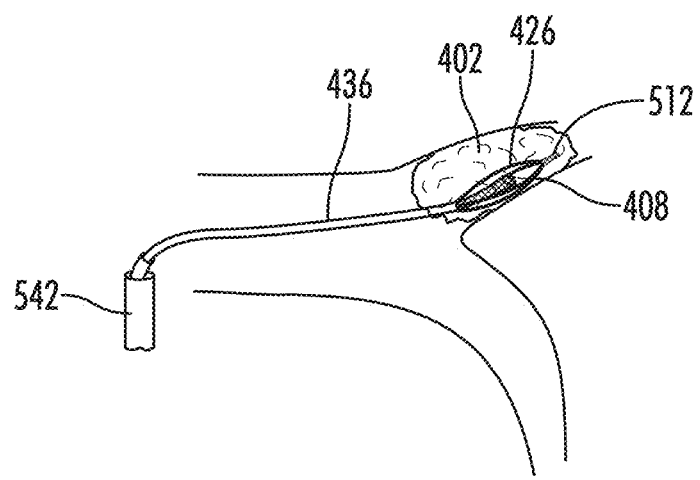
Figure 45E:
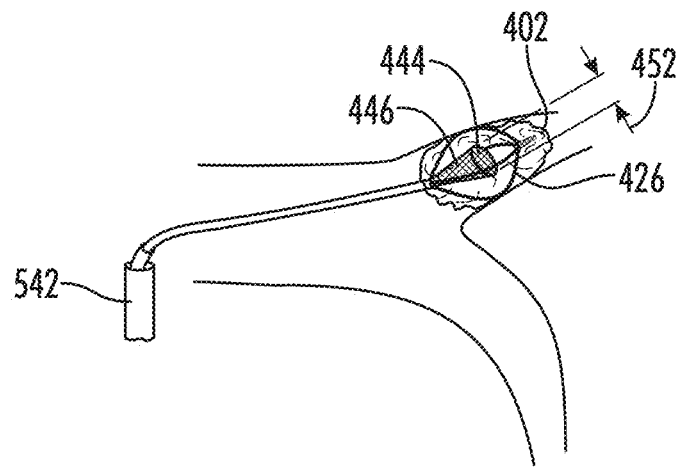
Figure 45F:
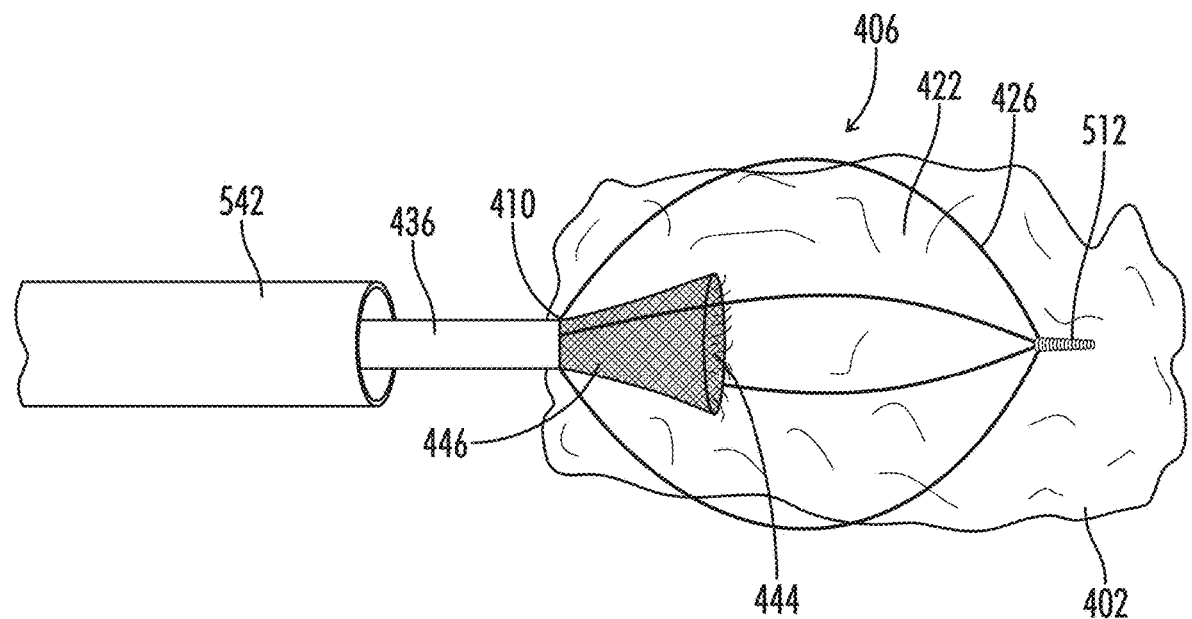

Optionally, as shown in FIG. 45E, the system 400 further comprises a delivery catheter 488 having an interior, a proximal end (not shown) leading to the interior and a distal end 494 leading to the interior, the delivery catheter 488 comprised of a biocompatible material and configured to envelop the cage 408 and the suction catheter 436 prior to deployment from the delivery catheter 488. The system 400 may also include a guide catheter 542 as shown in FIGS. 42 and 45E and 45F.

Optionally, as shown in FIG. 39, the system 400 may include an inner blocking catheter 498 located in the suction catheter generally hollow interior 438 and movable proximally and distally in the suction catheter generally hollow interior 438, the inner blocking catheter 498 comprising an open proximal end 500, an open distal end 502 and a generally hollow interior. Without being bound by any particular theory, the inner blocking catheter 498 may be used to block a suction hole(s) 444 in the suction catheter 436, as shown in FIG. 39 where the proximal suction holes 444 are blocked. Optionally, the inner blocking catheter 498 and the suction catheter 436 each comprise an outer diameter and an inner diameter and further wherein the outer diameter of the inner blocking catheter 498 is between about 85% to about 99.9% of the size of the inner diameter of the suction catheter 436.

Optionally, the heightwise/widthwise center of the suction catheter 436 is located approximately in the heightwise/widthwise center of the cage 408 in the relaxed state, as shown in FIGS. 38 and 40-45.

Optionally, though not shown, the cage 408 may further include scaffolding memory metal strips 426 extending from the cage perimeter inwardly to the suction catheter 436 to help maintain the suction catheter 436 in the center of the cage 408.

Optionally, in the relaxed state, the cage 408 has a minimum height 418 and width at the cage proximal end 410, as shown in FIGS. 40-45.

Optionally, except for the suction catheter 436, the cage interior 422 is hollow.

Optionally, as shown in FIG. 38, the cage proximal end 410 is in the form of a tube.

Optionally, as shown in FIG. 38 and FIGS. 40-41, in the relaxed state, the cage 408 is comprised of a plurality of cells 480 but does not have any free proximal crowns 540 pointing generally in the proximal direction but does have free distal crowns 482 pointing generally in the distal direction.

Optionally, the system further includes a lead wire 512 extending distally from the cage distal end 414.

Generally, as exemplified in FIGS. 44A and 44B, and 45A-45G, the system 400 may be used in a method of removing a blood clot 402 from an animal the method comprising the steps of:

a) providing a delivery catheter 488 having an interior, a proximal end and a distal end 494, the delivery catheter 488 enveloping the cage 408 (see FIG. 45C);

b) deploying the cage 408 from the delivery catheter distal end 494 so the cage 408 moves from the collapsed state to the relaxed state (see FIGS. 45D and 45E);

c) applying suction to the suction catheter 436 to move the blood clot 402 into the cage interior 422 (see FIG. 45F as well as FIGS. 44A and 44B); and d) moving the cage 408 and blood clot 402 proximally out of the animal (see FIG. 45G) e.g., by pulling proximally on the suction catheter 436.

Optionally, the method further comprises connecting a syringe or a pump (not shown but known in the art) to the suction catheter proximal end 440 and using the syringe or the pump to apply suction to the suction catheter 436.

Optionally, as shown in FIG. 39, the method further comprises, before step c), providing an inner blocking catheter 498 located in the suction catheter generally hollow interior 438 and moving the inner blocking catheter 498 proximally or distally in the suction catheter generally hollow interior 438 to cover a suction opening 444 in the suction catheter 436.

Optionally, steps b) and c) occur in a lung of the animal.

Figure 22:
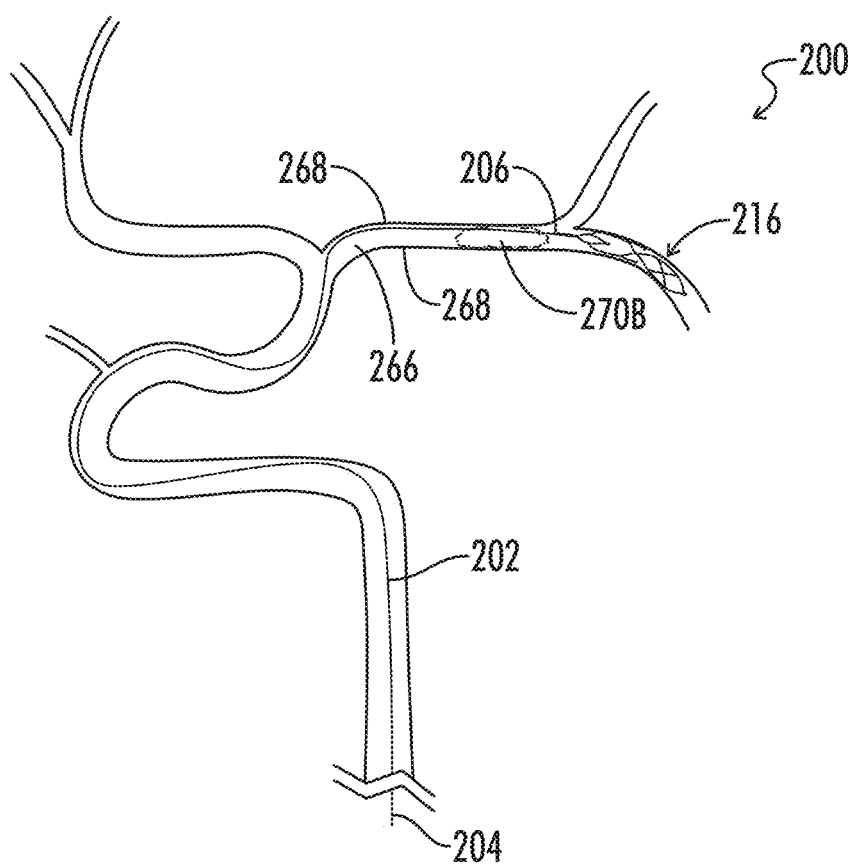
FIG. 22 shows a perspective view of the distal body of FIG. 21, after deployment of the distal body and retraction of the delivery catheter, in a blood vessel.
Figure 23:
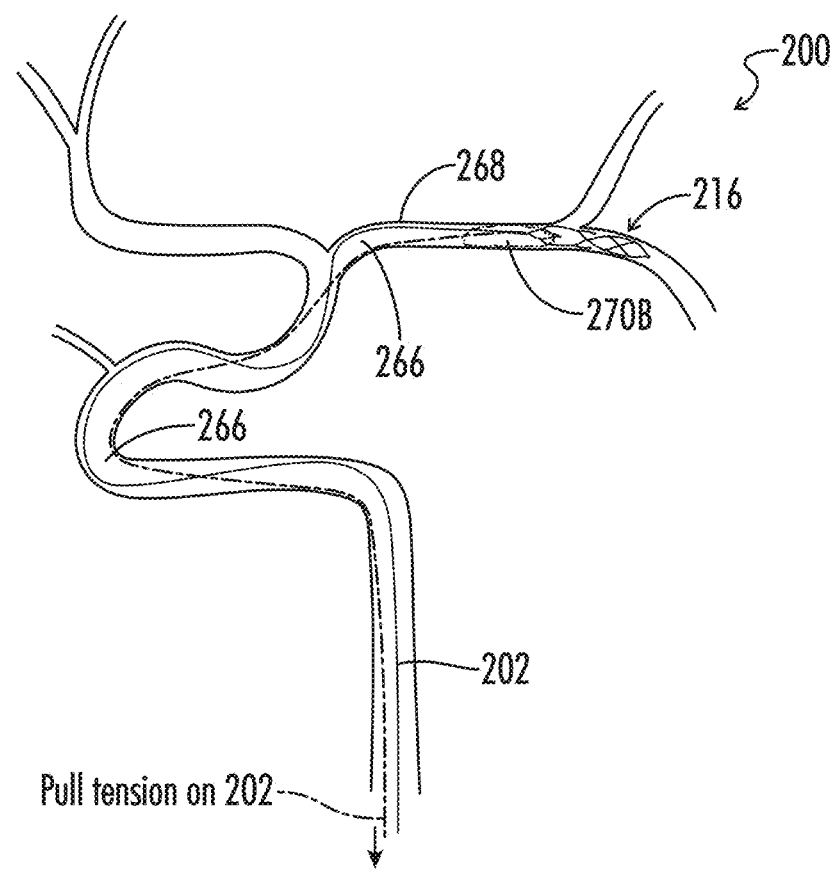
FIG. 23 shows a perspective view of the distal body of FIG. 21; as compared to FIG. 22, the distal body has been moved proximally and tension has been exerted on the pull wire.
Figure 24:
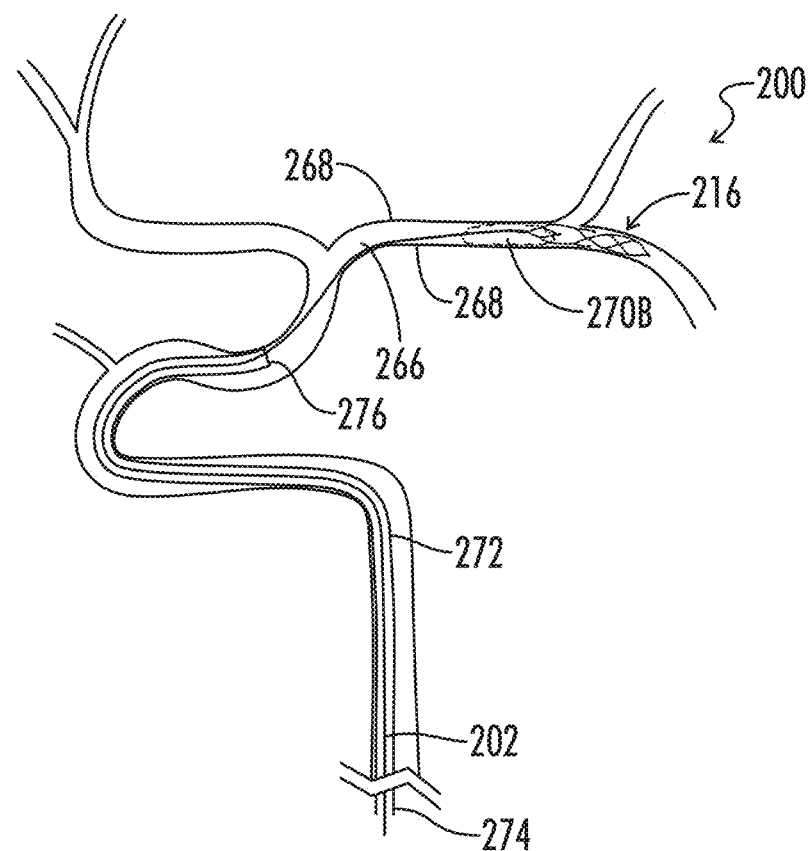
FIG. 24 shows a perspective view of a suction catheter that is being delivered over the pull wire of the system of FIG. 21.
Figure 25:
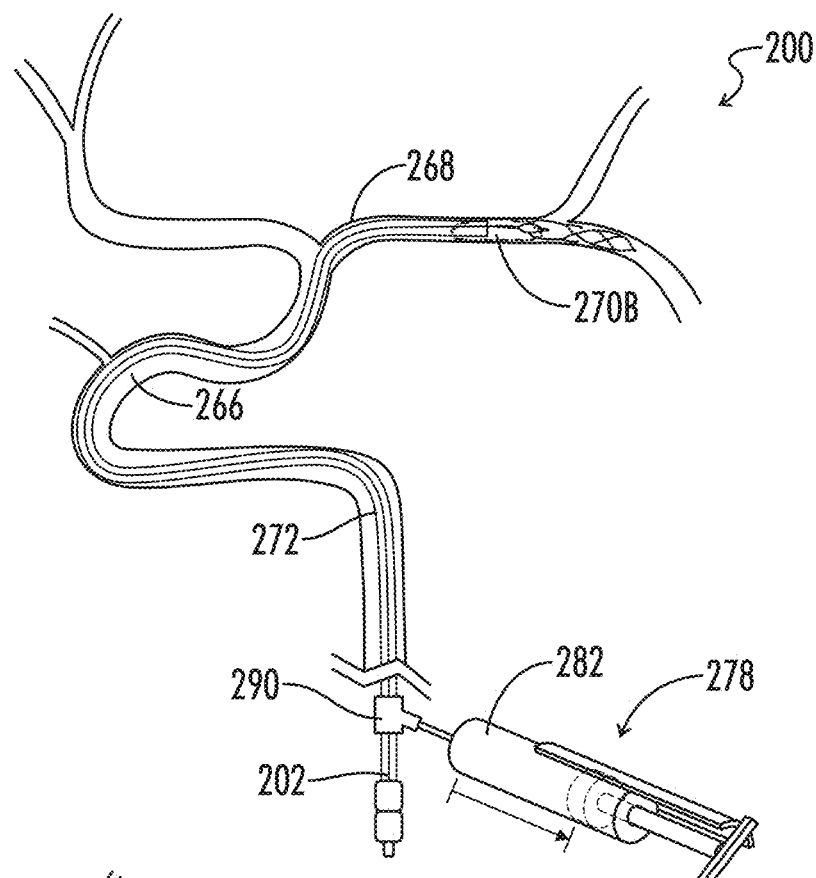
FIG. 25 shows a perspective view of the distal end of the suction catheter of FIG. 24 being pushed into a clot; a syringe is sucking the clot to the suction catheter because the user has pulled back on the lever of the syringe.
Figure 26:
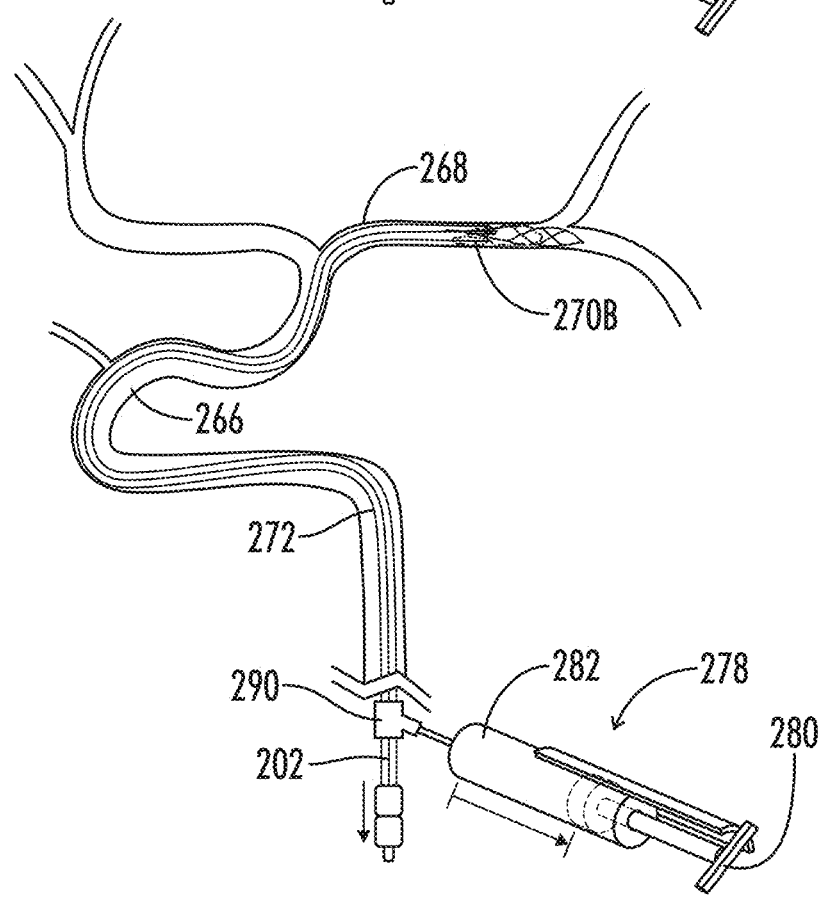
FIG. 26 shows a perspective view of the distal end of the suction catheter of FIG. 24 being pushed into a clot.
Figure 27:
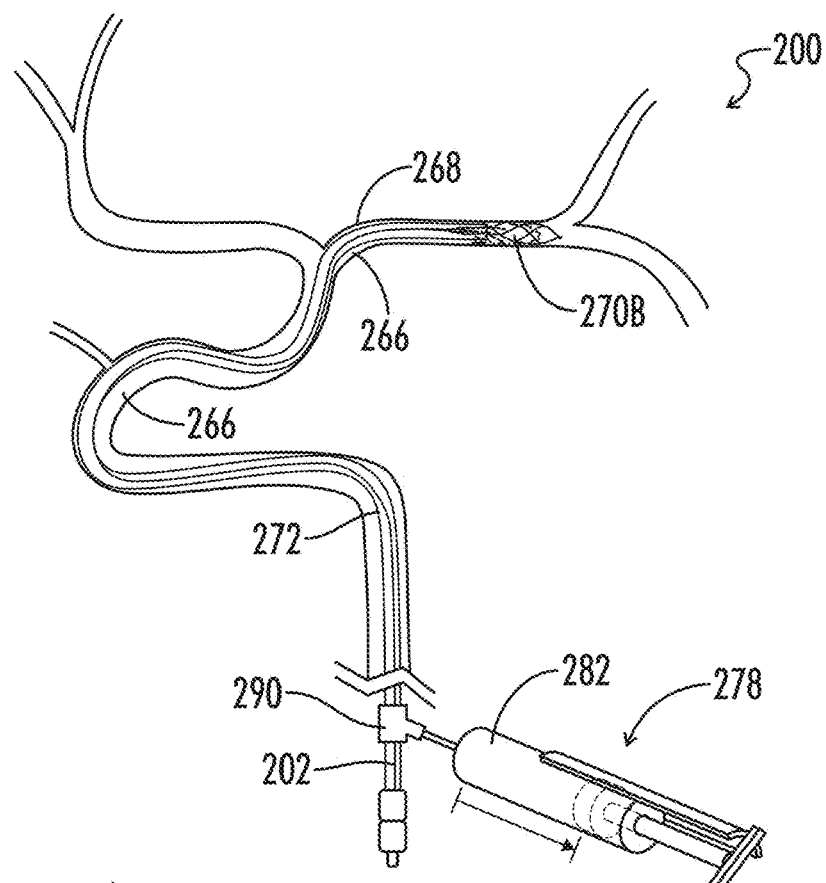
FIG. 27 shows a perspective view of the system of FIG. 24.
Figure 28:
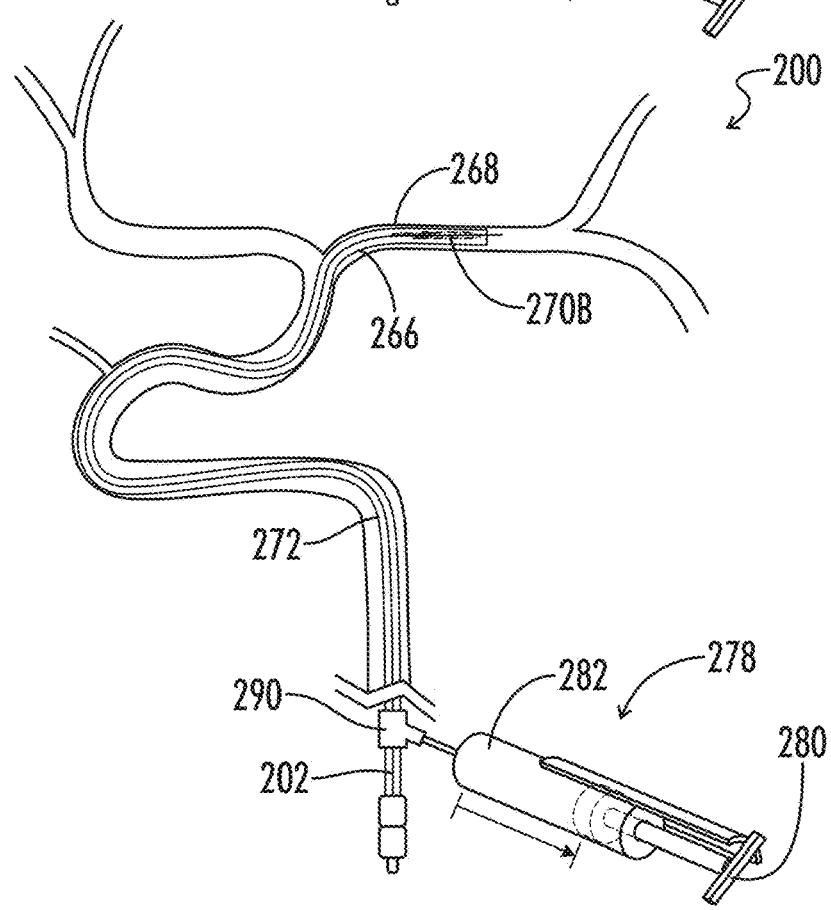
FIG. 28 shows a perspective view of the system of FIG. 24.
Figure 29:
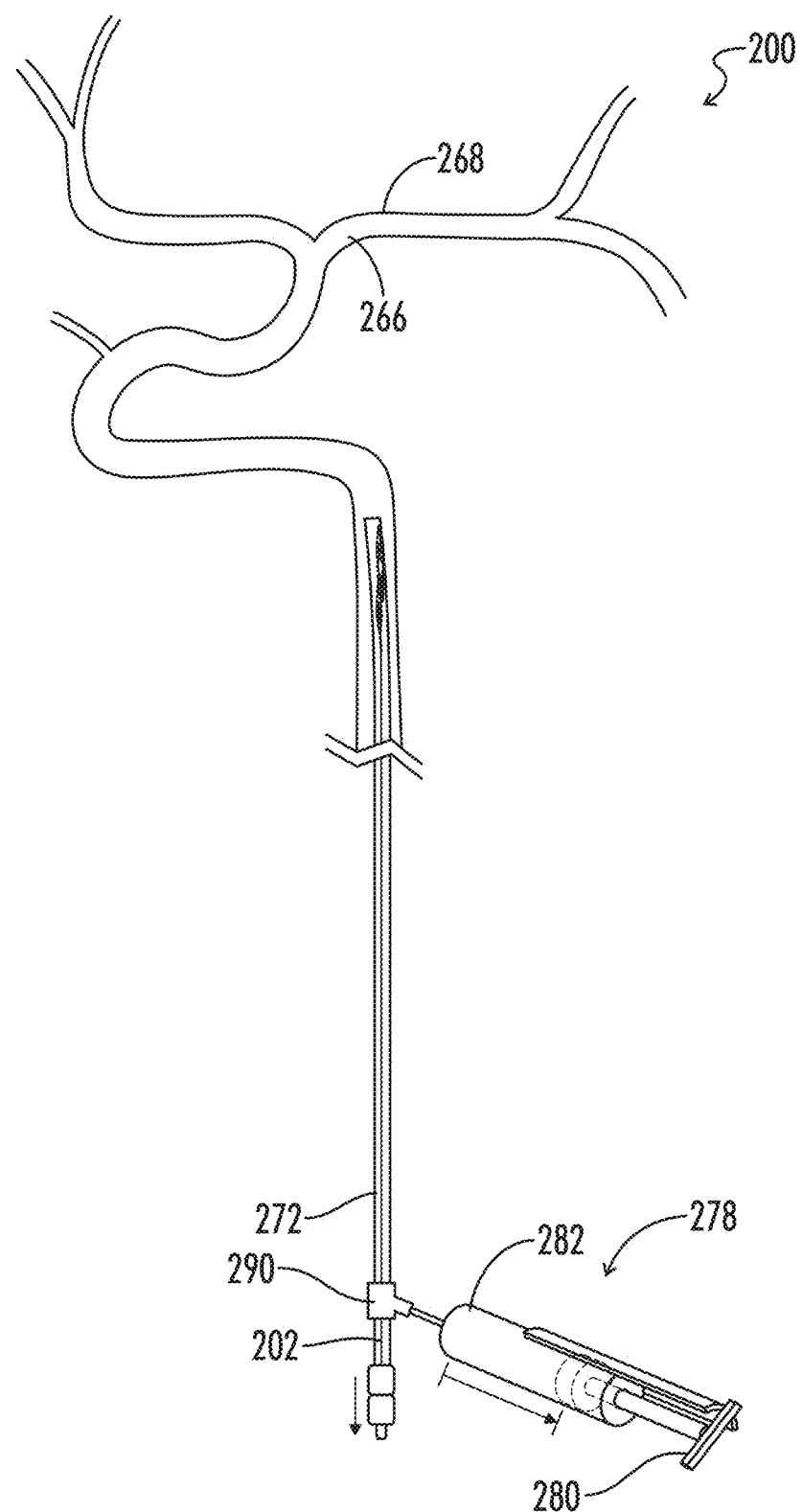
FIG. 29 shows a perspective view of the system of FIG. 24; the system, and captured clot, is being removed proximally from the vessel.
Figure 45G:
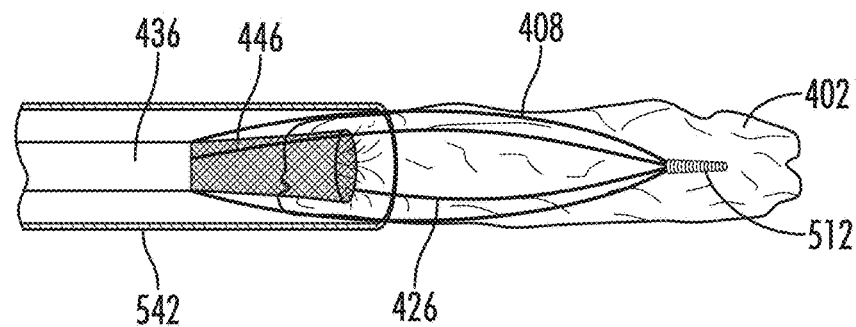

Without being bound by any particular theory, FIGS. 44A and 44B and 45D and 45E show how the cage 408 may gradually move from the collapsed state to the relaxed state. Unlike the prior embodiment as best seen in FIG. 22, where the distal body is deployed distally to the clot 402, in the embodiment of FIGS. 38-45, the cage 408 may be deployed at the site of the clot 402, as best seen in FIGS. 44A-44B and 45D and 45E where the cage proximal end 410 is distal to the clot's 402 proximal end and the cage distal end 414 is proximal to the clot's 402 distal end. In addition to a delivery catheter 488, a guide catheter 542 having a larger diameter than the delivery catheter 488 may also be used, as shown in FIGS. 45C-45G. After clot 402 capture, the suction catheter 436, the cage 408 and the clot 402 may be moved (fully or partially) into the guide catheter 542, as shown in FIG. 45G.

PARTS LIST

| | |
|---|---|
| Clot retrieval system | 400 |
| Clot | 402 |
| Pulmonary blood vessel | 404 |
| Distal body | 406 |
| Cage | 408 |
| Cage proximal end | 410 |
| Cage proximal junction | 412 |
| Cage distal end | 414 |
| Cage length | 416 |
| Cage height | 418 |
| Cage width | Not shown |
| Cage interior | 422 |
| Plurality of memory metal strips | 426 |
| Cage first height | 428 |
| Cage first width | Not shown |
| Cage second height | 432 |
| Cage second width | Not shown |
| Suction catheter | 436 |
| Suction catheter hollow interior | 438 |
| Suction catheter proximal end | 440 |
| Suction catheter distal end | 442 |
| Suction opening | 444 |
| Suction catheter expandable distal tip | 446 |
| Memory metal framework | 448 |
| Film | 450 |
| Expandable distal tip first height | 452 |
| Expandable distal tip second height | 456 |
| Suction catheter non-expandable proximal segment | 460 |
| Woven linear memory metal strands | 462 |
| Plurality of braided mesh openings | 464 |
| Tapered hub | 468 |
| Plurality of proximal strips | 470 |
| Proximal strip distal end | 472 |
| Proximal strip proximal end | 474 |
| Cell | 480 |
| Free distal crowns | 482 |
| Enlarged cell | 484 |
| Delivery catheter | 488 |
| Delivery catheter distal end | 494 |
| Inner blocking catheter | 498 |
| Inner blocking catheter open proximal end | 500 |
| Inner blocking catheter open distal end | 502 |
| Lead wire | 512 |
| Plurality of x-ray markers | 524 |
| Tapered proximal region | 528 |
| Tapered distal region | 530 |
| Cage distal junction | 532 |
| Cage distal strips | 534 |
| Cage distal strips distal ends | 536 |
| Cage distal strips proximal ends | 538 |
| Proximal crown | 540 |
| Guide catheter | 542 |

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention, as defined and limited solely by the following claims. In particular, although the system has been exemplified for use in retrieving blood clots, the system may be used to retrieve other objects from animal lumens. In addition, the steps of any method described herein may be performed in any suitable order and steps may be performed simultaneously if needed.

Terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A system for removing a blood clot from a human blood vessel, the system comprising:
   a distal body comprising a cage comprising a cage proximal end comprising a plurality of proximal memory metal strips, a cage distal end, a cage length extending from the cage proximal end to the cage distal end, a cage height perpendicular to the cage length, a cage width perpendicular to the cage length and cage height, a cage interior and a cage perimeter comprised of the plurality of proximal memory metal strips, wherein the cage has a relaxed state wherein the cage has a first height and a first width, and a collapsed state wherein the cage has a second height and a second width, the second height of the cage less than the first height of the cage, the second width of the cage less than the first width of the cage; and
   a suction catheter comprising a generally hollow interior, a proximal end located proximal to the cage proximal end, and a distal end located proximal to the cage distal end, the suction catheter attached to the cage and passing into the cage interior, the suction catheter, within the cage interior, comprising at least one suction opening located between the cage proximal end and the cage distal end, the at least one suction opening leading to the generally hollow interior,
   wherein the plurality of proximal memory metal strips are fixedly attached to a segment of the suction catheter between the suction catheter proximal end and the suction catheter distal end and
   wherein the cage comprises a cage distal junction forming the cage distal end and further wherein the cage perimeter further comprises a plurality of distal memory metal strips that converge at the cage distal junction.

2. The system of claim 1 wherein the at least one suction opening is configured to allow an operator to draw a clot from outside the cage interior into the cage interior when a proximal suction force is applied to the suction catheter.

3. The system of claim 2 wherein the at least one suction catheter is connected to a syringe or a pump and the syringe or pump is configured to apply a proximal suction force to the suction opening to draw a clot into the cage interior.

4. The system of claim 1 wherein the proximal end of the suction catheter comprises a tapered hub configured to connect the proximal end of the suction catheter to a suction source.

5. The system of claim 1 wherein the cage is comprised of a framework comprising a plurality of cells.

6. The system of claim 5, wherein, in the relaxed state, at least one of the at least one suction openings is aligned with a cell.

7. The system of claim 6 wherein, in the relaxed state, at least one of the at least one suction openings is aligned with a lengthwise center of a cell.

8. The system of claim 5 wherein, in the relaxed state, the framework comprises at least one pair of distal crowns not attached to another cell and pointing generally in the distal direction, the distal crowns in the at least one pair of distal crowns located approximately the same distance from the cage proximal end and located between 150 degrees and 180 degrees relative to each other, wherein each distal crown in the at least one pair of distal crowns forms part of a different enlarged cell, each enlarged cell having a center,
   wherein the centers of the enlarged cells of the at least one pair of distal crowns are between 150 degrees and 180 degrees relative to each other, and further wherein the enlarged cells are configured to allow a clot to pass therethrough and into the cage interior, and further wherein a suction opening is aligned with an enlarged cell.

9. The system of claim 8 wherein a heightwise center of at least one of the at least one suction openings is aligned with a heightwise center of an enlarged cell.

10. The system of claim 1 wherein, within the cage interior, the suction catheter comprises at least one pair of suction openings proximal to the suction catheter distal end, each of the at least one pair of suction openings having a center, the centers of the at least one pair of suction openings located between 150 degrees and 180 degrees relative to each other.

11. The system of claim 10 wherein the suction catheter distal end is open.

12. The system of claim 1 wherein the suction catheter comprises an expandable distal tip located adjacent to the suction catheter distal end and comprised of a memory metal framework and a film attached to the memory metal framework, wherein the expandable distal tip has a relaxed state wherein the expandable distal tip has a first height and a first width, and a collapsed state wherein the expandable distal tip has a second height and a second width, the second height of the expandable distal tip less than the first height of the expandable distal tip and the second width of the expandable distal tip less than the first width of the expandable distal tip, and further wherein the first height of the expandable distal tip is less than the first height of the cage and the first width of the expandable distal tip is less than the first width of the cage.

13. The system of claim 12 wherein, in the relaxed state, the expandable distal tip of the suction catheter is tapered in shape, and further wherein the distal end of the suction catheter forms the maximum height and width of the expandable distal tip in the relaxed state.

14. The system of claim 12 wherein the cage comprises a maximum width and a maximum height of between about 15 millimeters and about 35 millimeters in the relaxed state, wherein the suction catheter comprises a non-expandable proximal segment immediately proximal to the expandable distal tip, the non-expandable proximal segment configured to maintain substantially the same height and same width when the expandable distal tip moves between the collapsed state and the relaxed state, and further wherein the expandable distal tip comprises a maximum width in the relaxed state that is between about 2 and about 6 times greater than the width of the proximal segment and further wherein the expandable tip comprises a maximum height in the relaxed state that is between about 2 and about 6 times greater than the height of the proximal segment.

15. The system of claim 12 wherein the memory metal framework is comprised of woven linear memory metal strands forming a plurality of braided mesh openings and further wherein the film covers the mesh openings.

16. The system of claim 1 wherein the attachment of the suction catheter to the cage is configured to allow an operator to pull the cage proximally by pulling the suction catheter proximally and to push the cage distally by pushing the suction catheter distally.

17. The system of claim 1 wherein, within the cage interior, the suction catheter comprises a plurality of suction openings leading to the generally hollow interior and at least some of the plurality of suction openings are located proximal to the suction catheter distal end.

18. The system of claim 1 wherein the system further comprises a delivery catheter having an interior, a proximal end leading to the interior and a distal end leading to the interior, the delivery catheter comprised of a biocompatible material and enveloping the cage and the suction catheter.

19. The system of claim 1 further comprising an inner blocking catheter located in the suction catheter generally hollow interior and moveable proximally and distally in the suction catheter generally hollow interior, the inner blocking catheter comprising an open proximal end, an open distal end and a generally hollow interior.

20. The system of claim 19 wherein the inner blocking catheter and the suction catheter each comprise an outer diameter and an inner diameter and further wherein the outer diameter of the inner blocking catheter is between about 85% to about 99.9% of the size of the inner diameter of the suction catheter.

21. The system of claim 1 wherein the heightwise and widthwise center of the suction catheter is located approximately in the heightwise and widthwise center of the cage in the relaxed state.

22. The system of claim 1 wherein, except for the suction catheter, the cage interior is hollow, and further wherein the system comprises a lead wire extending distally from the cage distal end.

23. A method of removing a blood clot from an animal using the system of claim 1, the method comprising the steps of:
a) providing a delivery catheter having an interior, a proximal end and a distal end, the delivery catheter enveloping the cage of the system of claim 1, the cage in the collapsed state;
b) deploying the cage from the delivery catheter distal end so the cage moves from the collapsed state to the relaxed state;
c) applying suction to the suction catheter to move the blood clot into the cage interior; and
d) moving the cage and blood clot proximally out of the animal.

24. The method of claim 23 wherein step c) comprises connecting a syringe or a pump to the suction catheter proximal end and using the syringe or the pump to apply the suction to the suction catheter.

25. The method of claim 23 wherein the method further comprises, before step c), providing an inner blocking catheter located in the suction catheter generally hollow interior and moving the inner blocking catheter proximally or distally in the suction catheter generally hollow interior to cover a suction opening in the suction catheter.

26. The method of claim 23 wherein steps b) and c) occur in a lung of the animal and the blood clot is a pulmonary embolism.

27. The method of claim 23 wherein step d) comprises pulling on the aspiration catheter proximally to move the cage and blood clot proximally.

28. A system for removing a blood clot from a human blood vessel, the system comprising:
a distal body comprising a cage comprising a cage proximal end comprising a plurality of proximal memory metal strips, a cage distal end, a cage length extending from the cage proximal end to the cage distal end, a cage height perpendicular to the cage length, a cage width perpendicular to the cage length and cage height, a cage interior and a cage perimeter comprised of the plurality of proximal memory metal strips, wherein the cage has a relaxed state wherein the cage has a first height and a first width, and a collapsed state wherein the cage has a second height and a second width, the second height of the cage less than the first height of the cage, the second width of the cage less than the first width of the cage; and
a suction catheter comprising a generally hollow interior, a proximal end located proximal to the cage proximal end, and a distal end, the suction catheter attached to the cage and passing into the cage interior, the suction catheter, within the cage interior, comprising at least one suction opening located between the cage proximal end and the cage distal end, the at least one suction opening leading to the generally hollow interior,
wherein the suction catheter comprises an expandable distal tip located adjacent to the suction catheter distal end and comprised of a memory metal framework and a film attached to the memory metal framework, wherein the expandable distal tip has a relaxed state wherein the expandable distal tip has a first height and a first width, and a collapsed state wherein the expandable distal tip has a second height and a second width, the second height of the expandable distal tip less than the first height of the expandable distal tip and the second width of the expandable distal tip less than the first width of the expandable distal tip, and further wherein the first height of the expandable distal tip is less than the first height of the cage and the first width of the expandable distal tip is less than the first width of the cage,
wherein the plurality of proximal memory metal strips are fixedly attached to a segment of the suction catheter between the suction catheter proximal end and the suction catheter distal end.

29. A system for removing a blood clot from a human blood vessel, the system comprising:
a distal body comprising a cage comprising a cage proximal end, a cage distal end, a cage length extending from the cage proximal end to the cage distal end, a cage height perpendicular to the cage length, a cage width perpendicular to the cage length and cage height, a cage interior and a cage perimeter comprised of a plurality of memory metal strips, wherein the cage has a relaxed state wherein the cage has a first height and a first width, and a collapsed state wherein the cage has a second height and a second width, the second height of the cage less than the first height of the cage, the second width of the cage less than the first width of the cage; and
a suction catheter comprising a generally hollow interior, a proximal end located proximal to the cage proximal end, and a distal end located proximal to the cage distal end, the suction catheter attached to the cage and passing into the cage interior, the suction catheter, within the cage interior, comprising at least one suction opening located between the cage proximal end and the cage distal end, the at least one suction opening leading to the generally hollow interior, wherein the cage is comprised of a framework comprising a plurality of cells formed by the plurality of memory metal strips, wherein, in the relaxed state, the framework comprises at least one pair of distal crowns not attached to another cell and pointing generally in the distal direction, the distal crowns in the at least one pair of distal crowns located approximately the same distance from the cage proximal end and located between 150 degrees and 180 degrees relative to each other, wherein each distal crown in the at least one pair of distal crowns forms part of a different enlarged cell, each enlarged cell having a center, wherein the centers of the enlarged cells of the at least one pair of distal crowns are between 150 degrees and 180 degrees relative to each other, and further wherein the enlarged cells are configured to allow a clot to pass therethrough and into the cage interior, and further wherein a suction opening is aligned with an enlarged cell.

* * * * *